United States Patent
Nagasaki et al.

(10) Patent No.: US 9,974,486 B2
(45) Date of Patent: May 22, 2018

(54) MEASUREMENT INFORMATION DISPLAY APPARATUS, MEASUREMENT INFORMATION DISPLAY SYSTEM, AND MEASUREMENT INFORMATION DISPLAY METHOD

(71) Applicant: Seiko Epson Corporation, Shinjuku-ku (JP)

(72) Inventors: Shintaro Nagasaki, Hara-mura (JP); Akira Hatta, Kyoto (JP); Yukari Araki, Nagahama (JP); Masaaki Nonoyama, Kyoto (JP)

(73) Assignee: Seiko Epson Corporation, Tokyo (JP)

( * ) Notice: Subject to any disclaimer, the term of this patent is extended or adjusted under 35 U.S.C. 154(b) by 0 days. days.

(21) Appl. No.: 15/669,310

(22) Filed: Aug. 4, 2017

(65) Prior Publication Data

US 2017/0332972 A1 Nov. 23, 2017

Related U.S. Application Data

(63) Continuation of application No. 14/512,121, filed on Oct. 10, 2014.

(30) Foreign Application Priority Data

Oct. 11, 2013 (JP) ................. 2013-213413

(51) Int. Cl.
*A61B 5/00* (2006.01)
*G06F 19/00* (2018.01)
(Continued)

(52) U.S. Cl.
CPC .......... *A61B 5/6898* (2013.01); *A61B 5/7435* (2013.01); *A61B 5/7445* (2013.01);
(Continued)

(58) Field of Classification Search
None
See application file for complete search history.

(56) References Cited

U.S. PATENT DOCUMENTS

| 5,550,967 A | 8/1996 | Brewer et al. |
| 5,788,655 A | 8/1998 | Yoshimura et al. |

(Continued)

FOREIGN PATENT DOCUMENTS

| EP | 2 293 175 A2 | 3/2011 |
| EP | 2 293 175 A3 | 3/2011 |

(Continued)

OTHER PUBLICATIONS

Gunther Struyf; Matlab Bar Graph—fill bars with different colours depending on sign and magnitude; Nov. 7, 2012; 3 pages; https://stackoverflow.com/questions/13266352/matlab-bar-graph-fill-bars-with-different-colours-depending-on-sign-and-magnit.*

(Continued)

*Primary Examiner* — Peter Hoang
(74) *Attorney, Agent, or Firm* — Kilpatrick Townsend & Stockton LLP

(57) ABSTRACT

A measurement information display system includes a measuring apparatus that measures biological and/or behavioral information of a user, and the measurement information display apparatus. The display apparatus includes a display unit with a screen; a communication unit that communications with the measuring apparatus to acquire the information, and a display control unit that causes the display unit to display a plurality of graphs on the screen, where the graphs represent the information. The graphs include a first graph located on a first portion of the screen and a second graph located on a second portion of the screen overlapping the first portion.

9 Claims, 63 Drawing Sheets

(51) Int. Cl.
*G06Q 10/06* (2012.01)
*G06T 11/60* (2006.01)
*G09G 5/02* (2006.01)
*G09G 5/377* (2006.01)
*A61B 5/024* (2006.01)
*A61B 5/11* (2006.01)
*H04M 1/725* (2006.01)

(52) U.S. Cl.
CPC ........ *A61B 5/7475* (2013.01); *G06F 19/3475* (2013.01); *G06Q 10/0639* (2013.01); *G06T 11/60* (2013.01); *G09G 5/02* (2013.01); *G09G 5/377* (2013.01); *A61B 5/02416* (2013.01); *A61B 5/02438* (2013.01); *A61B 5/1112* (2013.01); *A61B 5/4809* (2013.01); *G06T 2210/62* (2013.01); *G09G 2340/12* (2013.01); *G09G 2340/145* (2013.01); *G09G 2380/08* (2013.01); *H04M 1/7253* (2013.01)

(56) References Cited

U.S. PATENT DOCUMENTS

| | | | |
|---|---|---|---|
| 5,989,200 | A | 11/1999 | Yoshimura et al. |
| 8,327,277 | B2 | 12/2012 | Thakkar et al. |
| 2004/0250217 | A1 | 12/2004 | Tojo et al. |
| 2008/0214903 | A1 | 9/2008 | Orbach |
| 2009/0141593 | A1 | 6/2009 | Taha |
| 2013/0185642 | A1 | 7/2013 | Gammons |
| 2013/0197679 | A1 | 8/2013 | Balakrishnan et al. |
| 2013/0325404 | A1* | 12/2013 | Yuen .................. G06F 11/00 702/182 |
| 2014/0307878 | A1* | 10/2014 | Osborne ........... G06F 17/30743 381/56 |

FOREIGN PATENT DOCUMENTS

| | | |
|---|---|---|
| JP | H08-308820 A | 11/1996 |
| JP | 2003-219308 A | 7/2003 |
| JP | 2003-271279 A | 9/2003 |
| JP | 2007-050162 A | 3/2007 |
| JP | 2008-532587 A | 8/2008 |
| JP | 2009-136677 A | 6/2009 |
| JP | 2009-199240 A | 9/2009 |
| WO | 03/062976 A1 | 7/2003 |
| WO | 2012/038742 A1 | 3/2012 |
| WO | 2012/071564 A2 | 5/2012 |
| WO | 2012/071564 A3 | 5/2012 |
| WO | 2013/109916 A1 | 7/2013 |

OTHER PUBLICATIONS

Spagnolli A. et al, Eco-Feedback on the Go: Motivating Energy Awareness, Computer, IEEE, US, vol. 44, No. 5, May 1, 2011, pp. 38-45.

Extended European search report, dated Feb. 23, 2015, of the corresponding European Application No. 14188284.5. (7 pages).

Non-Final Office Action dated Oct. 22, 2015 in related U.S. Appl. No. 14/512,121 (21 pages).

Final Office Action dated Apr. 13, 2016 in related U.S. Appl. No. 14/512,121 (25 pages).

Non-Final Office Action dated May 5, 2017 in related U.S. Appl. No. 14/512,121 (25 pages).

* cited by examiner

MS3

MEASUREMENT INFORMATION DISPLAY APPARATUS, MEASUREMENT INFORMATION DISPLAY SYSTEM, AND MEASUREMENT INFORMATION DISPLAY METHOD

CROSS REFERENCE TO RELATED APPLICATIONS

This application is a continuation of U.S. patent application Ser. No. 14/512,121, filed Oct. 10, 2014, which claims priority to Japanese Patent Application No. 2013-213413, filed Oct. 11, 2013, the disclosures of which are incorporated herein by reference.

BACKGROUND

1. Technical Field

The present invention relates to a measurement information display apparatus, a measurement information display system, and a measurement information display method, for measuring and displaying a user's biological and/or behavioral information, such as heart rate, stress, exercise, sleep, calories consumed, calories burned, or number of steps taken.

2. Related Art

A biological information measurement system has been known that measures biological information such as a pulse of a user and manages the biological information (see, for example, JP-A-2007-50162 (Patent Literature 1)).

The biological information measurement system described in Patent Literature 1 includes a cellular phone. The cellular phone includes a biological-information measuring unit, a life-activity-recording processing unit, a key input unit, a storing unit, and a display unit. The biological-information measuring unit includes a sensor necessary for measuring biological information such as a pulse, a body temperature, and an amount of exercise (including the number of steps). The life-activity-recording processing unit is realized by various processors. The life-activity-recording processing unit receives, from the key input unit, an input of life activity information to be recorded and causes, on the basis of the received life activity information, the storing unit to store life activities of a user in association with the measured biological information or measurement date and time. The display unit displays, under the control by the life-activity-recording processing unit, an input receiving screen for the life activity information and displays a pulse, the number of steps, and the like in a predetermined period as a graph.

With such a biological information measurement system, the user can check biological information of the user and grasp a health status and a progress state of a diet.

However, in the biological information measurement system described in Patent Literature 1, when the user checks transitions of the pulse and transitions of the number of steps in the predetermined period and a recovery state after an exercise, the user needs to switch and display display screens for the respective items.

On the other hand, in a portable terminal such as the cellular phone, since a display area of a screen is small, it is difficult to display the display screens for the respective items at a time.

Therefore, there has been a demand for a new presentation method for information.

SUMMARY

An advantage of some aspects of the invention is to provide a measurement information display apparatus, a measurement information display system, and a measurement information display method that can make it easy to grasp various kinds of information.

The system includes a measuring apparatus that measures biological and/or behavioral information of a user, and the measurement information display apparatus. The display apparatus includes a display unit with a screen; a communication unit that communications with the measuring apparatus to acquire the information, and a display control unit that causes the display unit to display a plurality of graphs on the screen, where the graphs represent the information. The graphs include a first graph located on a first portion of the screen and a second graph located on a second portion of the screen overlapping the first portion.

The screen may generally define a first plane, and the graphs may define an array that is transverse to the first plane, such as by defining a polygon in a second plane transverse to the first plane.

When a user inputs a moving operation for moving the second graph in a direction toward the first portion of the screen, the display control unit rotates the array in the direction, thereby moving the second graph to the first portion of the screen and moving the first graph to a third portion of the screen in the direction.

The first graph may generally be disposed in the first plane and the second graph may generally be disposed parallel to but set back from the plane.

The second graph may be displayed at a higher transparency and/or in a lighter color than the first graph.

The second portion of the screen may be smaller than the first portion of the screen.

The graphs may be doughnut graphs.

The first portion of the screen may display both the first graph and a numerical value indicative of the information.

Numerical values corresponding to the information indicated by the first graph may be displayed on a third portion of the screen.

The display may also include a third graph, where the first graph is larger than both the second graph and the third graph.

BRIEF DESCRIPTION OF THE DRAWINGS

The invention will be described with reference to the accompanying drawings, wherein like numbers reference like elements, and in which.

DESCRIPTION OF EXEMPLARY EMBODIMENTS

Overall Configuration of a Measurement Information Management System

An embodiment of the invention is explained below with reference to the drawings.

Figure 1:
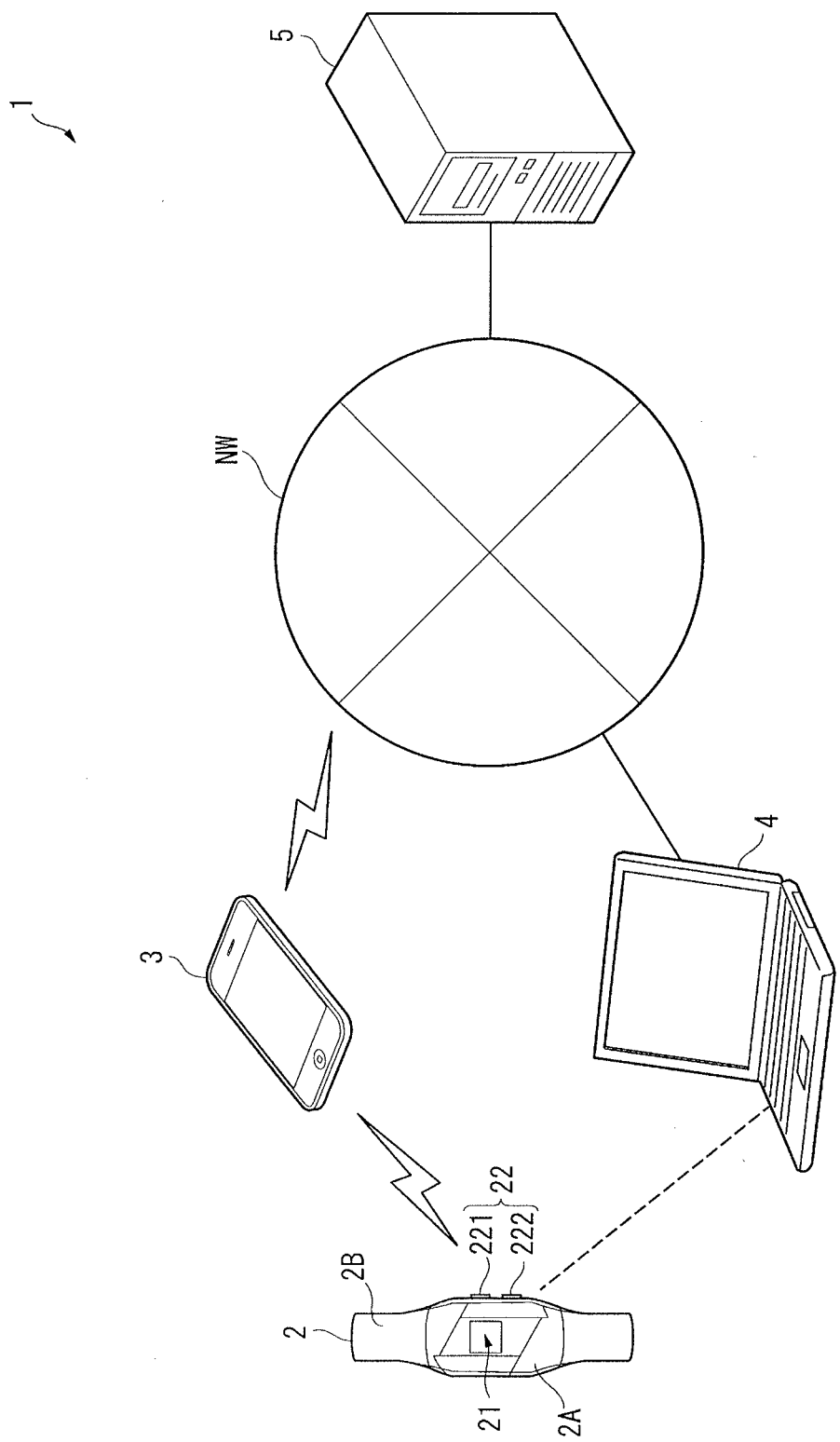
FIG. 1 is a diagram showing the schematic configuration of a measurement information management system according to an embodiment of the invention.

FIG. 1 is a diagram showing the schematic configuration of a measurement information management system 1 according to this embodiment.

The measurement information management system 1 according to this embodiment includes a measurement information display system according to the invention. The measurement information management system 1 includes, as shown in FIG. 1, a measuring apparatus 2, information terminals 3 and 4 functioning as measurement information display apparatuses, a management server 5, and a network NW. In the measurement information management system 1, measurement information (biological information and behavior information of a user) measured by the measuring apparatus 2 is acquired and stored by the information terminals 3 and 4 and transmitted to the management server 5 by the information terminals 3 and 4 via the network NW and stored in the management server 5, whereby the measurement information is managed.

The apparatuses included in the measurement information management system 1 are explained below. Note that, as the network NW, a communication network (including a telephone line) forming the Internet, a wireless LAN (Local area Network) communication network, and a satellite communication network can be used.

Configuration of the Management Server

The management server 5 is connected to the information terminals 3 and 4 via the network NW. The management server 5 stores user information transmitted from the information terminals 3 and 4 and stores the transmitted measurement information and event contents and the like explained below in association with the user information. The management server 5 transmits, in response to a request from the information terminals 3 and 4, the measurement information and the like stored in association with the user information of users of the information terminals 3 and 4.

Configuration of the Measuring Apparatus

Figure 2:
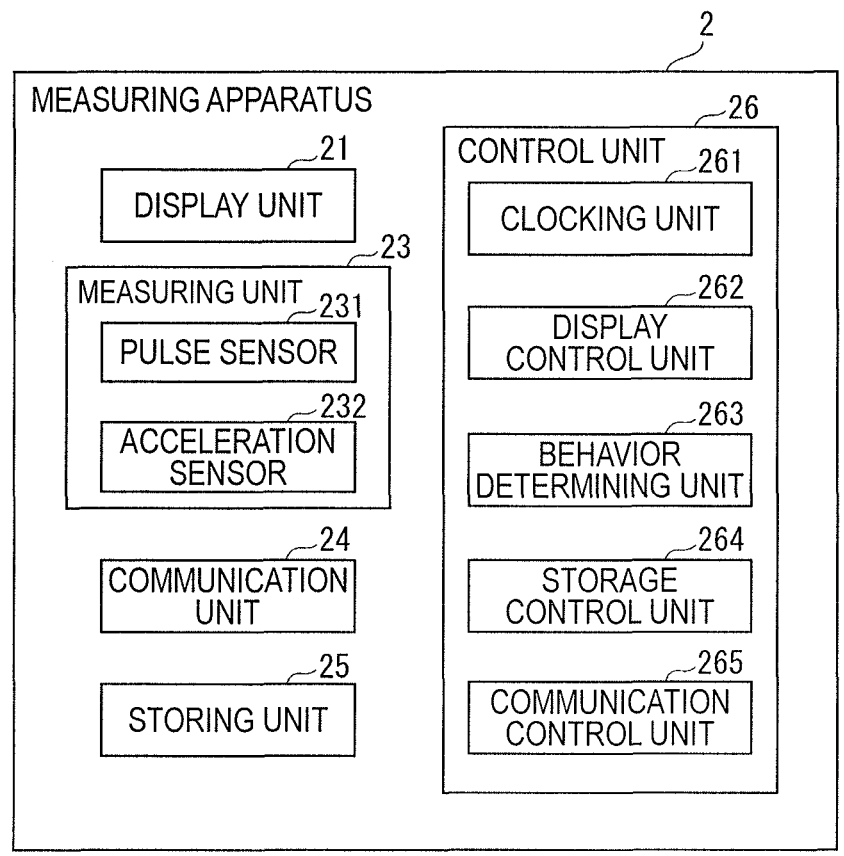
FIG. 2 is a block diagram showing the configuration of a measuring apparatus in the embodiment.

FIG. 2 is a block diagram showing the configuration of the measuring apparatus 2.

The measuring apparatus 2 is worn on a wearing part (e.g., the wrist) of the user and used. The measuring apparatus 2 measures time, measures a pulse rate serving as biological information, acceleration serving as behavior information, and the like, and transmits these kinds of measurement information to the information terminals 3 and 4. As shown in FIGS. 1 and 2, the measuring apparatus 2 includes a housing 2A and a band 2B and includes a display unit 21, an operation unit 22, a measuring unit 23, a communication unit 24, a storing unit 25, and a control unit 26 provided in the housing 2A. One exemplary measuring apparatus is described in detail in the present assignee's co-pending application Ser. No. 14/463,519, titled "Physiological Information Measuring Apparatus," filed Aug. 19, 2014, which is hereby incorporated by reference.

The display unit 21 displays an operation state of the measuring apparatus 2. The display unit 21 is configured by any one of various display panels such as a liquid crystal panel, an organic EL (Electro-Luminescence) panel, and an electrophoresis panel.

The operation unit 22 is a unit for operating the measuring apparatus 2. In this embodiment, the operation unit 22 includes buttons 221 and 222 (see FIG. 1) that project from and retract into the housing 2A. The operation unit 22 outputs an operation signal corresponding to the button depressed by the user to the control unit 26.

The measuring unit 23 includes various sensors capable of detecting biological information and behavior information of the wearing user. In this embodiment, the measuring unit 23 includes a pulse sensor 231 and an acceleration sensor 232 and outputs measurement signals of the sensors to the control unit 26.

The pulse sensor 231 is provided on the back of the housing 2A and is brought into contact with the wearing part to measure a pulse rate of the user. Specifically, the pulse sensor 231 is configured by a photoelectric sensor including a light emitting element and a light receiving element. In a state in which the measuring apparatus 2 is worn in the wearing part, the pulse sensor 231 causes the light emitting element to irradiate light on a living organism, detects a light amount change of reflected light received by the light receiving element to detect a pulse wave, and processes the pulse wave with a publicly-known method such as a frequency analysis to measure a pulse rate. That is, the light irradiated on the living organism is partially absorbed by blood vessels. However, an absorption ratio by the blood vessels changes because of the influence of a pulse. A reflected light amount in the blood vessels also changes. Therefore, it is possible to measure a pulse rate from the light amount change of the reflected light that reflects a change in a blood flow rate detected by the light receiving element. Note that, as the pulse sensor 231, instead of the photoelectric sensor, an ultrasonic sensor that detects contraction of the blood vessels with ultrasound and measures a pulse rate may be adopted or a sensor or the like that feeds a feeble current from an electrode into the body and measures a pulse rate may be adopted.

The acceleration sensor 232 measures, as a movement of the user, acceleration that changes according to the movement of the measuring apparatus 2.

The communication unit 24 is a communication module that communicates with an external apparatus such as the information terminal 3 by radio. The communication unit 24 transmits information input from the control unit 26 to an external apparatus to which communication connection is established and outputs information (e.g., user information) received from the external apparatus to the control unit 26. Examples of the communication unit 24 include a communication module conforming to a Bluetooth (registered trademark) standard and a wireless LAN module conforming to an IEEE802.11 standard.

The storing unit 25 is configured by a flash memory or the like and stores various computer programs and data necessary for measurement. For example, the storing unit 25 stores, as the data, age calculated from the date of birth, gender, physical information including height and weight, and the like of the user. Besides, the storing unit 25 stores measurement information obtained by the measuring unit 23.

The control unit 26 includes circuit elements such as a CPU (Central Processing Unit) and a memory and controls the operation of the measuring apparatus 2. The CPU executes and processes the computer programs stored in the storing unit 25, whereby the control unit 26 functions as a clocking unit 261, a display control unit 262, a behavior determining unit 263, a storage control unit 264, and a communication control unit 265.

The clocking unit 261 clocks the present time.

The display control unit 262 controls the operation of the display unit 21 and causes the display unit 21 to display an operation state, a measurement result, and the like of the measuring apparatus 2.

The behavior determining unit 263 determines a pulse rate measured by the pulse sensor 231 (hereinafter sometimes referred to as measured pulse rate) and acceleration measured by the acceleration sensor 232 (hereinafter sometimes referred to as measured acceleration) to determine the behavior of the user.

For example, if transitions of the measured acceleration are within an exercise acceleration range (a range of transitions of acceleration classified into exercise), if the measured pulse rate is within an exercise pulse rate range (a range of transitions of a pulse rate classified into exercise and, for example, a range equal to or larger than 70 times/minute (70 bpm) and equal to or smaller than 100 times/minute (100 bpm)), the behavior determining unit 263 determines that exercise is carried out.

Note that these ranges are changed on the basis of, besides input operation to the operation unit 22 and remote operation by the information terminals 3 and 4, user information (age, gender, height, weight, and the like of the user) received from the information terminals 3 and 4. The control unit 26 can change a first threshold and a second threshold on the basis of an average of pulse rates (e.g., an average of pulse rates during exercise) stored in the storing unit 25.

Further, when determining that the exercise is carried out, if the transitions of the measured acceleration and the measured pulse rate are respectively within ranges in which body fat tends to be consumed, the behavior determining unit 263 determines that exercise that tends to efficiently consume fat (exercise in a fat burning zone) is carried out. Note that the zone is described in JP-A-2013-22256.

Further, if the transitions of the measured acceleration are not within the exercise acceleration range (the range of transitions of acceleration classified into exercise), if the measured pulse rate is within the exercise pulse rate range (the range of transitions of a pulse rate classified into exercise), the behavior determining unit 263 determines that the user is in an excited state not due to exercise.

On the other hand, if the transitions of the measured acceleration are not within the exercise acceleration range (the range of transitions of acceleration classified into exercise), if the measured pulse rate is not within the exercise pulse rate range (the range of transitions of a pulse rate classified into exercise), the behavior determining unit 263 determines that the user is in a relaxed state. The behavior determining unit 263 may calculate, using a publicly-known method, an index HF/LF or the like representing an active state of a sympathetic nerve and a parasympathetic nerve from the pulse wave measured by the measuring unit and determine the excited state or the relaxed state.

The storage control unit 264 causes the storing unit 25 to store a measurement result (the measured pulse rate and the measured acceleration) by the measuring unit 23 in association with measurement time (time clocked by the clocking unit 261). The storage control unit 264 causes the storing unit 25 to store time when the behavior determining unit 263 determines that the user is in a mental state of any one of the excited state (the excited state due to exercise and the excited state not due to exercise) and the relaxed state (hereinafter sometimes referred to as mental state determination time). The measurement time and the measurement result stored in this way are transmitted to the information terminal 3 by the communication unit 24. When the measurement information stored in the storing unit 25 is transmitted to the information terminal 3 or the information terminal 4, the storage control unit 264 deletes the measurement information. Note that the transmission processing may be adapted to directly transmit the measurement information from the measuring apparatus 2 to the management server 5 via a wireless LAN or the like.

The communication control unit 265 causes the communication unit 24 to transmit information in which the measured pulse rate and the measured acceleration stored in the storing unit 25 and the measurement time of the measured pulse rate and the measured acceleration are associated and transmission information including the determination time to the information terminals 3 and 4. The communication control unit 265 causes the communication unit 24 to transmit the transmission information to the information terminal 3 once in approximately one hour and causes the communication unit 24 to transmit the transmission information to the information terminal 3 when it is determined that the user is in any one of the mental states. The communication control unit 265 causes the storage control unit 264 to store, in the storing unit 25, various kinds of information such as the user information received from the information terminals 3 and 4 via the communication unit 24.

Note that, when the measuring apparatus 2 is communicably connected to the information terminal 4 configured by a PC (Personal Computer) or the like, the communication control unit 265 transmits the transmission information in response to a request of the information terminal 4.

Configuration of the Information Terminal

The information terminals 3 and 4 transmit the user information set according to the input operation to the information terminals 3 and 4 to the measuring apparatus 2 as explained above. Besides, the information terminal 3 communicates with the measuring apparatus 2 by radio and the information terminal 4 communicates with the measuring apparatus 2 via a not-shown cradle, whereby the information terminals 3 and 4 receive the transmission information from the measuring apparatus 2 and store the transmission information. Further, the information terminals 3 and 4 transmit contents of the received transmission information to the management server 5 via the network NW.

Figure 3:
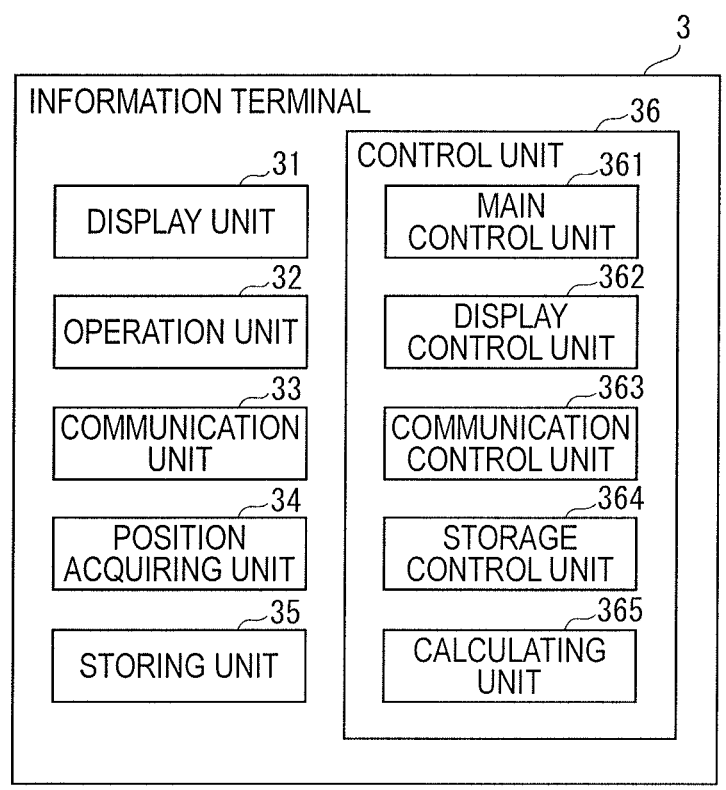
FIG. 3 is a block diagram showing the configuration of an information terminal in the embodiment.

FIG. 3 is a block diagram showing the configuration of the information terminal 3.

In this embodiment, the information terminal 3 is configured by a portable information terminal apparatus such as a cellular phone or a smart phone (a multifunction cellular phone). The information terminal 3 is communicably connected to the measuring apparatus 2 by radio. In the measurement information management system according to this embodiment, the user wears the measuring apparatus 2 and carries the information terminal 3.

The information terminal 3 is equivalent to the measurement information display apparatus according to the invention. The information terminal 3 includes, as shown in FIG. 3, a display unit 31, an operation unit 32, a communication unit 33, a position acquiring unit 34, a storing unit 35, and a control unit 36.

The display unit 31 is configured by any one of the various display panels explained above. The display unit 31 displays various display screens under the control by a display control unit 362 included in the control unit 36. Specifically, the display unit 31 displays an image corresponding to an image signal input from the display control unit 362.

Although not shown in the figure, the operation unit 32 includes, besides physical keys functioning as buttons provided on the outer surface of the information terminal 3, a touch panel provided to correspond to a display area of an image in the display unit 31. The operation unit 32 outputs, to the control unit 36, an operation signal corresponding to the operation by the user on the operation unit 32.

Although not shown in the figure, the communication unit 33 includes a first communication module communicable with an external apparatus such as the measuring apparatus 2 and a second communication module communicable with the management server 5 on the network NW. The communication unit 33 communicates with the external apparatus and the management server 5 under the control by a communication control unit 363 included in the control unit 36. Note that, when communicable with the measuring apparatus 2 and the management server 5 in the same communication form, the communication unit 33 may include only one of the first communication module and the second communication module.

The position acquiring unit 34 acquires position information indicating the present position of the information terminal 3 and outputs the position information indicating the present position to the control unit 36. The position acquiring unit 34 includes a GPS (Global Positioning System) sensor, receives GPS signals transmitted from a plurality of GPS satellites orbiting on the satellite orbit of the earth, and acquires position information of the present location of the information terminal 3 (in other words, the present location of the user).

Note that the position acquiring unit 34 is not limited to the configuration for acquiring the present position of the information terminal 3 on the basis of the received GPS signals and may be configured to acquire the position information on the basis of position information and the like of a base station connected to the position acquiring unit 34 when communicating with the management server 5.

The storing unit 35 is configured by an HDD (Hard Disk Drive), a flash memory, or the like and stores various computer programs and data necessary for the operation of the information terminal 3. As the data, the storing unit 35 stores, for example, user information set according to the operation by the user on the operation unit 32, transmission information transmitted from the measuring apparatus 2, and position information acquired by the position acquiring unit 34. Further, as the computer programs, the storing unit 35 has stored therein, besides an OS (Operating System), a computer program concerning a measurement information management application for displaying a display screen explained below and managing transmission information received from the measuring apparatus 2.

The control unit 36 includes a CPU and a memory and controls the operation of the information terminal 3. The CPU executes the computer programs stored in the storing unit 35, whereby the control unit 36 functions as a main control unit 361, the display control unit 362, the communication control unit 363, a storage control unit 364, and a calculating unit 365.

The main control unit 361 mainly controls the operation of the information terminal 3. For example, the main control unit 361 executes the measurement information management program stored in the storing unit 35 and manages information input by the user using the operation unit 32 and information received from the measuring apparatus 2 and the management server 5 by the communication unit 33.

The display control unit 362 causes the display unit 31 to display an operation time screen of the information terminal 3. Besides, the display control unit 362 generates an execution time screen of the measurement information management application and causes the display unit 31 to display the execution time screen. The execution time screen (a display screen) is explained in detail below. That is, the display control unit 362 is equivalent to the display control unit according to the invention in the information terminal 3.

The communication control unit 363 controls the operation of the communication unit 33. For example, the communication control unit 363 establishes communication connection to the measuring apparatus 2 and the server 5 and further transmits and receives information to and from the measuring apparatus 2 and the server 5 using the communication unit 33.

The storage control unit 364 controls the operation of the storing unit 35. For example, the storage control unit 364 causes the storing unit 35 to store user information and behavior information of the user input by the user. The storage control unit 364 causes the storing unit 35 to store information (including the measurement information) received from the measuring apparatus 2 and the management server 5 by the communication unit 33.

Figure 4:
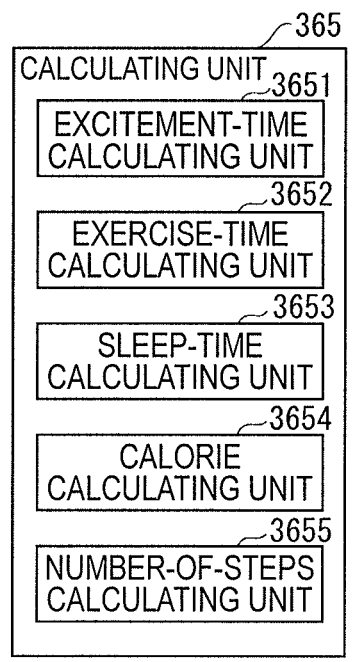
FIG. 4 is a block diagram showing the configuration of a calculating unit in the embodiment.

FIG. 4 is a block diagram showing the configuration of the calculating unit 365.

The calculating unit 365 calculates, on the basis of the measurement information received via the communication unit 33 and stored in the storing unit 35 and the input user information, time of an excited state among mental states of the user (an excitement time), an exercise time, a sleep time, a calorie difference, and the number of steps. The calculating unit 365 includes an excitement-time calculating unit 3651, an exercise-time calculating unit 3652, a sleep-time calculating unit 3653, a calorie calculating unit 3654, and a number-of-steps calculating unit 3655 as functional units according to calculation target items.

The excitement-time calculating unit 3651 calculates time of an excited state (a state in which a pulse rate exceeds a predetermined value) of the user on the basis of the measurement information. In this case, the excitement-time calculating unit 3651 calculates time in which the user is in the excited state because of exercise (an excitement time during exercise) and time in which the user is in the excited state not because of exercise (an excitement time during non-exercise).

The exercise-time calculating unit 3652 calculates a normal exercise time of the user (hereinafter referred to as normal exercise time) on the basis of the measurement information. Further, the exercise-time calculating unit 3652 calculates, on the basis of the user information, an exercise time in which exercise in the fat burning zone set on the basis of the user information is carried out, that is, an in-zone exercise time.

The sleep-time calculating unit 3653 calculates a sleep time of the user on the basis of the measurement information. In this case, the sleep-time calculating unit 3653 calculates an awakening time, a light sleep time, and a deep sleep time in a period determined as the sleep time.

The calorie calculating unit 3654 calculates a total value of intake calories on the basis of meal information input by the user on an input screen ED explained below and calculates a total value of consumed calories of the user on the basis of basal metabolism calculated from age, gender, and weight included in the user information, a physical activity level set by the user, and the measurement information. Further, the calorie calculating unit 3654 determines which of the total value of the intake calories and the total value of the consumed calories is larger and calculates a difference between the total values.

The number-of-steps calculating unit 3655 calculates the number of steps of the user on the basis of the measurement information (information of the pulse sensor 231 and the acceleration sensor 232 of the measuring apparatus 2) and the height included in the user information. Further, the number-of-steps calculating unit 3655 calculates the number of steps during exercise in the fat burning zone set on the basis of the user information.

Among the calculating units 3651 to 3655, the excitement-time calculating unit 3651, the exercise-time calculating unit 3652, the calorie calculating unit 3654, and the number-of-steps calculating unit 3655 calculate values of the respective items in units of one day. The sleep-time calculating unit 3653 calculates a sleep time across the midnight line as a sleep time on a date at the midnight.

Further, the calculating units 3561 to 3655 calculate total values in units of a day, units of the nearest week, and units of the nearest month for each of items corresponding to the calculating units 3561 to 3655 and calculate total values from the beginning of a week to the present date and total values from the beginning of a month to the present date.

Calculation results by the calculating units 3651 to 3655 are displayed on the execution time screen of the measurement information management application explained below.

Examples of Display Screens

The information terminal 3 displays display screens corresponding to kinds of operation by the user during execution of the measurement information management application. The display screens are generated by the display control unit 362 and displayed on the display unit 31. The display screens are explained below.

Note that a constant display area DA indicating a state of the information terminal 3 is set at the top ends on the display screens. In the constant display area DA, a gauge indicating reception sensitivity of a radio wave used for communication with the network NW, the present time, and a battery residual amount are arranged. Various keys included in the display screens are software keys. When touched (tapped or clicked) by the user, the keys are assumed to be pressed. Further, when input fields and setting fields set on the display screens are selected (tapped or clicked), although not shown in the figure, a screen keyboard and an input character display field are displayed. When the user presses a decision key set on the screen keyboard, an input character is set in the input field and the setting field corresponding thereto.

Note that, in this embodiment, various kinds of information necessary in processing explained below are input by an input by the software keys of the display unit 31 of the information terminal 3, swipe operation, tap operation, and the like. However, the information may be input using other input devices such as a keyboard and a touch pen.

Login Screen

Figure 5:
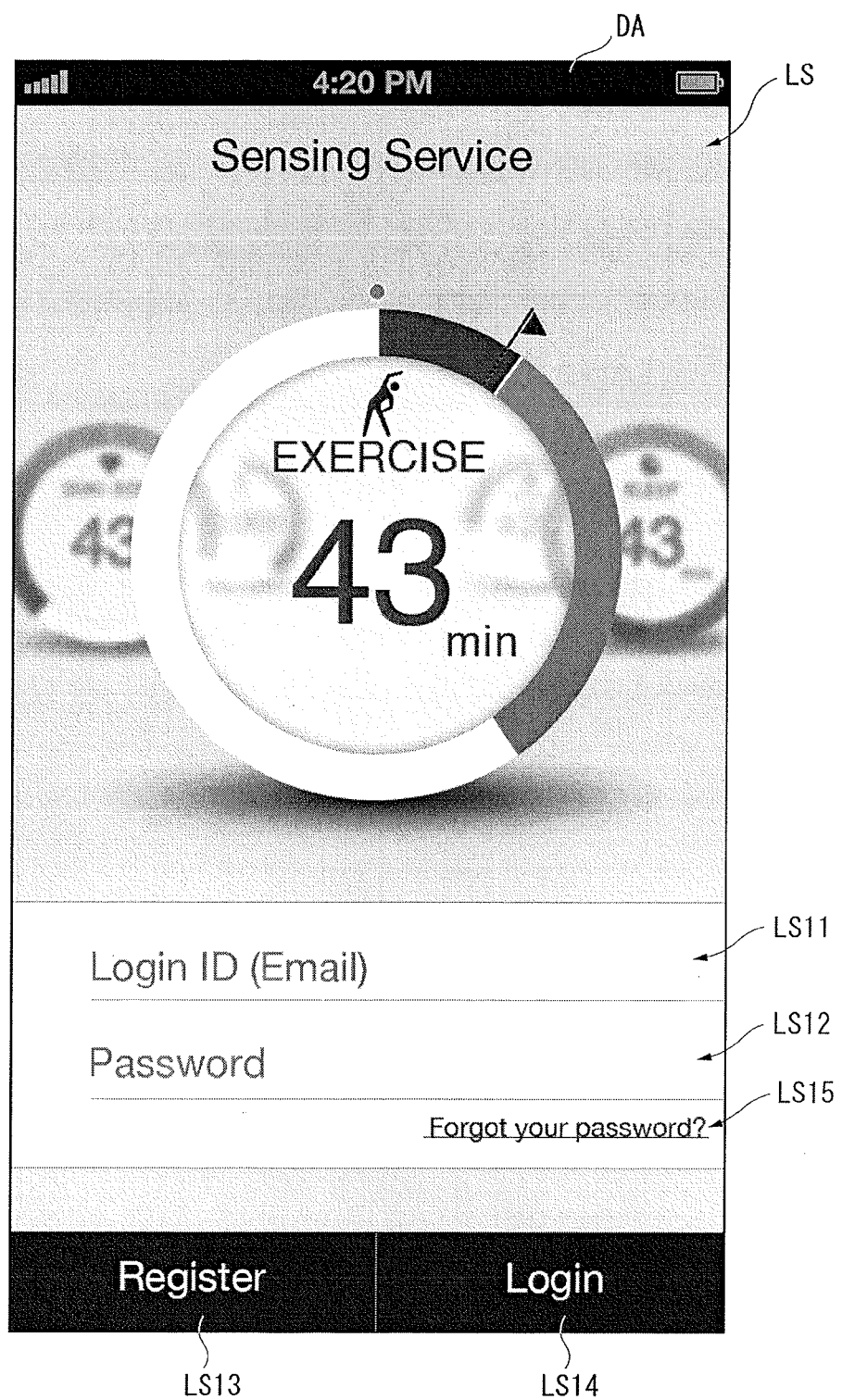
FIG. 5 is a diagram showing a login screen in the embodiment.

FIG. 5 is a diagram showing an example of a login screen LS. FIGS. 6 to 11 are diagrams respectively showing examples of screens RS1 to RS5 during registration.

When the measurement information management application is started in the information terminal 3, the display control unit 362 causes the display unit 31 to display the login screen LS shown in FIG. 5. On the login screen LS, a login ID (an E-mail address) input field LS11 and a password input field LS12 are set and a registration key LS13 and a login key LS14 are set.

Note that, when a link LS15 inscribed as "Forgot your password" is pressed, a screen (not shown in the figure) indicating measures that the user should take when the user forgets a password is displayed.

When the login key LS14 is pressed, the main control unit 361 compares a login ID and a password stored in the storing unit 35 or the management server 5 and a login ID and a password set in the input fields LS11 and LS12. When the login IDs and the passwords do not match, the display screen does not transition from the login screen LS. A message indicating that the login ID or the password is incorrect is displayed.

On the other hand, when the login IDs and the passwords respectively match, a main screen MS (see FIG. 12) explained below is displayed. When the user logs in on the login screen LS, the measurement information management application operates as resident software. Even if the execution time screen of the application is not always displayed, the application is under execution.

Figure 6:
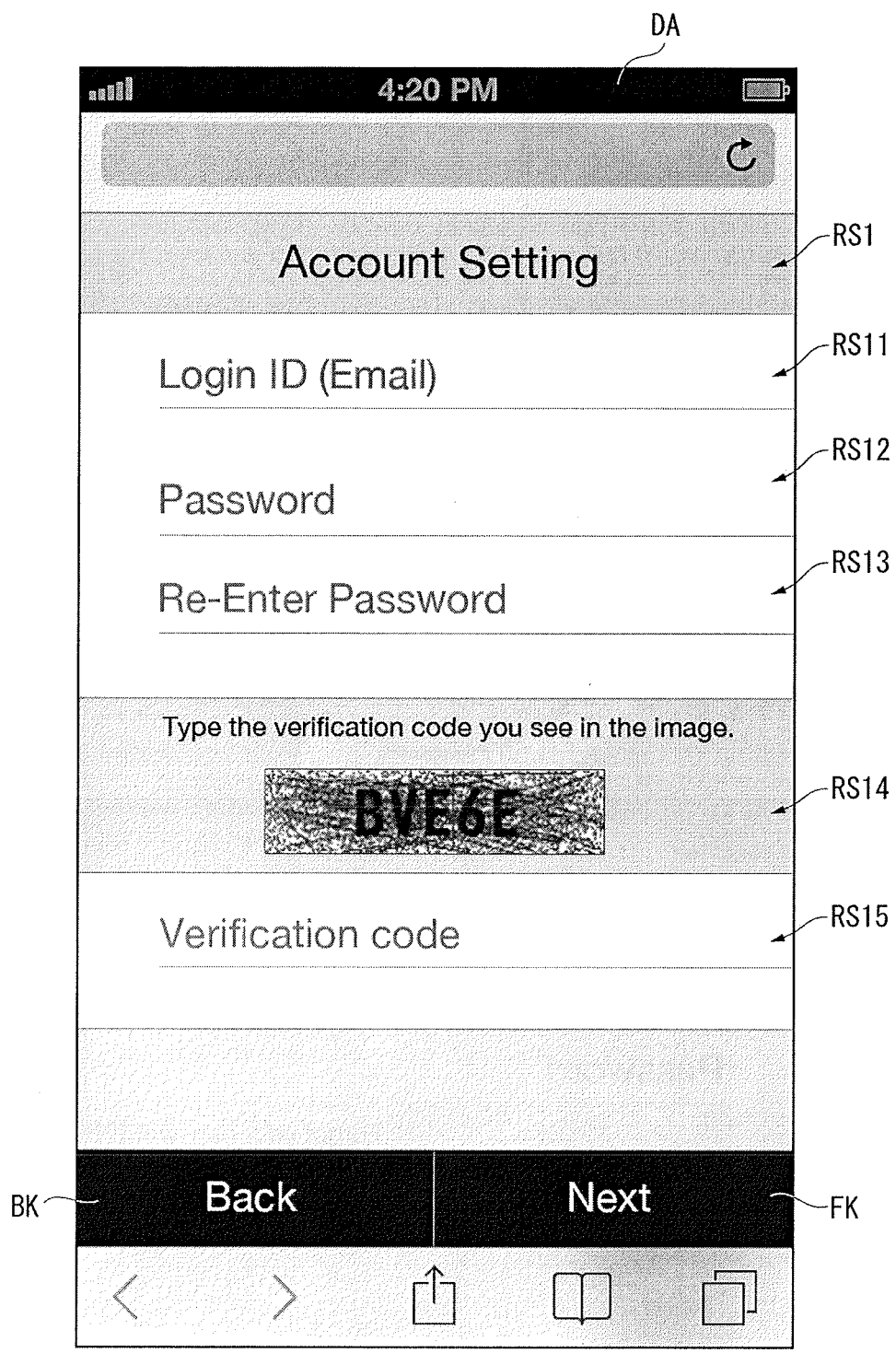
FIG. 6 is a diagram showing a registration screen in the embodiment.

When the registration key LS13 is entered, a registration screen RS1 shown in FIG. 6 is displayed.

The registration screen RS1 is a screen for setting a login ID and a password to be registered in the management server 5. On the registration screen RS1, a login ID input field RS11, password input fields RS12 and RS13, a check code display field RS14, a check code input field RS15, a back key BK, and a forward key FK are set.

The login ID input field RS11 and the password input fields RS12 and RS13 are respectively input fields for setting a login ID (an E-mail address) and a password to be registered.

The check code display field RS14 is a display field for a check code, which is a random character string. The check code input field RS15 is an input field to which the user inputs the displayed check code.

When the back key BK is pressed, the preceding screen is displayed.

When the forward key FK is pressed, the next screen is displayed.

Figure 7:
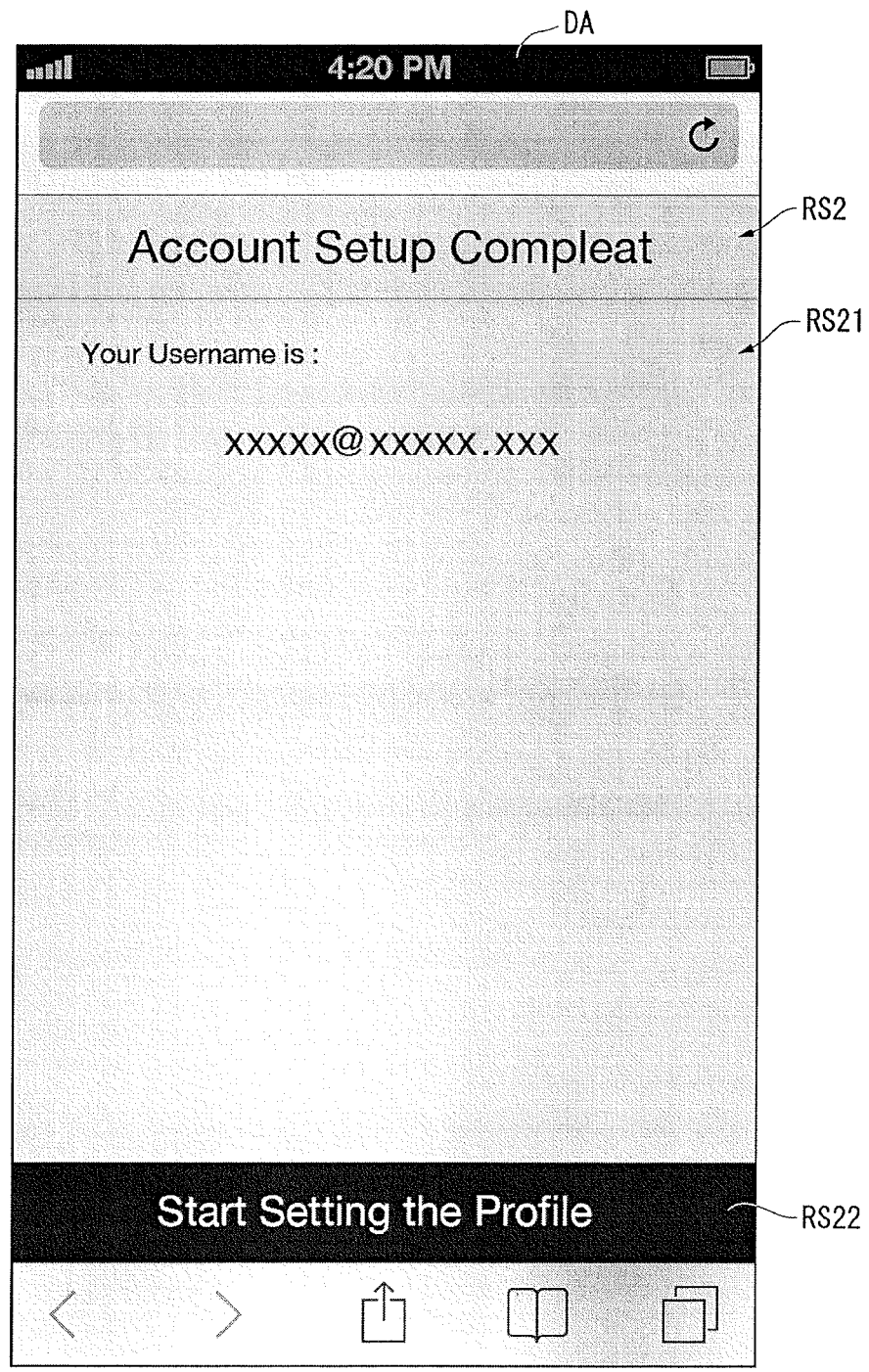
FIG. 7 is a diagram showing a check screen in the embodiment.

When the forward key FK is pressed while the registration screen RS1 is displayed, the main control unit 361 transmits input account information (a login ID and a password) to the management server 5. The management server 5 determines whether registration with the account information is possible. If the registration is possible, the account information is registered in the management server 5. A check screen RS2 shown in FIG. 7 is displayed on the display unit 31 of the information terminal 3.

On the check screen RS2, a display field RS21 in which the registered login ID (E-mail address) is displayed and a setting start key RS22 for a profile are set.

Figure 8:
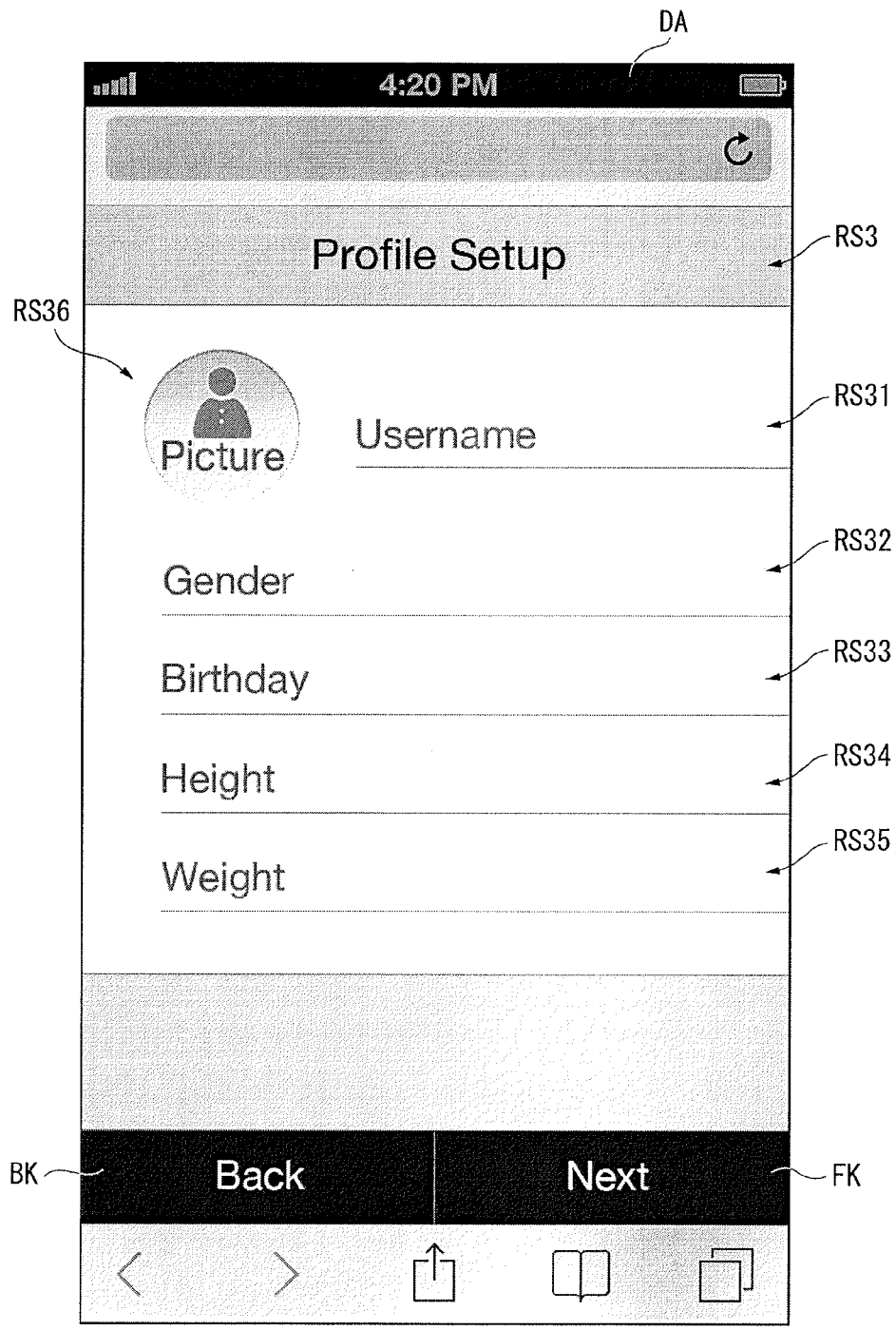
FIG. 8 is a diagram showing a setting screen in the embodiment.

When the setting start key RS22 is pressed on the check screen RS2, a setting screen RS3 for a profile shown in FIG. 8 is displayed.

On the setting screen RS3, a user name input field RS31, a gender setting field RS32, a date-of-birth setting field RS33, a height setting field RS34, a weight setting field RS35, and an image setting field RS36, which are respectively requisite items, are set and the back key BK and the forward key FK are set.

Note that the image setting field RS36 is an area for setting an image such as a photograph of the user. An image cut in a circular shape having a predetermined dimension from the center of an image selected by the user is set.

Figure 9:
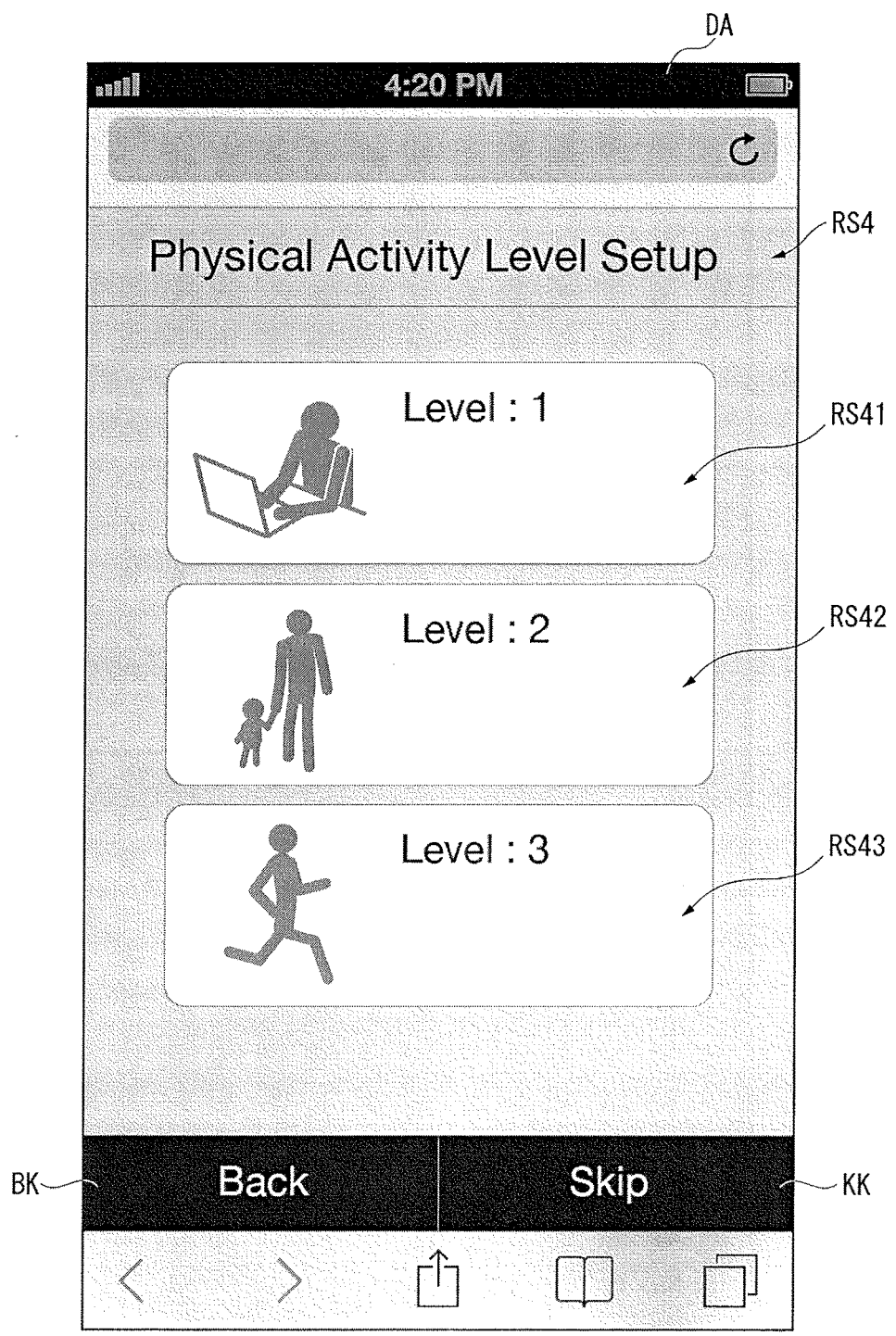
FIG. 9 is a diagram showing a setting screen in the embodiment.

On the setting screen RS3, after items of the fields RS31 to RS36 are input and set, when the forward key FK is pressed, a setting screen RS4 for a physical activity level shown in FIG. 9 is displayed.

On the setting screen RS4, selection fields RS41 to RS43 for a physical activity level, the back key BK, and a skip key KK are set. Note that, when the skip key KK is pressed, setting of a physical activity level is skipped and the setting screen RS4 is transitioned to another screen.

Characters "Level: 1" and an explanatory note "often sits in a whole day and rarely exercise" (not shown in the figure) are written in the selection field RS41. Characters "Level: 2"

and an explanatory note "often sit in a whole day but perform standing work, shopping, house work, and light exercise" (not shown in the figure) are written in the selection field RS42. Characters "Level: 3" and an explanatory note "often move and perform work while standing" (not shown in the figure) are written in the selection field RS43.

Figure 10:
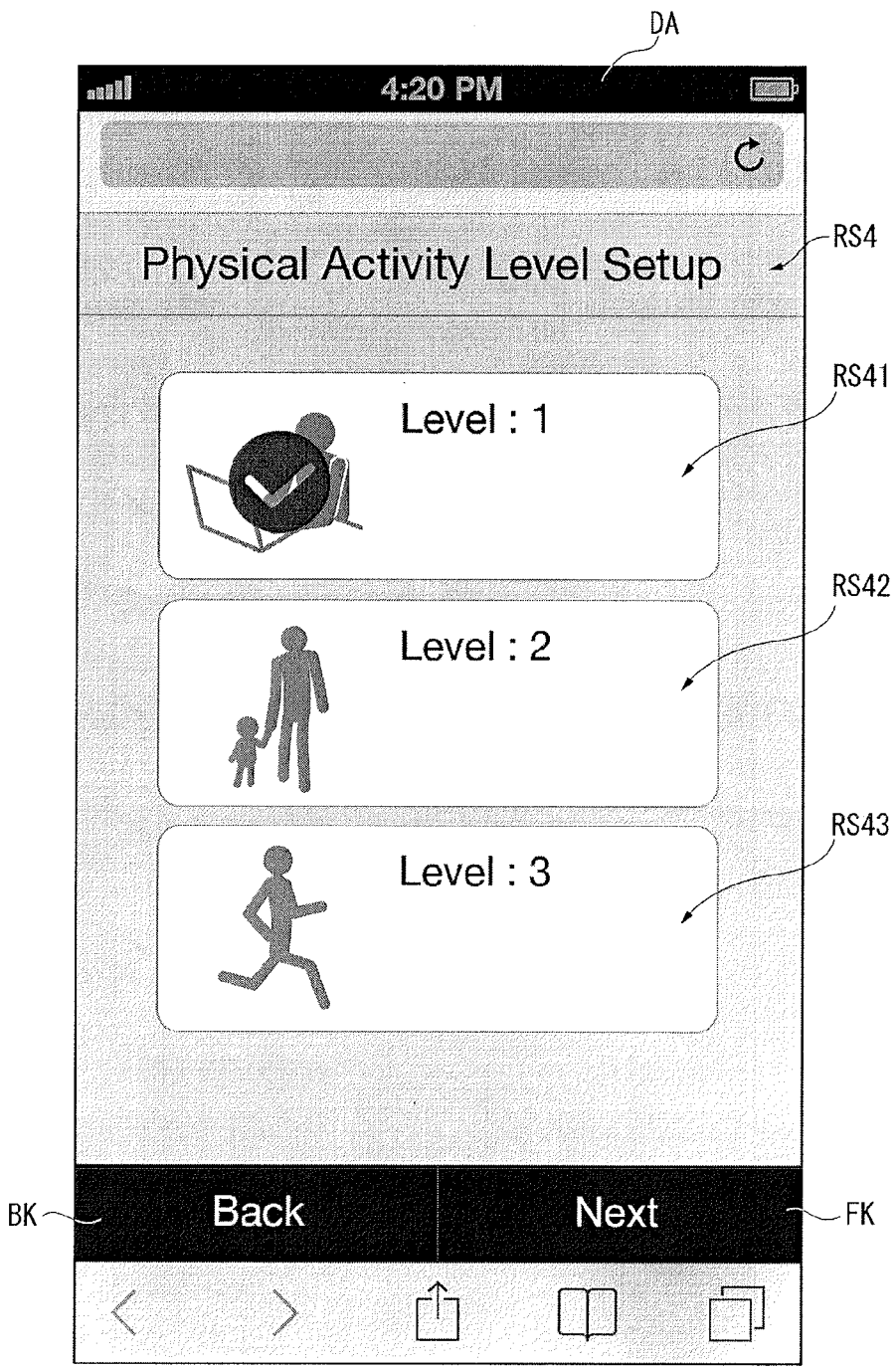
FIG. 10 is a diagram showing the setting screen checked with a check mark in the embodiment.

When any one of the selection fields RS41 to RS43 is selected, as shown in FIG. 10, a check mark is checked in the selected selection field and the skip key KK is replaced with the forward key FK.

Figure 11:
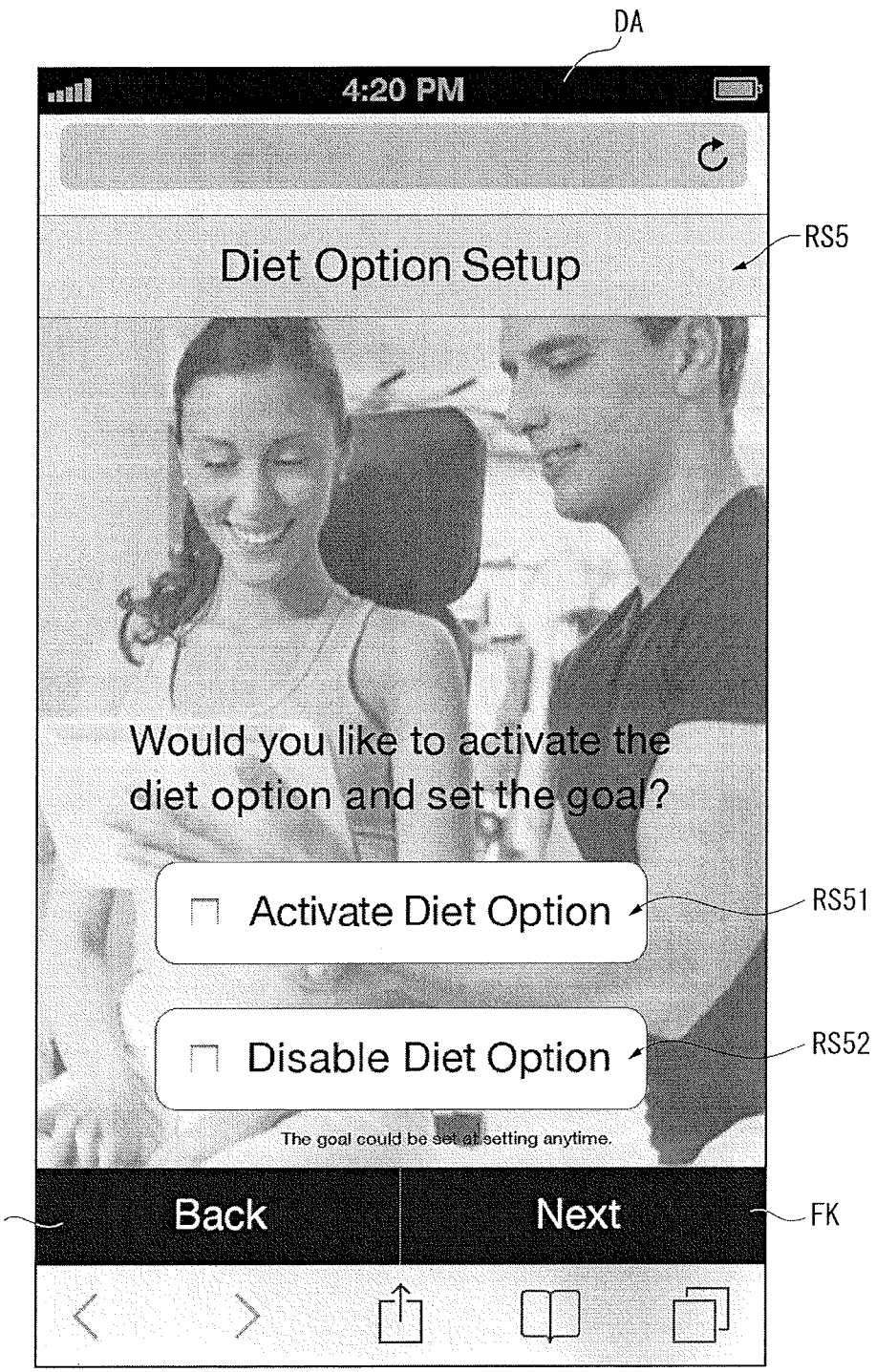
FIG. 11 is a diagram showing a selection screen in the embodiment.

When the forward key FK is pressed on the setting screen RS4, a selection screen RS5 for selecting whether a diet option shown in FIG. 11 is activated is displayed.

On the selection screen RS5, a selection field RS51 in which an explanatory note indicating "activate the diet option" is written and a selection field RS52 in which an explanatory note indicating "inactivate the diet option" is written are set. The selection fields RS51 and RS52 are selection fields, only one of which is selectable.

Note that, when the selection field RS51 is selected, a standard diet program, for example, a diet program for attaining a reduction of 1% a month based on information input in the setting screen RS3 shown in FIG. 8 is created by the measurement information management program. On the other hand, when the selection field RS52 is selected, a diet program for maintaining the present weight is created.

On the screens RS1 to RS5 concerning the account registration, after setting the present weight of the user, the user is caused to select a physical activity level of the user on the setting screen RS4 immediately before setting whether the diet program is activated on the selection screen RS5. Consequently, after being caused to recognize physical information and a physical activity level (in other words, a life style) of the user, the user is caused to select whether the user carries out diet. Therefore, it is possible to allow the user to easily select the selection field RS51 for activating the diet program.

Even if the user does not set detailed items, when the user sets relatively simple items, a provisional diet program is created. Therefore, it is possible to save the labor of the user.

Note that, after the display of the selection screen RS5, although not shown in the figure, the display control unit 362 causes the display unit 31 to display a screen for executing pairing with the measuring apparatus 2 and a guidance screen for introducing a diet program. When the introduction by the guidance screen ends, the main screen MS is displayed.

Main Screen

FIGS. 12 to 32 are diagrams respectively showing examples of the main screen MS and detail screens.

Figure 12:
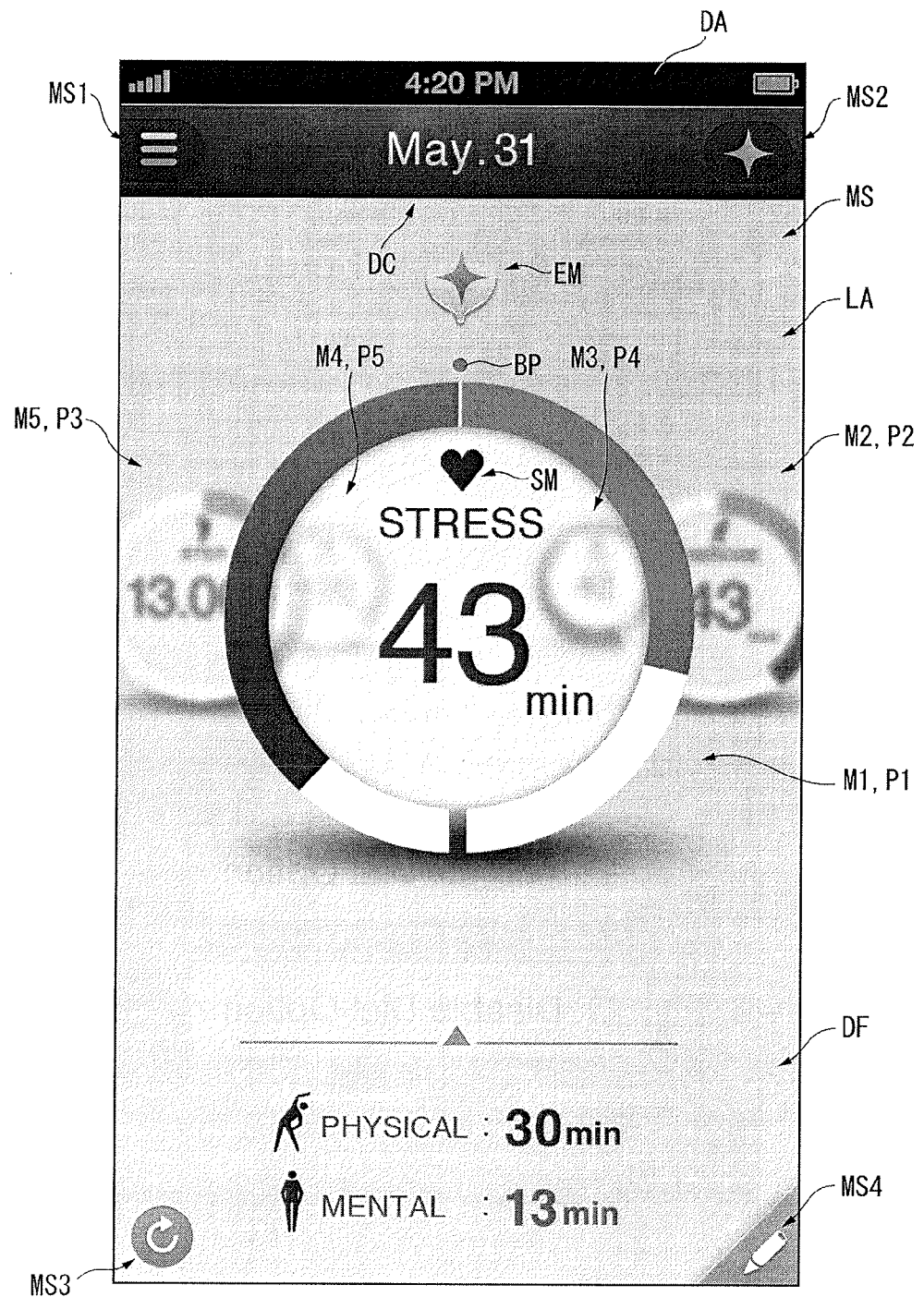
FIG. 12 is a diagram showing a main screen in the embodiment.

After any one of the selection fields RS51 and RS52 is selected on the selection screen RS5, when the forward key FK is entered or when login is performed from the login screen LS, the main screen MS shown in FIG. 12 is displayed.

The main screen MS is a screen indicating the mind and the behavior of the user. Specifically, on the main screen MS, a meter arrangement area LA where meters M1 to M5, which are doughnut graphs indicating the mind and the behavior of the user, are arranged, and a detail display area DF of the items are set. Besides, at the four corners of the main screen MS, transition keys MS1 and MS2, an update key MS3, and an editing key MS4 are respectively set. In substantially the upper center of the main screen MS, a date display area DC in which a date or a period of data displayed on screens is displayed is set.

The transition key MS1 arranged at the upper left of the main screen MS is a key for transition to a screen for displaying and editing a detailed profile of the user.

The transition key MS2 arranged at the upper right is a key for transition to an event check screen EV (see FIGS. 37 to 39) explained below.

The update key MS3 arranged at the lower left is a key for receiving measurement information from the measuring apparatus 2 and updating measurement information stored in the storing unit 35 and display contents of the main screen MS.

The editing key MS4 arranged at the lower right is a key for transition to an input screen ED (see FIGS. 34 to 36) explained below.

The meter arrangement area LA is equivalent to the graph arrangement area according to the invention. In the meter arrangement area LA, the meters M1 to M5 respectively indicating an excitement time, an exercise time, a sleep time, intake/consumed calories, and the number of steps of the user are set.

Specifically, in the meter arrangement area LA, the meters M1 to M5 are respectively arranged at equal intervals on an imaginary circle centering on a predetermined position in the depth direction of the main screen MS. The meter in a closest position viewed from the diameter direction of the imaginary circle is displayed large. For example, in FIG. 12, a stress meter M1 indicating an excited state of the user is displayed large. An exercise meter M2 indicating an exercise time, a sleep meter M3 indicating a sleep time, a calorie meter M4 indicating intake/consumed calories, and a number-of-steps meter M5 indicating the number of steps are arranged counterclockwise from the stress meter M1. Note that the array of the meters is not limited to the array explained above and can be changed as appropriate.

Note that, in the example shown in FIG. 12, the stress meter M1 is arranged in the center of the meter arrangement area LA. The exercise meter M2 and the number-of-steps meter MS are respectively arranged adjacent to the right side and the left side of the stress meter M1. The sleep meter M3 and the calorie meter M4 are arranged between the meters M2 and M5.

In other words, the meter M1, which is a meter (a first meter) located in a first position P1 closest to the user's side in the depth direction of the meter arrangement area LA, is displayed largest. The meters M2 and M5, which are meters (second meters) located in a second position P2 and a third position P3 further on the depth side than the first position P1, are respectively displayed smaller than the meter M1. Further, the meters M3 and M4, which are meters (third meters) located in a fourth position P4 and a fifth position P5 further on the depth side than the second position P2, are displayed smaller than the meters M2 and M5.

The meters M2 to M5 are displayed in colors lighter than a color of the meter M1 and at transmittance and transparency higher than the transmittance and the transparency of the meter M1. Specifically, the meter M1 located in the first position P1 is clearly displayed in a dark color and at low transmittance and low transparency. On the other hand, the meters M2 to M5 located in the second position P2 to the fifth position P5 further on the depth side than the first position P1 are hazily displayed in light colors and at high transmittance and high transparency. Note that the light colors indicate colors having gradations close to white. The dark color indicates a color having gradation close to black. The high transmittance and the high transparency indicate a state in which the meters are hazily seen. The low transmittance and the low transparency indicate a state in which the meters are clearly seen.

The positions P1 to P5 are explained. When the screen is viewed in a plane, the third position P3 is a position on the opposite side of the second position P2 with respect to the first position P1. The fifth position P5 is a position on the opposite side of the fourth position P4 with respect to the first position P1. That is, in the example shown in FIG. 12, the meter M1 is arranged in the first position P1, the meter M2 is arranged in the second position P2, the meter M5 is arranged in the third position P3, the meter M3 is arranged in the fourth position P4, and the meter M4 is arranged in the fifth position P5.

Display sizes of the meters in the positions P1 to P5 are in a relation of the first position P1>the second position P2 and the third position P3>the fourth position P4 and the fifth position P5. The display sizes of the meters in the second position P2 and the third position P3 are the same. The display sizes of the meters in the fourth position P4 and the fifth position P5 are the same. The same applies to the depths of the colors, the transmittances, and the transparencies of the meters in the positions P1 to P5. The meter in the first position P1 is displayed to be most easily visually recognized. The meters in the second position P2 and the third position P3 are displayed to be more easily visually recognized than the meters in the fourth position P4 and the fifth position P5.

With such a configuration, on the main screen MS, although not only the first meter but also the second meter and the third meter located further on the inner side than the first position P1 are displayed, the visibility of the first meter is not affected. Therefore, even if a display area of the main screen MS is small, all the meters M1 to M5 can be checked at a time. In this case, the second meter and the third meter located on the inner side are displayed in light colors compared with the first meter, the user can gaze the first meter. The meter M1 and the meters M2 to M5 are displayed with transmittance and transparency varied. By displaying the meters in this way, it is possible to provide a screen on which the meter M1 can be easily visually recognized, although a plurality of meters are displayed.

An overlapping area of the second meter and the first meter is smaller than an overlapping area of the third meter and the first meter. Consequently, information of the meters in the second position P2 and the third position P3 is displayed at higher visibility than the meters in the fourth position P4 and the fifth position P5. Therefore, it is possible to allow the user to easily check overviews of the meters in the second position P2 and the third position P3 while checking the first meter.

Note that display forms of the meters are not limited to the display forms explained above. The display sizes of the meters in the first position P1 to the fifth position P5 may be the same or may be different from one another. For example, the display sizes of the meters in the second position P2 and the third position P3 may be different from each other. The display sizes of the meters in the fourth position P4 and the fifth position P5 may be different from each other.

Further, the depths of the colors, the transmittances, and the transparencies of the meters in the first position P1 to the fifth position P5 may be the same or may be different from one another. For example, the depths of the colors, the transmittances, and the transparencies of the meters in the second position P2 and the third position P3 may be different from each other. The depths of the colors, the transmittances, and the transparences of the meters in the fourth position P4 and the fifth position P5 may be different from each other. Further, the depths of the colors, the transmittances, and the transparencies may be different between the meters in the second position P2 and the third position P3 and the meters in the fourth position P4 and the fifth position P5.

In the meter arrangement area LA where the meters M1 to M5 are arranged, when operation for flicking or dragging from the right side to the left side is performed, the second meter located on the right side with respect to the first meter moves to the first position P1. The meter located in the first position P1 moves to the third position P3 (i.e., a display position of the meter present in an operation direction of flicking operation or the like) located on the opposite side of the second position P2 with respect to the first position P1 when viewed in a plane. The meter present in the third position P3 before the operation moves to the fifth position P5 adjacent to the third position P3. The meter present in the fifth position P5 before the operation moves to the fourth position P4 adjacent to the fifth position P5. Further, the meter present in the fourth position P4 before the operation moves to the second position P2 adjacent to the fourth position P4. On the other hand, in the meter arrangement area LA, when operation for flicking or dragging from the left side to the right side is performed, the meters move oppositely to the movement explained above. The second meter on the left side moves to the first position P1.

Figure 13:
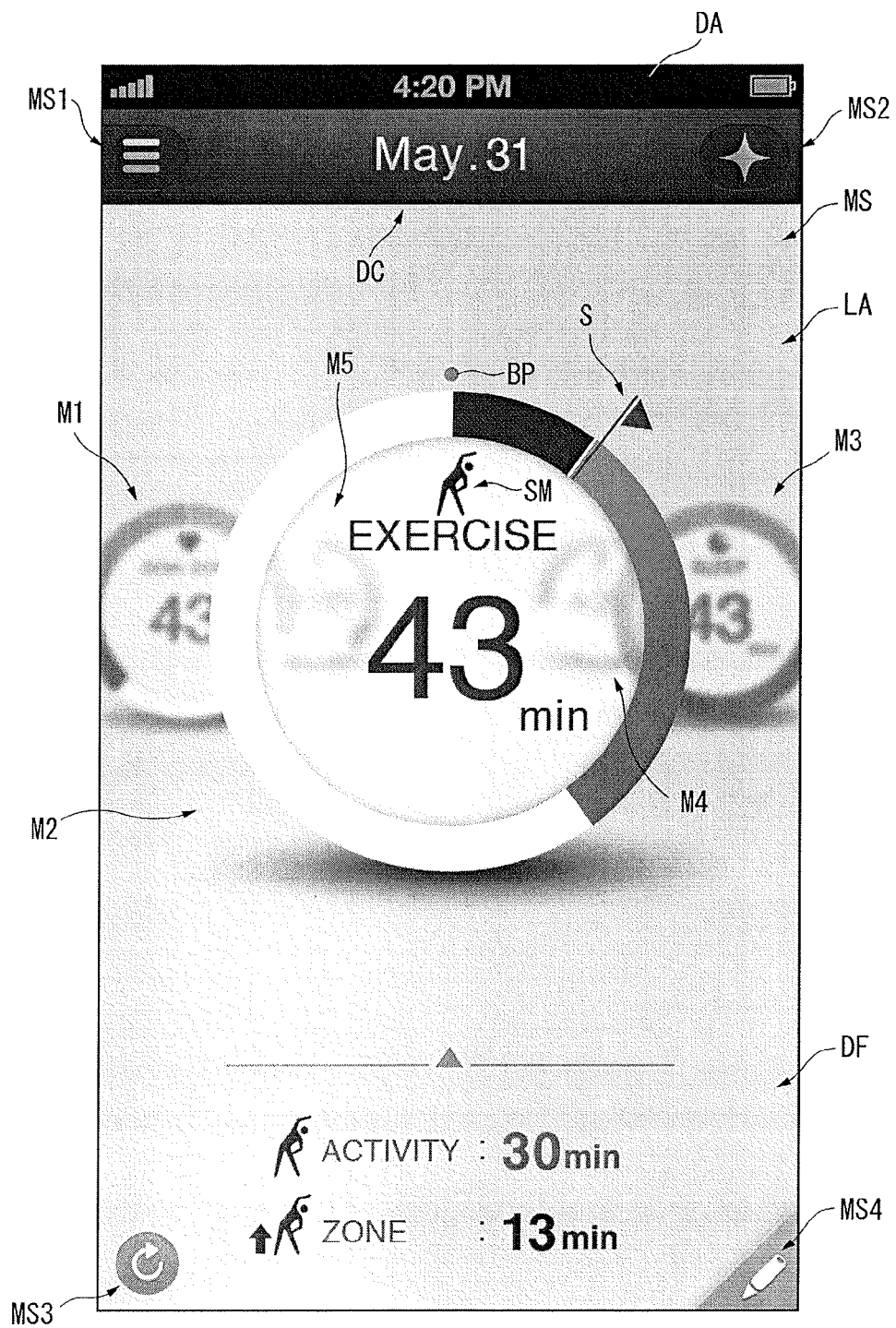
FIG. 13 is a diagram showing the main screen in the embodiment.
Figure 14:
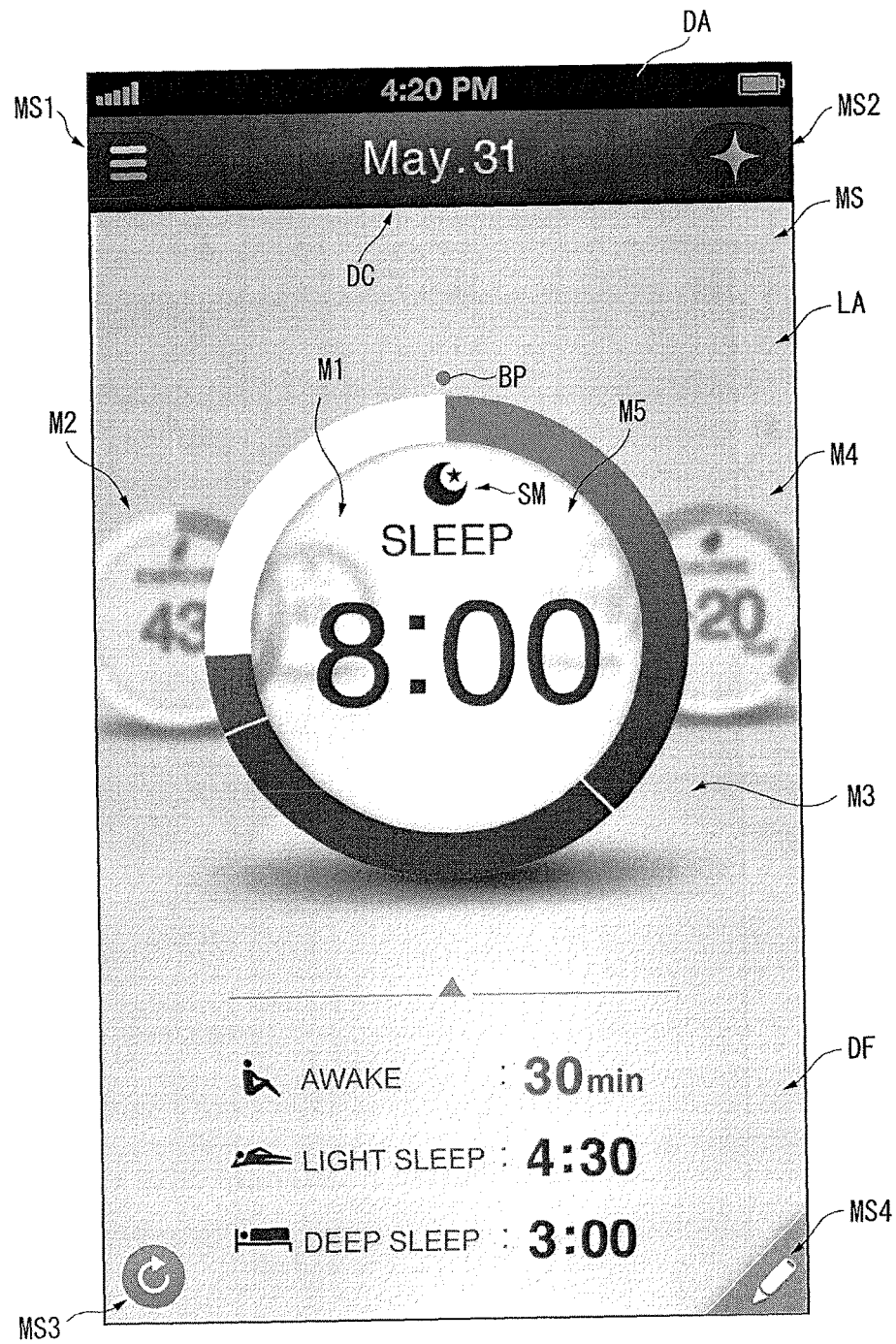
FIG. 14 is a diagram showing the main screen in the embodiment.
Figure 15:
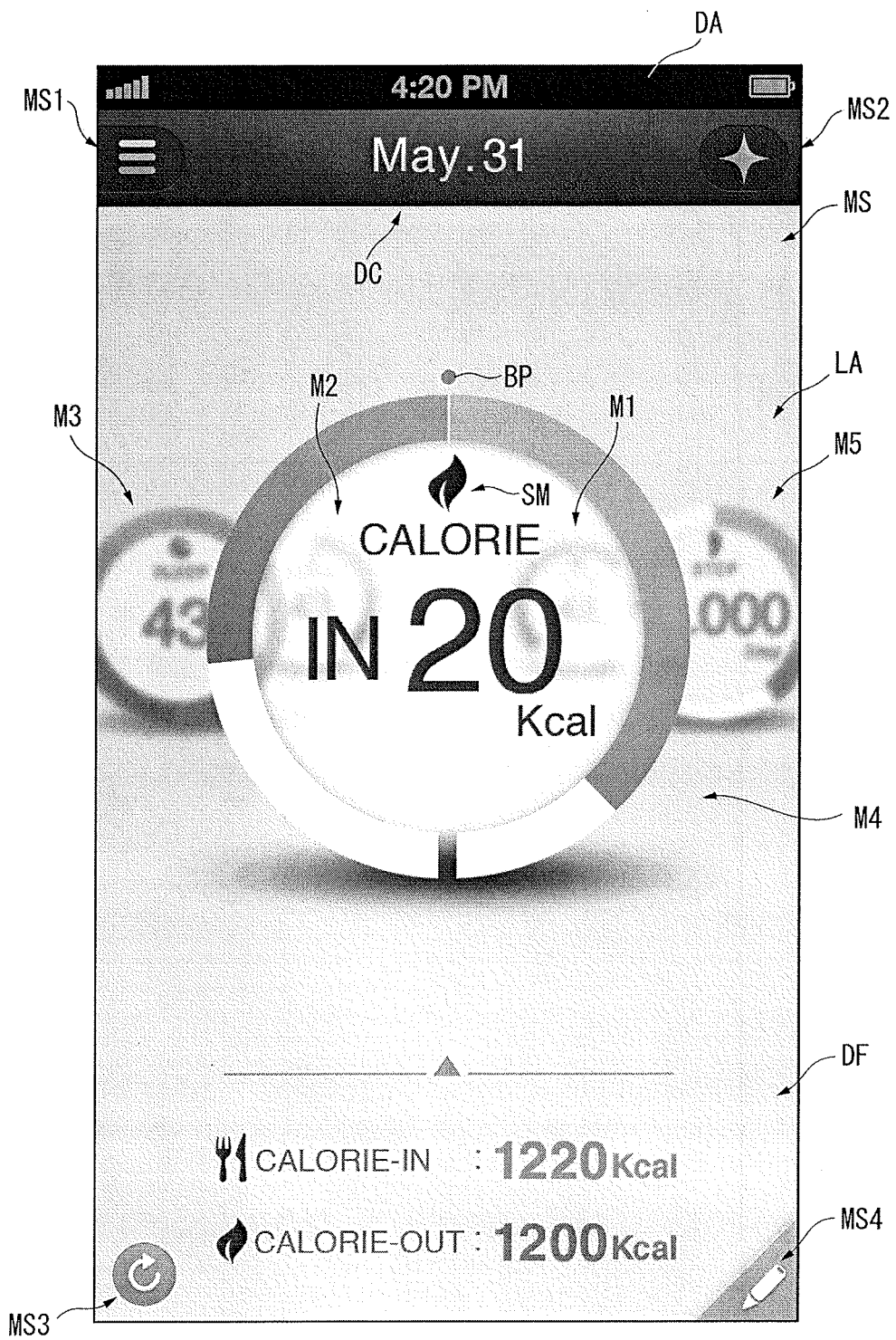
FIG. 15 is a diagram showing the main screen in the embodiment.
Figure 16:
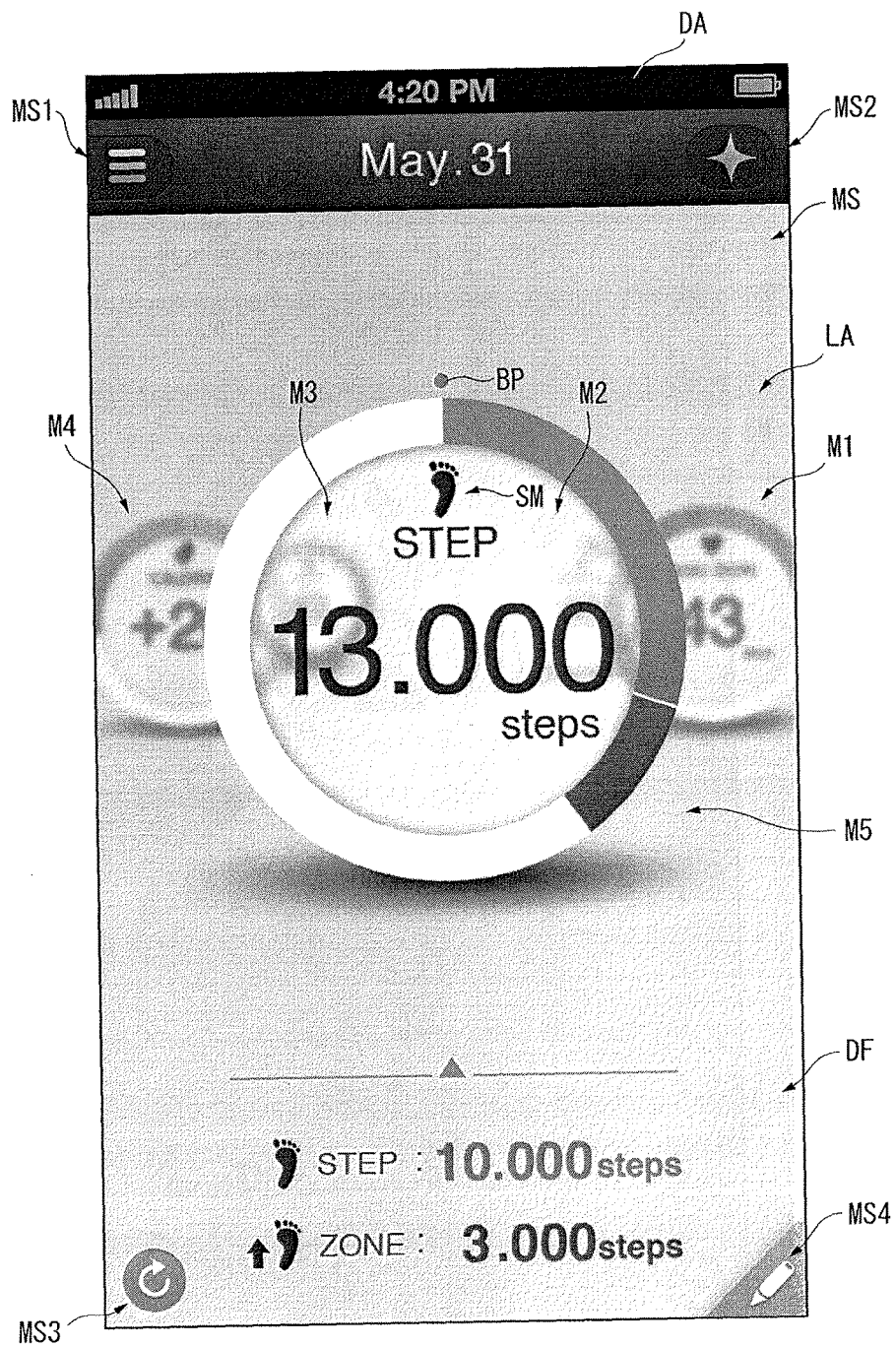
FIG. 16 is a diagram showing the main screen in the embodiment.

For example, in a state in which the main screen MS shown in FIG. 12 is displayed, when the operation for flicking or dragging from the right side to the left side (switching operation) is performed in the meter arrangement area LA, as shown in FIG. 13, the first meter is switched from the stress meter M1 to the exercise meter M2. That is, a type (an item) of information to be displayed is changed. Item information corresponding to the type is displayed. Every time the switching operation is performed, as shown in FIGS. 14 to 16, the first meter is switched to the sleep meter M3, the calorie meter M4, and the number-of-steps meter M5. When the same switching operation is further performed, the stress meter M1 is located in the first position P1.

On the other hand, in the state in which the main screen MS shown in FIG. 12 is displayed, when the switching operation from the left side to the right side is performed in the meter arrangement area LA, the first meter is switched in the opposite direction of the direction explained above. As shown in FIG. 16, the first meter is switched to the number-of-steps meter M5.

Note that, when the switching operation is quickly performed or performed to move in a long distance, the arrangement of the meters may be shifted by two meters. For example, when the operation is performed during the display of the main screen MS shown in FIG. 12, the sleep meter M3 may be moved to the first position P1.

When the first meter is switched by the operation, the meter displayed large is located in the first position P1. For example, when the switching operation from the right side to the left side is performed, the first meter and the second meter on the right side (the meter in the second position P2) move to the left side. The first meter is displayed small and the second meter is displayed large.

In this case, when the switching operation is suspended before the second meter is displayed larger than the first meter, the first meter and the second meter return to the original positions.

On the other hand, when the switching operation is continued until the second meter is displayed larger than the first meter, the first meter is switched to the second meter on the left side (the meter in the third position P3). The second meter is switched to the first meter.

During initial display of the main screen MS, the stress meter M1 is displayed in a state in which the stress meter M1 is located in the first position.

During the display of the login screen LS and the main screen MS, the meter located in the first position among the meters M1 to M5 can be set in advance. For example, when an application is started for the first time, a default meter may be displayed in the first position. After the completion of login processing explained below or when the user selects to continue a login state, a meter reflecting measurement information of the user may be displayed in the first position on the login screen LS.

A meter with updated information or a meter determined as being required to be notified to the user may be displayed in the first position. For example, when the user clears a goal, a meter corresponding to the goal clear may be displayed in the first position.

Note that the display of the main screen MS by the display control unit 362 is carried out after processing explained below is performed in advance.

That is, in the information terminal 3, first, the main control unit 361 acquires, with the communication control unit 363 and the communication unit 33, the measurement information from the measuring apparatus 2 or the server 5. The calculating unit 365 calculates and generates, on the basis of the measurement information, user information, and the like, various kinds of information (item information) indicated by the meters M1 to M5. Thereafter, the display control unit 362 generates a plurality of meters M1 to M5 on the basis of the generated information and arranges the meters M1 to M5 in the meter arrangement area LA of the main screen MS. In this case, the meters M1 to M5 are arranged such that a part of the meters in the second position and the third position overlap the meters in the fourth position and the fifth position and a part of the meter in the first position overlaps the meters in the second position and the third position. Consequently, the main screen MS is generated and displayed.

The main screen MS including the meters M1 to M5 is displayed in this way. Consequently, it is possible to cause the user to objectively observe the life of the user from a plurality of viewpoints. It is possible make use of this for improvement of the quality of the life of the user.

Display of an Excitement Time

The display of an excitement time is explained.

When the user operates the main screen MS and moves the stress meter M1 to the first position, the main screen MS shown in FIG. 12 is displayed.

The stress meter M1 on the main screen MS is a balance meter indicating an excitement time during exercise and an excitement time during non-exercise and is a doughnut graph, the lower end of a circle of which is divided. The stress meter M1 indicates an excitement time during exercise using an extension amount in the counter clockwise direction from a reference point BP at the upper end and indicates an excitement time during non-exercise using an extension amount in the clockwise direction from the reference point BP.

In the stress meter M1, the excitement time during exercise is rendered in a dark blue color and the excitement time during non-exercise is rendered in a light blue color. That is, in the stress meter M1, the excitement time during exercise and the excitement time during non-exercise are displayed to be identifiable by shadings and gradations of similar colors. In the center of the stress meter M1, a total value of the excitement time during exercise and the excitement time during non-exercise in the day is displayed.

In the detail display area DF, the excitement time during exercise (time displayed after a word "PHYSICAL") and the excitement time during non-exercise (time displayed after a word "MENTAL") are set.

Display contents of the stress meter M1 and the detail display area DF are generated and displayed by the display control unit 362 on the basis of a calculation result by the excitement-time calculating unit 3651.

Figure 17:
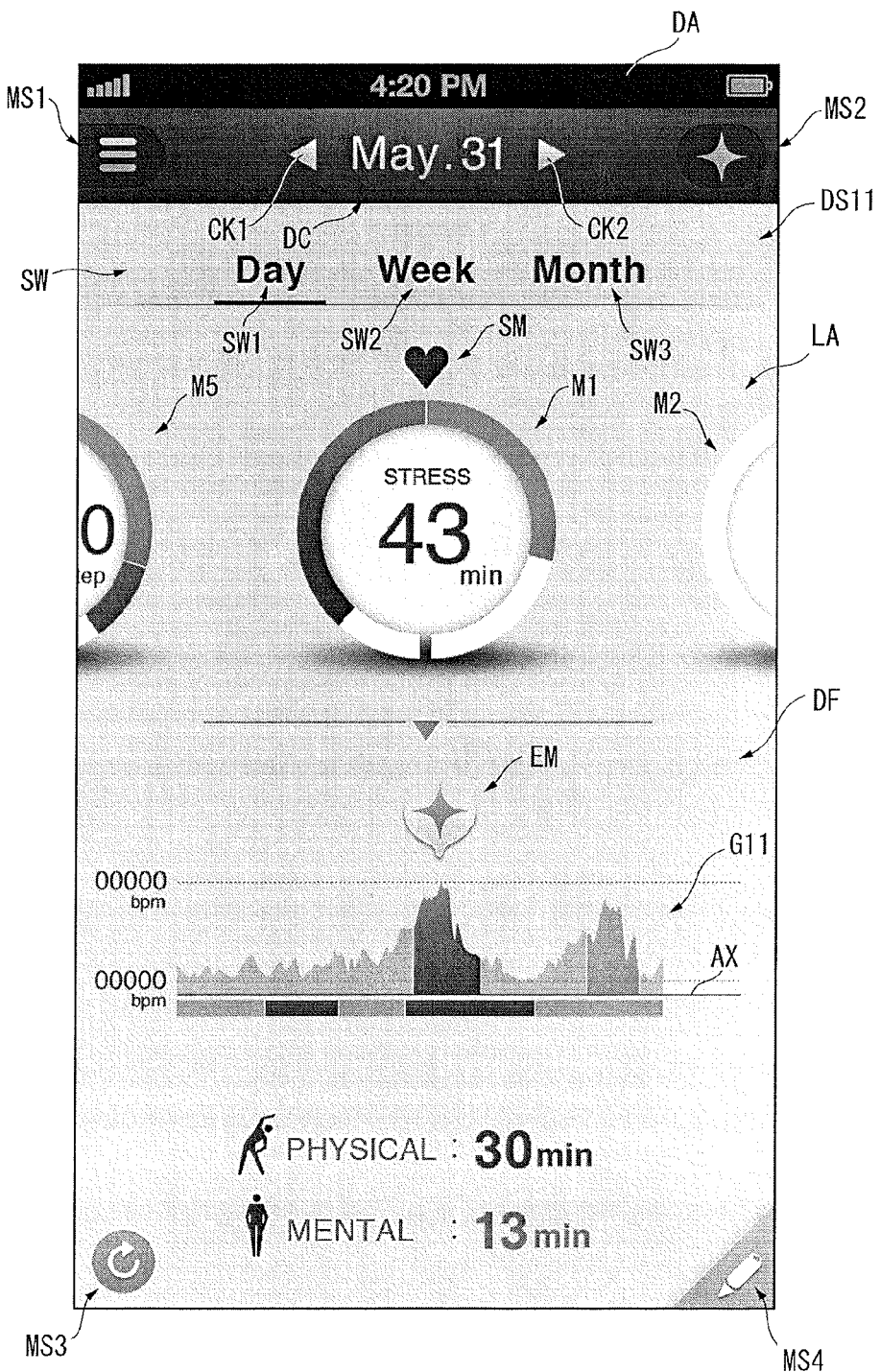
FIG. 17 is a diagram showing a day detail screen concerning an excitement time in the embodiment.

On the main screen MS shown in FIG. 12, when the detail display area DF is tapped or clicked, a day detail screen DS11 concerning an excitement time shown in FIG. 17 is displayed. The day detail screen DS11 is a detail screen in day units concerning an excitement time. On the day detail screen DS11, a display switching field SW, the meter arrangement area LA, and the detail display area DF are arranged.

Specifically, on the day detail screen DS11, the meter arrangement area LA is reduced, the display switching field SW is set on the upper side of the meter arrangement area LA, and the detail display area DF is expanded to the upper side. Further, on the day detail screen DS11, cursor keys CK1 and CK2 are set on the left and right of the date display area DC arranged between the transition keys MS1 and MS2 to display the present date. With such display, it is possible to provide the user with detailed information according to necessity.

When the day detail screen DS11 is displayed, in the meter arrangement area LA, the number-of-steps meter M5 and the exercise meter M2, which are the left and right second meters, move to further outer side and the meters M3 and M4 move to the outside of the display area. In this case, transmittances set in the meters M5 and M2 are released. Further, the stress meter M1 is reduced to size same as the size of the meters M5 and M2 and is arranged between the meters M5 and M2. A symbol mark (a heart symbol mark, which is a symbol mark of the stress meter M1) SM arranged in the meter M1 is moved to a position on the outer side and the upper side of the meter M1. With such display, even if the stress meter M1 is reduced, a number in the meter M1 can be displayed larger.

In the center of the stress meter M1, a total value of an excitement time during exercise and an excitement time during non-exercise on a date of display of data is displayed.

In the detail display area DF, the excitement time during exercise and the excitement time during non-exercise are displayed. Besides, above the excitement time during exercise and the excitement time during non-exercise, a graph G11 is displayed in which a time axis AX from the midnight of a date displayed in the date display area DC is set and changes in a pulse rate are shown on the time axis AX. In the graph G11, a range of times determined as the excitement time during exercise and the excitement time during non-exercise is represented by shadings of similar colors (i.e., the dark blue color and the light blue color) same as those in the stress meter M1. In a graph area where the graph G11 is displayed, there are two places where "00000 bpm" is rendered. Of the two places, in the place on the lower side, a lower limit value of a measurement range by the measuring apparatus 2 is set and, in the place on the upper side, a maximum in the displayed graph G11 is set.

During the display of the day detail screen DS11, when the cursor key CK1 facing the left side is entered, the day detail screen DS11 of the preceding day is displayed. When the cursor key CK1 is further entered, the day detail screen DS11 of the preceding day is further displayed. When the cursor key CK2 facing the right side is entered, the day detail screen DS11 of the following day is displayed. With such display, it is possible to easily grasp a stress status of the user in one day.

In the display switching field SW, areas SW1 to SW3 inscribed as "Day", "Week", and "Month" are set. The areas SW1 to SW3 respectively receive operation for switching the day detail screen DS11 in day units, a week detail screen DS12 (see FIG. 18), which is a detail screen in nearest week units, and a month detail screen DS13 (see FIG. 19), which is a detail screen in nearest month units. Note that, in the display switching field SW, a mark indicating a type of a currently displayed detail screen is set. That is, when the day detail screen DS11 is displayed, an image like an underline is set in the area SW1. When the week detail screen DS12 is displayed, an underline is set in the area SW2. Further, when the month detail screen DS13 is displayed, an underline is set in the area SW3.

Figure 18:
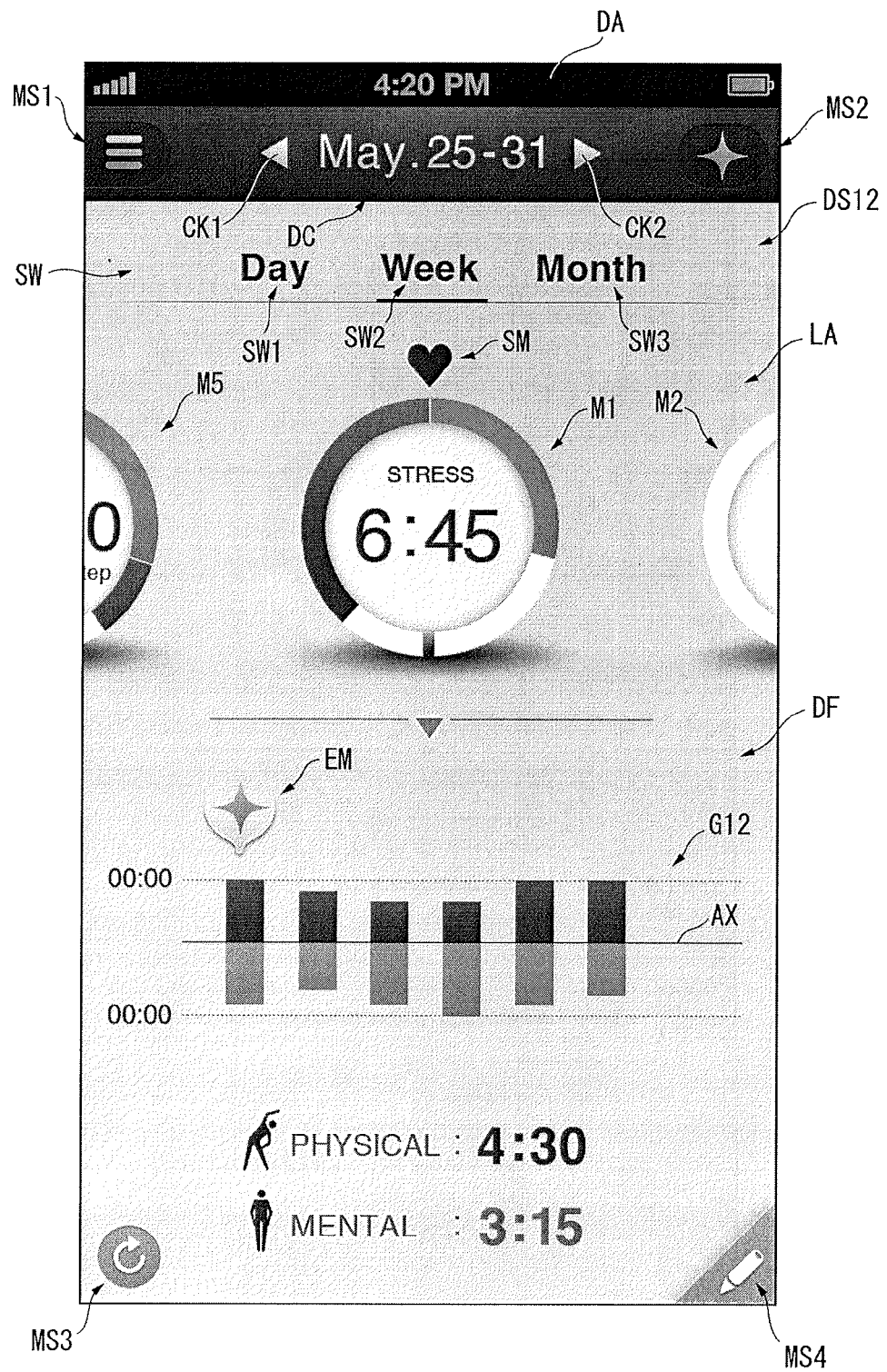
FIG. 18 is a diagram showing a week detail screen concerning the excitement time in the embodiment.

When the area SW2 inscribed as "Week" is entered, the week detail screen DS12 shown in FIG. 18 is displayed. The week detail screen DS12 is a detail screen of the week concerning an excitement time. On the week detail screen DS12, the display switching field SW, the meter arrangement area LA, and the detail display area DF are set.

The stress meter M1 arranged in the meter arrangement area LA is a meter indicating an excitement time during exercise and an excitement time during non-exercise for the nearest one week (seven days). In the center of the meter M1, a total value of the excitement time during exercise and the excitement time during non-exercise for the nearest one week is displayed.

In the detail display area DF, instead of the graph G11, a graph G12 is displayed in which an excitement time during exercise for each day in the nearest one week is indicated by an extension amount to the upper side from the time axis AX in a period displayed in the date display area DC and an excitement time during non-exercise for each day in the nearest one week is indicated by an extension amount to the lower side from the time axis AX. In the graph G12, a graph indicating the excitement time during exercise and the excitement time during non-exercise of the day is set in a position on the rightmost side. Note that, in a graph area where the graph G12 is displayed, there are two places where "00:00" is rendered. Of the places, in the place on the lower side, a maximum of excitement times during non-exercise in the displayed graph G12 is set. In the place on the upper side, a maximum of excitement times during exercise in the graph G12 is set.

An excitement time during exercise and an excitement time during non-exercise displayed in the detail display area DF are total values of excitement times during exercise and excitement times during non-exercise for each day in the nearest one week.

During the display of the week detail screen DS12, when the cursor key CK1 facing the left side is entered, the week detail screen DS12 of a week starting from the nearest Sunday or Monday is displayed. When the cursor key CK1 is further entered, the week detail screen DS12 of the preceding week is further displayed. When the cursor key CK2 facing the right side is entered, the week detail screen DS12 of the following week is displayed. With such display, it is possible to provide the user with an opportunity for, while grasping a stress state of the user for the nearest one week, reviewing the week.

Figure 19:
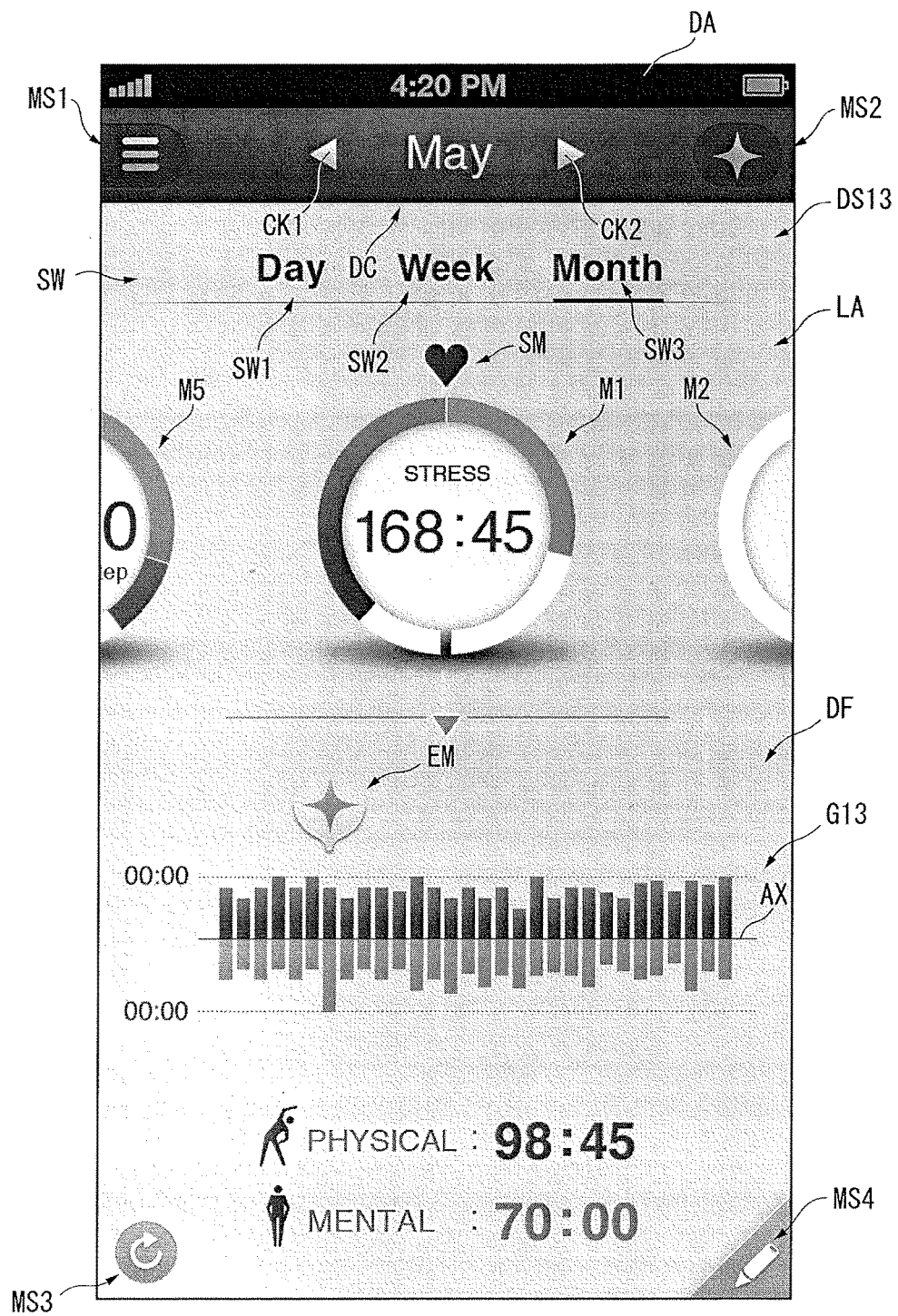
FIG. 19 is a diagram showing a month detail screen concerning the excitement time in the embodiment.

When the area SW3 inscribed as "Month" is entered, the month detail screen DS13 shown in FIG. 19 is displayed. The month detail screen DS13 is a detail screen of the month concerning an excitement time. On the month detail screen DS13, the display switching field SW, the meter arrangement area LA, and the detail display area DF are set.

The stress meter M1 arranged in the meter arrangement area LA is a meter indicating an excitement time during exercise and an excitement time during non-exercise for the nearest one month (thirty days or thirty-one days). In the center of the meter M1, a total value of the excitement time during exercise and the excitement time during non-exercise for the one month is displayed. With such display, it is possible to grasp a stress balance in each day of the nearest one month, that is, a balance between physical stress and mental stress while comparing the physical stress and the mental stress for each day.

In the detail display area DF, like the graph G12, a graph G13 is displayed that indicates an excitement time during exercise for each day in the nearest one month using an extension amount to the upper side from the time axis AX in a period displayed in the date display area DC and indicates an excitement time during non-exercise for each day in the nearest one month using an extension amount to the lower side from the time axis AX. In the graph G13, a graph indicating the excitement time during exercise and the excitement time during non-exercise of the day is set in a position on the rightmost side. Values set in two places where "00:00" is rendered in a graph area where the graph G13 is displayed are the same as the values in the graph area where the graph G12 is displayed.

Note that, when the week detail screen DS12 is switched to the month detail screen DS13, after the graph G12 is collected on the right side, an animation in which a graph indicating excitement times during exercise and excitement times during non-exercise in the remaining days is set is displayed from the left side of a free space. This also applies when week detail screens DS22, DS32, DS42, and DS52 are switched to month detail screens DS23, DS33, DS43, and DS53.

An excitement time during exercise and an excitement time during non-exercise displayed in the detail display area DF are total values of excitement times during exercise and excitement times during non-exercise for each day in the nearest one month.

During the display of the month detail screen DS13, when the cursor key CK1 facing the left side is entered, the month detail screen DS13 of a month starting from the nearest first day (a first day of a month) is displayed. When the cursor key CK1 is further entered, the month detail screen DS13 of the preceding month is displayed. When the cursor key CK2 facing the right side is entered, the month detail screen DS13 of the following month is displayed.

Note that, in a state in which any one of the day detail screen DS11, the week detail screen DS12, and the month detail screen DS13 is displayed, when the information terminal 3 is tilted sideways, a graph corresponding to the screen is enlarged and displayed.

Figure 20:
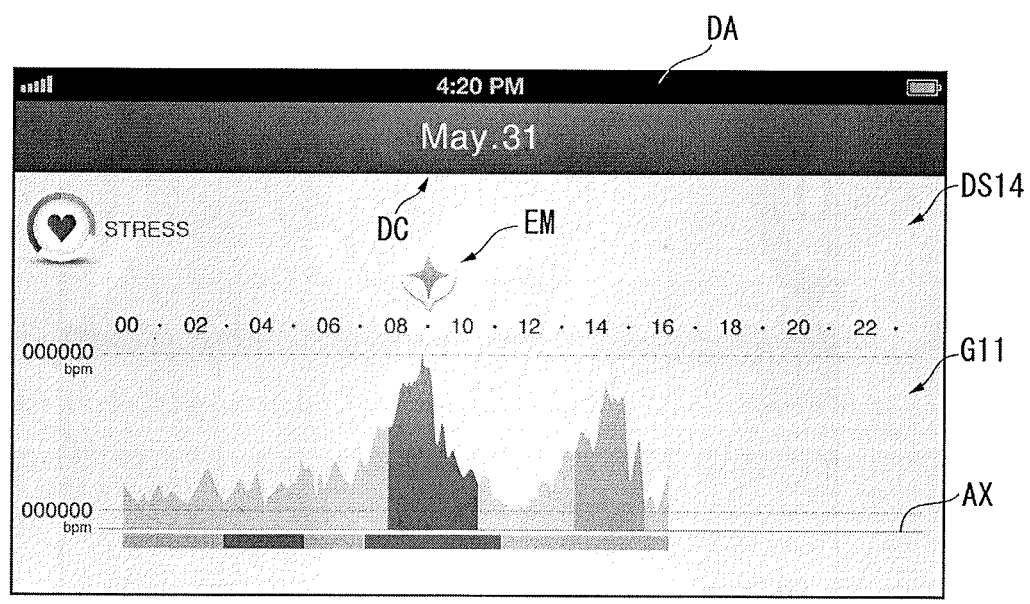
FIG. 20 is a diagram showing an information terminal in the embodiment placed sideways.

For example, during the display of the day detail screen DS11, when the information terminal 3 is tilted sideways, as shown in FIG. 20, a screen DS14 in which the graph G11 included in the day detail screen DS11 is enlarged upward and downward and to the left and right is displayed. With such display, even if a screen of the information terminal 3 is small, it is possible to easily check more detailed changes in time series.

Display of an Exercise Time

Display of an exercise time is explained.

When the user operates the main screen MS and moves the exercise meter M2 to the first position, the main screen MS shown in FIG. 13 is displayed.

The exercise meter M2 is a doughnut graph indicating an exercise time (a normal exercise time and an in-zone exercise time) using an extension amount in the clockwise direction starting from the reference point BP at the upper end. In the exercise meter M2, the in-zone exercise time is set on a side close to the start point. In this case, the normal exercise time is rendered in a pink color and the in-zone exercise time is rendered in a purple color. That is, in the exercise meter M2, as in the stress meter M1, the exercise times are displayed to be identifiable by shadings and gradations of similar colors.

In the exercise meter M2, a target value set by the diet program is indicated by a straight line S extending in the diameter direction of the meter M2. In the center of the exercise meter M2, a total value of exercise times of the day is displayed. With such display, the user can check the present exercise total time, the in-zone exercise time, and a degree of attainment of a goal at a time and intuitively grasp effects of exercise performed by the user.

On the main screen MS on which the exercise meter M2 is located in the first position, in the detail display area DF, a normal exercise time (time displayed after a word "ACTIVITY") and an in-zone exercise time (time displayed after a word "ZONE") are displayed. With such a display, it is possible to check a specific implementation status.

Figure 21:
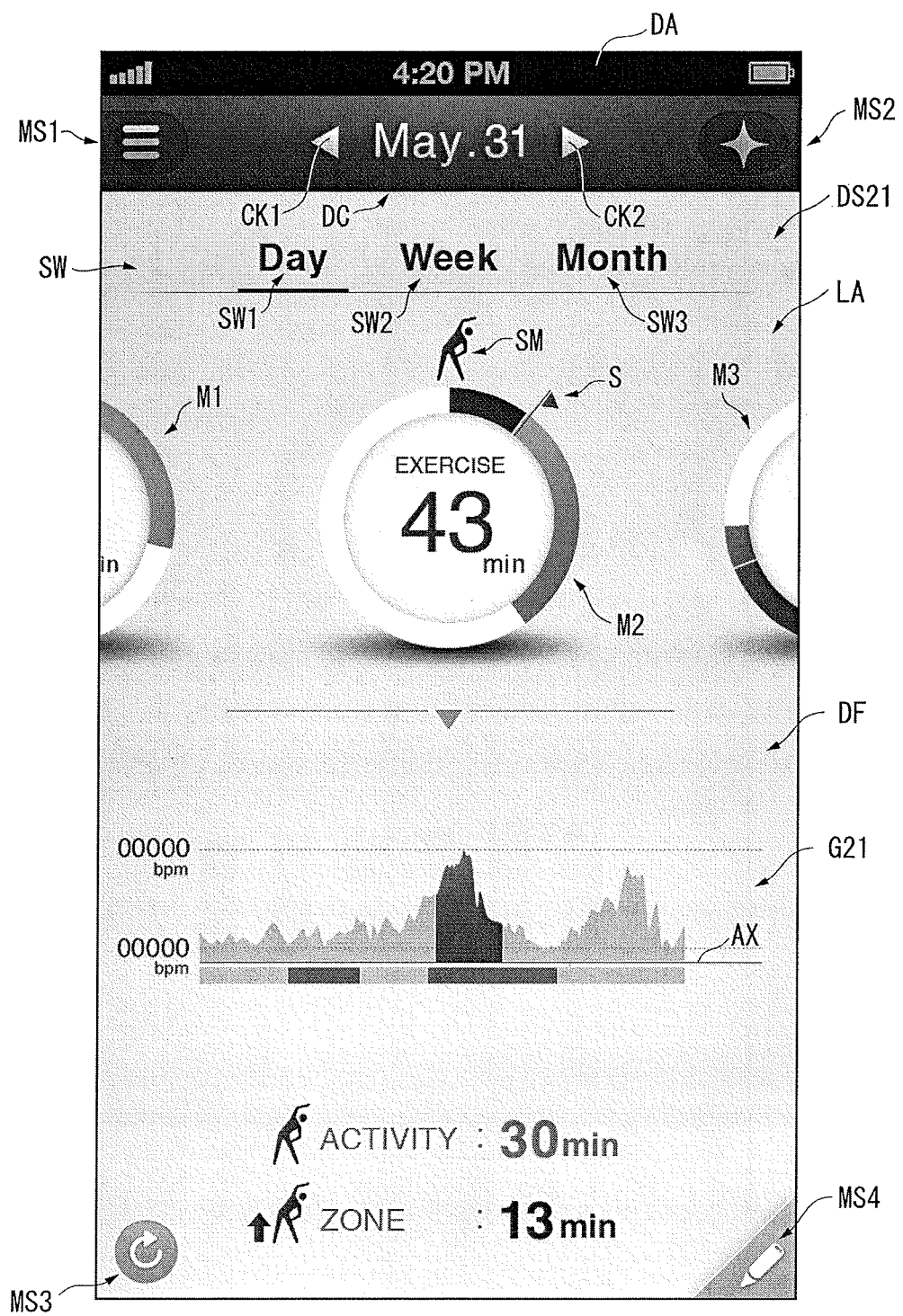
FIG. 21 is a diagram showing a day detail screen concerning an exercise time in the embodiment.

On the main screen MS shown in FIG. 13, when the detail display area DF is tapped or clicked, a day detail screen DS21 concerning an exercise time shown in FIG. 21 is displayed.

The day detail screen DS21 is a detail screen in day units concerning an exercise time. On the day detail screen DS21, as on the day detail screen DS11, the display switching field SW, the meter arrangement area LA, and the detail display area DF are arranged. With such display, it is possible to provide the user with detailed information according to necessity.

When the day detail screen DS21 is displayed, in the meter arrangement area LA, as on the day detail screen DS11, the exercise meter M2 is reduced to size same as the size of the meters M1 and M3 located on the left and right of the exercise meter M2 and is arranged between the meters M1 and M3. The symbol mark SM arranged in the meter M2 is moved to a position on the outer side and the upper side of the meter M2. With such display, as explained above, even if the exercise meter M2 is reduced, it is possible to display a number in the meter M2 larger. In the center of the exercise meter M2, a total value of exercise times of the day is displayed.

In the detail display area DF, the normal exercise time and the in-zone exercise time are displayed. Further, above the normal exercise time and the in-zone exercise time, a graph G21 is displayed in which the time axis AX from the midnight of a date displayed in the date display area DC is set and changes in a pulse rate is shown on the time axis AX. In the graph, a range of times calculated as the normal exercise time and the in-zone exercise time is represented by shadings of similar colors same as those in the exercise meter M2. Values set in two places where "00000 bpm" is rendered in a graph area where the graph G21 is displayed are the same as the values in the graph area where the graph G11 is displayed.

During the display of the day detail screen DS21, when the cursor key CK1 facing the left side is entered, the day detail screen DS21 of the preceding day is displayed. When the cursor key CK1 is further entered, the day detail screen DS21 of the preceding day is further displayed. When the cursor key CK2 facing the right side is entered, the day detail screen DS21 of the following day is displayed. With such display, it is possible to easily grasp exercise in one day carried out by the user.

Figure 22:
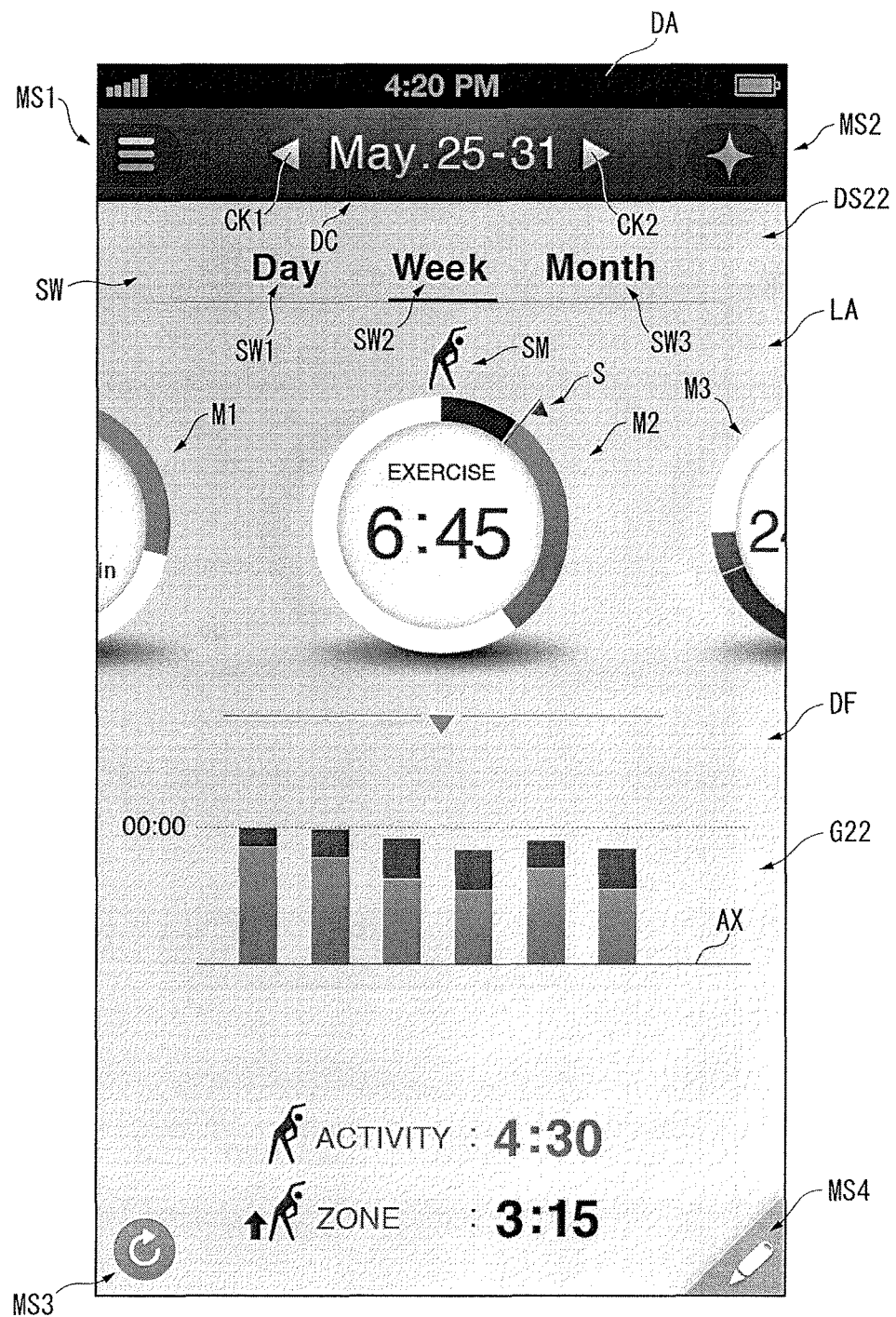
FIG. 22 is a diagram showing a week detail screen concerning the exercise time in the embodiment.

When the area SW2 in the display switching field SW is entered, the week detail screen DS22 shown in FIG. 22 is displayed. The week detail screen DS22 is a detail screen in week units concerning an exercise time. On the week detail screen DS22, the display switching field SW, the meter arrangement area LA, and the detail display area DF are set.

The exercise meter M2 arranged in the meter arrangement area LA is a meter indicating a total value of normal exercise times and a total value of in-zone exercise times for the nearest one week. A value displayed in the center of the meter M2 is a total value of exercise times for the nearest one week.

In the detail display area DF, instead of the graph G21, a graph G22 of a stacking type is displayed in which the time axis AX of a period displayed in the date display area DC is set and a normal exercise time and an in-zone exercise time are stacked for each day to the upper side from the time axis AX. In the graph G22, an exercise time of the day is shown in a position on the rightmost side. Note that, in a graph area where the graph G22 is displayed, there is a place where "00:00" is rendered. In the place, a maximum of total values (total values of normal exercise times and in-zone exercise times) of days indicated by the displayed graph G22 is set.

A normal exercise time and an in-zone exercise time displayed in the detail display area DF are total values of normal exercise times and in-zone exercise times for each day in the nearest one week.

During the display of the week detail screen DS22, when the cursor key CK1 facing the left side is entered, the week detail screen DS22 of a week starting from the nearest Sunday or Monday is displayed. When the cursor key CK1 is further entered, the week detail screen DS22 of the preceding week is displayed. When the cursor key CK2 facing the right side is entered, the week detail screen DS22 of the following week is displayed. With such display, it is possible to provide the user with an opportunity for, while grasping an amount of exercise carried out in nearest one week, reviewing the week. Since a balance between the in-zone exercise time and the other exercise times can be grasped, it is possible to intuitively grasp efficiency of exercise.

Figure 23:
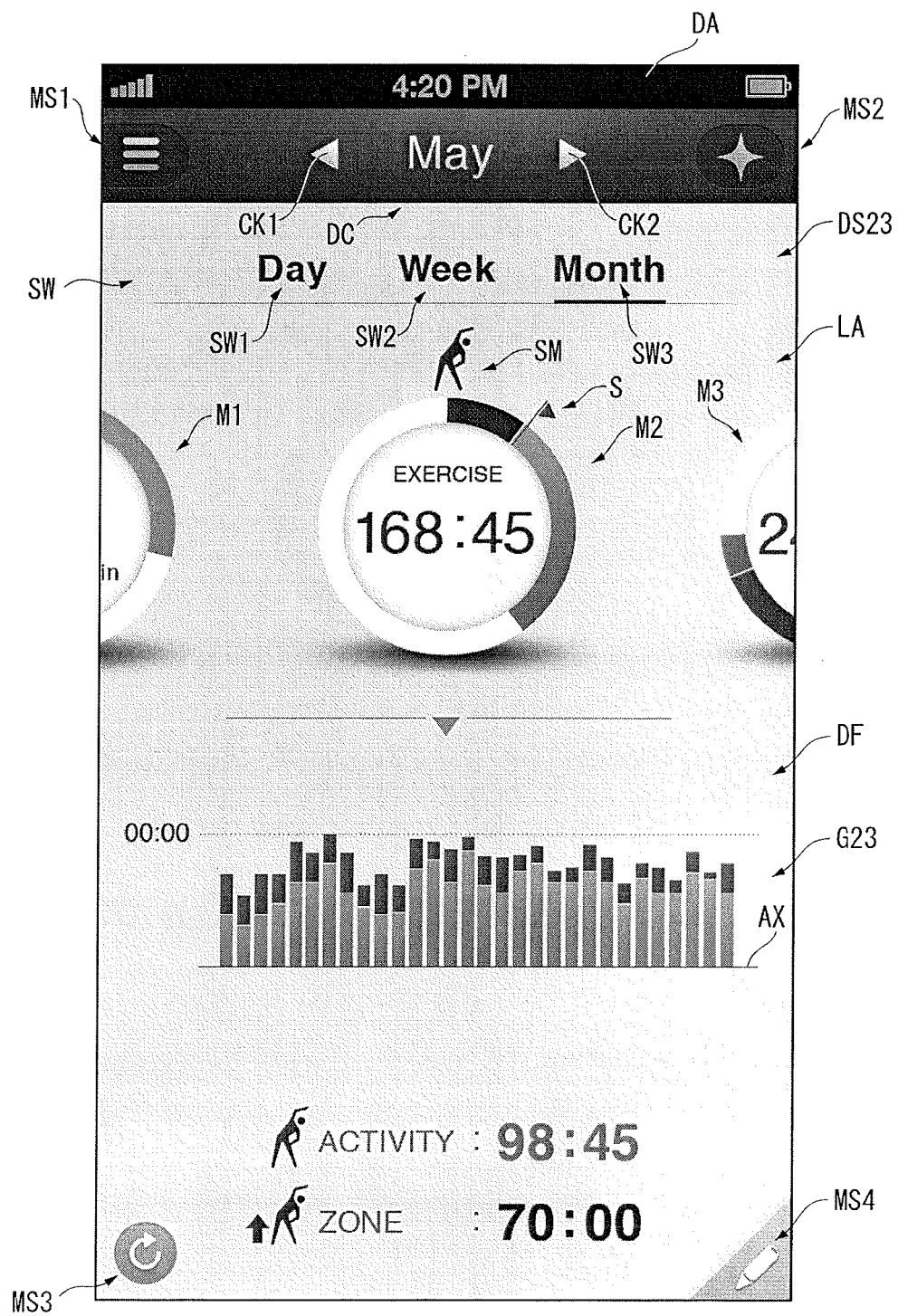
FIG. 23 is a diagram showing a month detail screen concerning the exercise time in the embodiment.

In a state in which any one of the day detail screen DS21 and the week detail screen DS22 is displayed, when the area SW3 is entered, a month detail screen DS23 shown in FIG. 23 is displayed. The month detail screen DS23 is a detail screen in month units concerning an exercise time. On the month detail screen DS23, the display switching field SW, the meter arrangement area LA, and the detail display area DF are set.

The exercise meter M2 arranged in the meter arrangement area LA is a meter indicating a normal exercise time and an in-zone exercise time for the nearest one month. In the center of the meter M2, a total value of exercise times for the nearest one month is displayed. With such display, it is possible to grasp kinds of exercise carried out in the nearest one month while comparing the kinds of exercise for each day.

In the detail display area DF, like the graph G22, a graph G23 of a stacking type is displayed in which the time axis AX of a period displayed in the date display area DC is set and a normal exercise time and an in-zone exercise time for each day in the nearest one month is indicated by an extension amount to the upper side from the time axis AX. In the graph G23, an exercise time of the day is shown in a position on the rightmost side. A value set in a place where "00:00" is rendered in a graph area where the graph G23 is displayed is the same as the value in the graph area where the graph G22 is displayed.

A normal exercise time and an in-zone exercise time displayed in the detail display area DF are total values of normal exercise times and in-zone exercise times for each day in the nearest one month.

During the display of the month detail screen DS23, when the cursor key CK1 facing the left side is entered, the month detail screen DS23 of a month starting from the nearest first day is displayed. When the cursor key CK1 is further entered, the month detail screen DS23 of the preceding month is displayed. When the cursor key CK2 facing the right side is entered, the month detail screen DS23 of the following month is displayed.

In a state in which any one of the detail screens DS21 to DS23 is displayed, when the information terminal 3 is tilted sideways, as explained above, a graph corresponding to the screen is enlarged and displayed. With such display, even if the screen of the information terminal 3 is small, it is possible to easily check more detailed changes in time series.

Display of a Sleep Time

Display of a sleep time is explained.

When the user operates the main screen MS and moves the sleep meter M3 to the first position, the main screen MS shown in FIG. 14 is displayed.

The sleep meter M3 is a doughnut graph indicating a sleep time (an awakening time, a light sleep time, and a deep sleep time) using an extension amount in the clockwise direction starting from the reference point BP at the upper end. In the sleep meter M3, the deep sleep time, the light sleep time, and the awakening time are set in order from a side close to the start point. In this case, the deep sleep time is rendered in a light blue color, the light sleep time is rendered in a deep blue color, and the awakening time is rendered in a purple color. That is, in the sleep meter M3, as in the meters M1 and M2, the sleep times are displayed to be identifiable by shadings and gradations of similar colors. In the center of the sleep meter M3, a total value of sleep times of the day is displayed. With such display, it is easy to check an overview of a state of sleep in the day.

On the main screen MS, in the detail display area DF, the deep sleep time (time displayed after a word "DEEP SLEEP"), the light sleep time (time displayed after a word "LIGHT SLEEP"), and the awakening time (time displayed after a word "AWAKE") are arranged in order from the bottom and displayed. Since detailed information is displayed in this way, it is possible to grasp a sleep state in the day as a specific numerical value.

Figure 24:
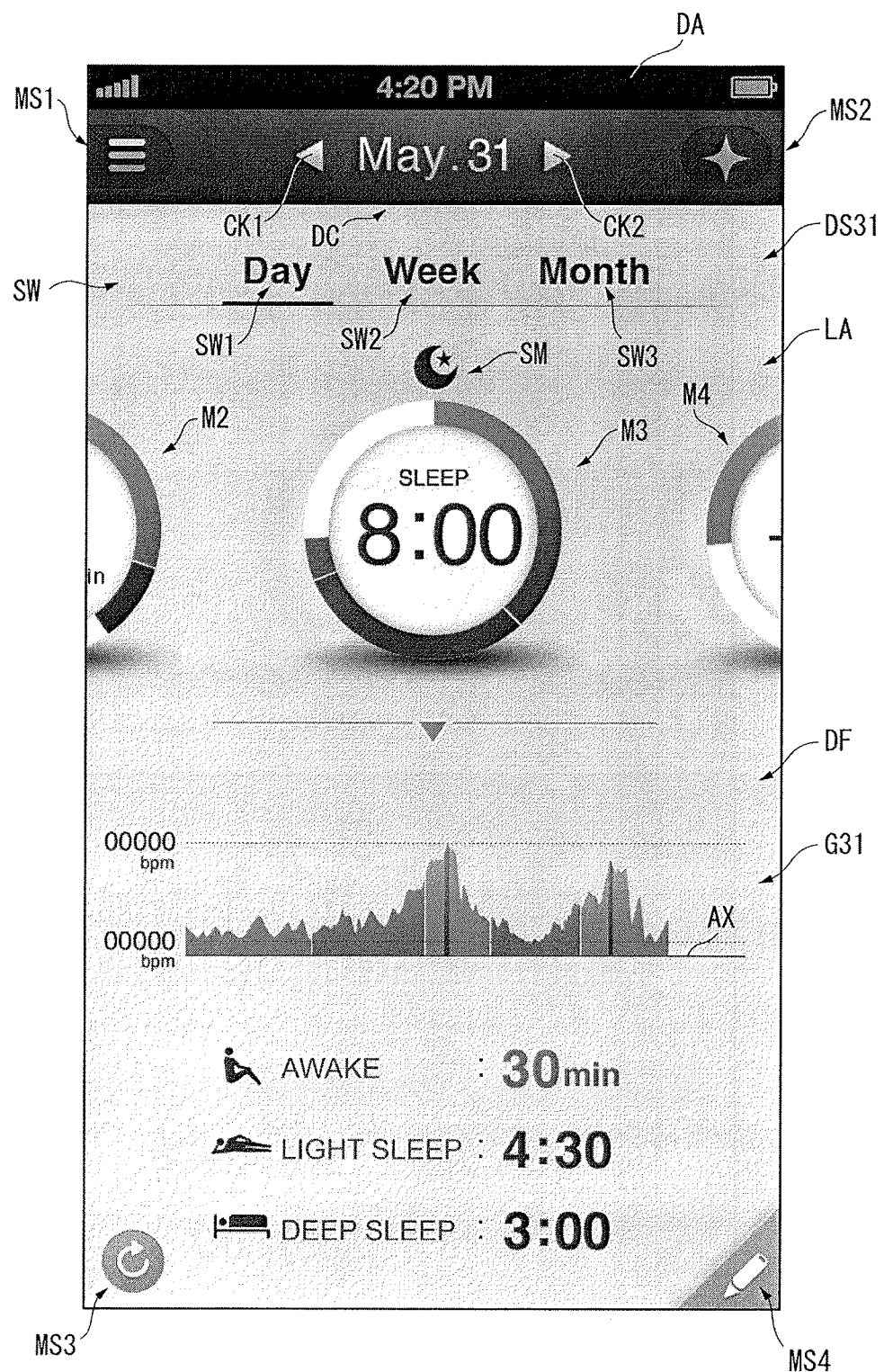
FIG. 24 is a diagram showing a day detail screen concerning a sleep time in the embodiment.

On the main screen MS shown in FIG. 14, when the detail display area DF is tapped or clicked, a day detail screen DS31 concerning a sleep time shown in FIG. 24 is displayed.

The day detail screen DS31 is a detail screen of the day concerning a sleep time. On the day detail screen DS31, as on the day detail screens DS11 and DS21, the display switching field SW, the meter arrangement area LA, and the detail display area DF are arranged.

When the day detail screen DS31 is displayed, in the meter arrangement area LA, as on the day detail screens DS11 and DS21, in a state in which the sleep meter M3 is reduced to size same as the size of the meters M2 and M4 located on the left and right of the sleep meter M3, the sleep meter M3 is arranged between the meters M2 and M4. The symbol mark SM arranged in the meter M3 is moved to a position on the outer side and the upper side of the meter M3. With such display, as explained above, even if the sleep meter M3 is reduced, it is possible to display a number in the meter M3 larger. In the center of the sleep meter M3, a total value of sleep times of the day is displayed.

In the detail display area DF, the deep sleep time, the light sleep time, and the awakening time are displayed in order from the bottom. Besides, above the deep sleep time, the light sleep time, and the awakening time, a graph G31 is displayed in which the time axis AX in a period determined as a sleep time is set and changes in a pulse rate are shown on the time axis AX. In the graph G31, ranges of times determined as the deep sleep time, the light sleep time, and the awakening time are represented by shadings of similar colors same as those in the meter M3. Values set in two places where "00000 bpm" is rendered in a graph area where the graph G31 is displayed are the same as the values in the graph area where the graph G11 is displayed.

Operations performed when the cursor key CK1 facing the left side and the cursor key CK2 facing the right side are pressed during the display of the day detail screen DS31 are the same as the operations performed during the display of the day detail screens DS11 and DS21. With such display, it is possible to clearly represent a sleep state of the user in time series. The user can easily grasp a state of the user during sleep.

Figure 25:
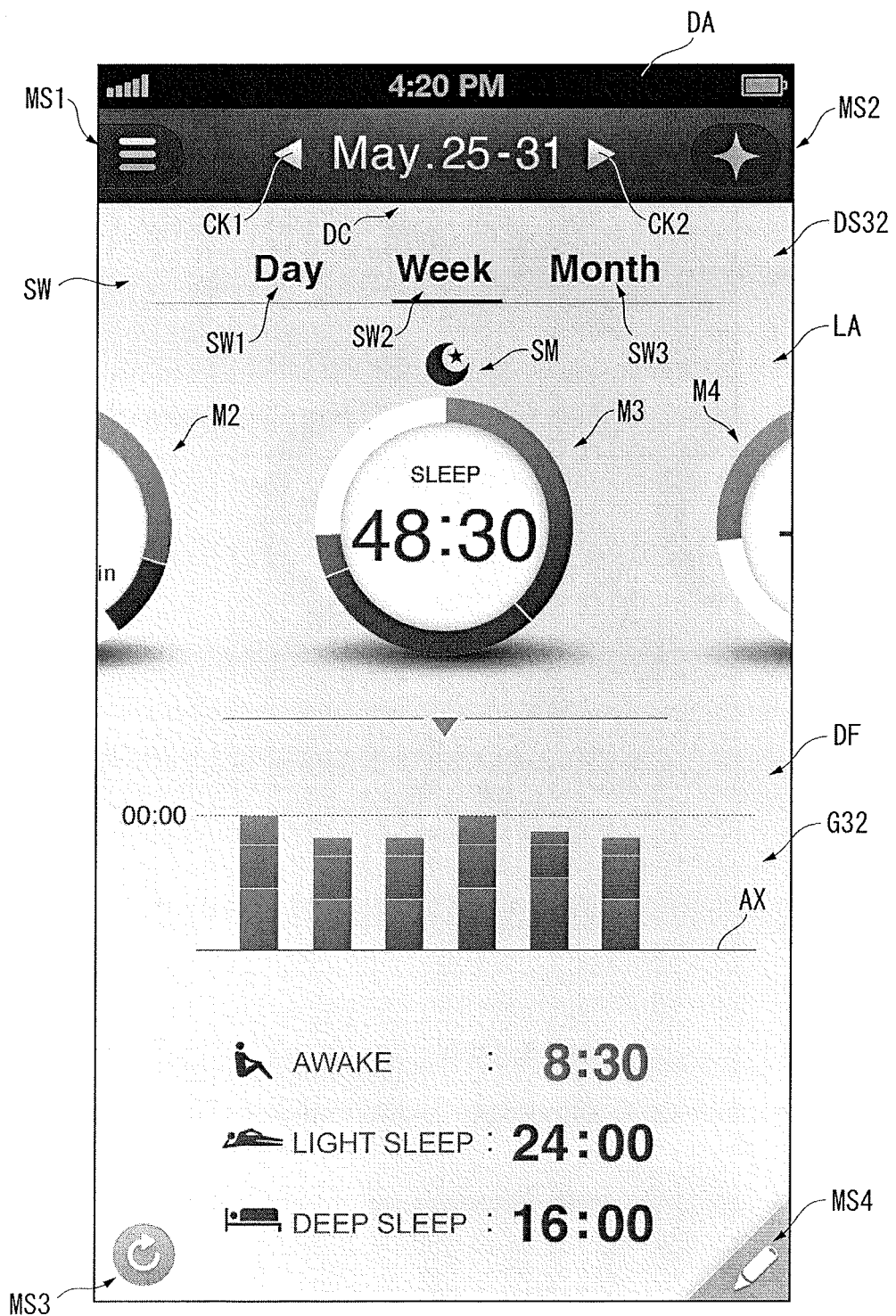
FIG. 25 is a diagram showing a week detail screen concerning the sleep time in the embodiment.

When the area SW2 is entered, a week detail screen DS32 shown in FIG. 25 is displayed. The week detail screen DS32 is a detail screen in week units concerning a sleep time. On the week detail screen DS32, the display switching field SW, the meter arrangement area LA, and the detail display area DF are set.

The sleep meter M3 arranged in the meter arrangement area LA is a meter indicating a total value of each of deep sleep times, light sleep times, and awakening times for the nearest one week. A value displayed in the center of the meter M3 is a total value of sleep times for the nearest one week.

In the detail display area DF, instead of the graph G31, a graph G32 of a stacking type is displayed in which a deep sleep time, a light sleep time, and an awakening time are stacked for each day to the upper side from the time axis AX of a period displayed in the date display area DC. In the graph G32, as explained above, a sleep time of the day is shown in a position on the rightmost side. Each of times displayed in the detail display area DF is a total value of times for each day in the nearest one week. Note that, in a place where "00:00" is rendered in a graph area where the graph G32 is displayed, a maximum of total values (total values of deep sleep times, light sleep times, and awakening times) of days indicated by the displayed graph G23 is set.

Operations performed when the cursor keys CK1 and CK2 are entered during the display of the week detail screen DS32 are the same as the operations performed during the display of the week detail screens DS12 and DS22. With such display, it is possible to easily grasp a sleep status in the nearest one week.

Figure 26:
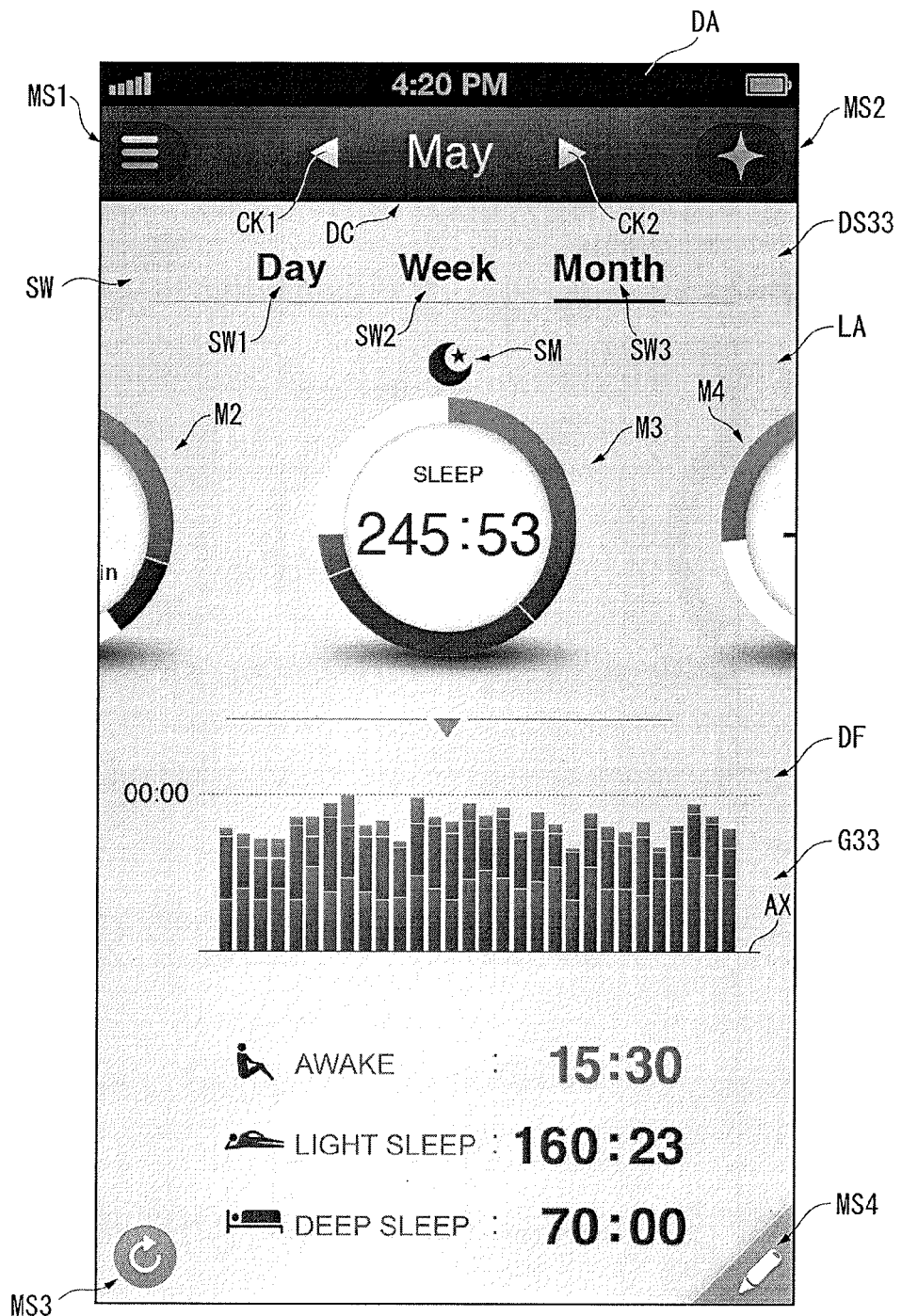
FIG. 26 is a diagram showing a month detail screen concerning the sleep time in the embodiment.

During the display of any one of the day detail screen DS31 and the week detail screen DS32, when the area SW3 is entered, a month detail screen DS33 shown in FIG. 26 is displayed. The month detail screen DS33 is a detail screen in month units concerning a sleep time. On the month detail screen DS33, the display switching field SW, the meter arrangement area LA, and the detail display area DF are set.

The sleep meter M3 arranged in the meter arrangement area LA is a meter indicating a deep sleep time, a light sleep time, and an awakening time for the nearest one month. In the center of the meter M3, a total value of sleep times for the nearest one month is displayed.

In the detail display area DF, like the graph G32, a graph G33 of a stacking type is displayed in which a deep sleep time, a light sleep time, and an awakening time for each day from in the nearest one month are indicated by extension amounts to the upper side from the time axis AX of a period displayed in the date display area DC. In the graph G33, a sleep time of the day is shown in a position on the rightmost side. A value set in a place where "00:00" is rendered in a graph area where the graph G33 is displayed is the same as the value in the graph area where the graph G32 is displayed.

Times displayed in the detail display area DF are total values of times for each day in the nearest one month. With such display, it is possible to bird's-eye-view a sleep history of each day in the nearest one month and easily compare a sleep state in each day.

Operations performed when the cursor keys CK1 and CK2 are entered during the display of the month detail screen DS33 are the same as the operations performed during the display of the month detail screens DS13 and DS23.

Note that, in a state in which any one of the detail screens DS31 to DS33 is displayed, when the information terminal 3 is tilted sideways, a graph corresponding to the screen is enlarged and displayed. Since the display is transitioned in this way, even if a screen of the information terminal 3 is small, it is possible to easily check more detailed changes in time series.

Display of Intake/Consumed Calories

Display of intake/consumed calories is explained.

When the user operates the main screen MS and moves the calorie meter M4 to the first position, the main screen MS shown in FIG. 15 is displayed.

Like the stress meter M1, the calorie meter M4 on the main screen MS is a balance meter indicating an intake calorie and a consumed calorie and is a doughnut graph divided at the lower end of a circle. The calorie meter M4 indicates the consumed calorie using an extension amount in the counterclockwise direction from the reference point BP at the upper end and indicates the intake calorie using an extension amount in the clockwise direction from the reference point BP. In this case, the consumed calorie is rendered in an orange color and the intake calorie is rendered in a yellow color. That is, in the calorie meter M4, as in the meters M1 to M3, the intake/consumed calories are displayed to be identifiable by shadings and gradations of similar colors. In the center of the calorie meter M4, a difference between the intake calorie and the consumed calorie of the day is displayed.

On the main screen MS, in the detail display area DF, the consumed calorie (a value displayed after a word "CALORIE-OUT") and the intake calorie (a value displayed after a word "CALORIE-IN") are arranged in order from the bottom.

Figure 27:
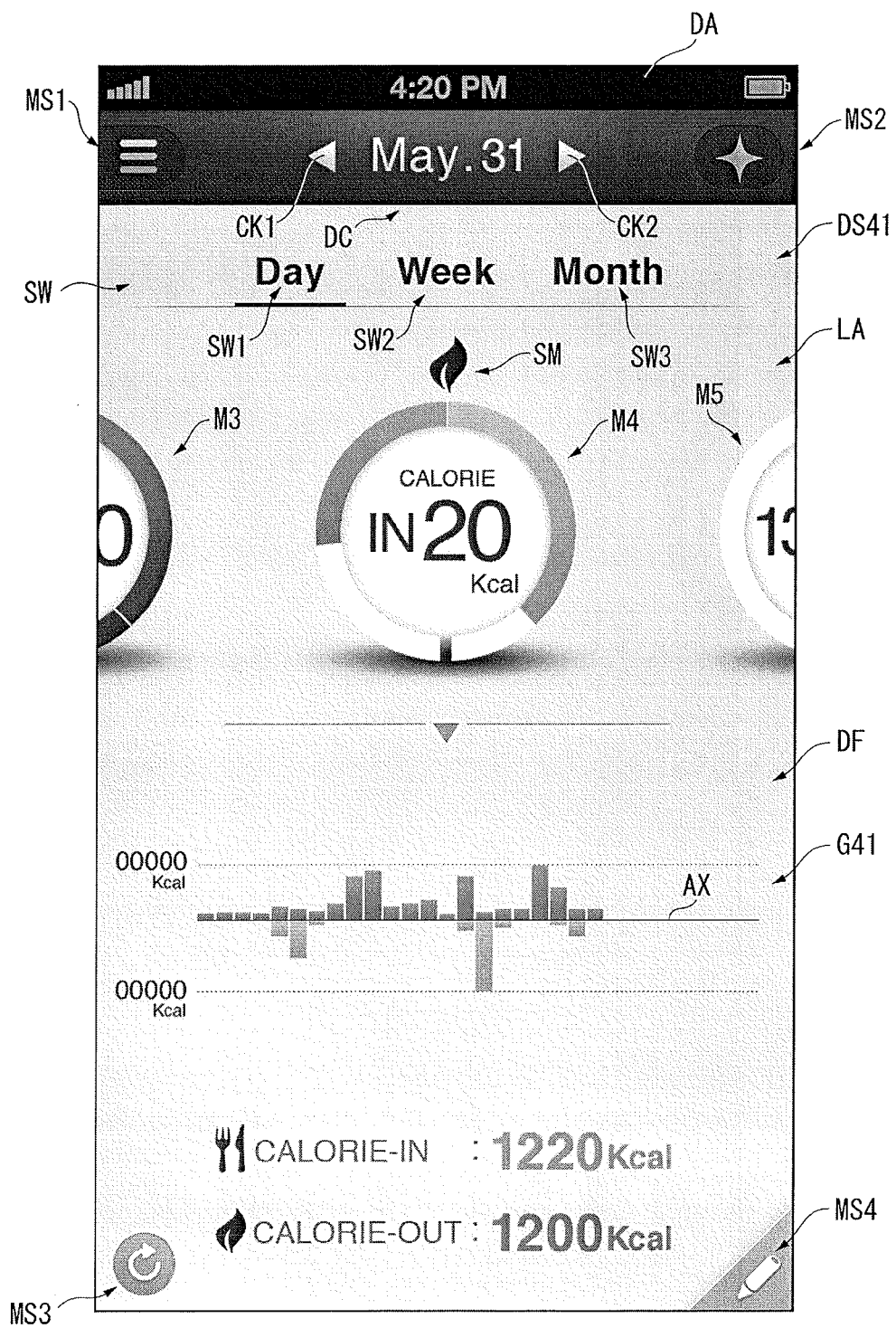
FIG. 27 is a diagram showing a day detail screen concerning a calorie in the embodiment.

On the main screen MS shown in FIG. 15, when the detail display area DF is tapped or clicked, a day detail screen DS41 concerning intake/consumed calories shown in FIG. 27 is displayed.

The day detail screen DS41 is a detail screen in day units concerning intake/consumed calories. On the day detail screen DS41, as on the day detail screens DS11 to DS31, the display switching field SW, the meter arrangement area LA, and the detail display area DF are arranged.

When the day detail screen DS41 is displayed, in the meter arrangement area LA, as on the day detail screens DS11 to DS31, the calorie meter M4 is reduced to size same as the size of the meters M3 and M5 located on the left and right of the calorie meter M4 and is arranged between the meters M3 and M5. The symbol mark SM arranged in the meter M4 is moved to a position on the outer side and the upper side of the meter M4. With such display, as explained above, even if the calorie meter M4 is reduced, it is possible to display a number in the meter M4 larger. In the center of the calorie meter M4, a difference between the intake calorie and the consumed calorie of the day is displayed.

In the detail display area DF, the consumed calorie and the intake calorie are displayed in order from the bottom. Besides, above the consumed calorie and the intake calorie, a graph G41 is displayed in which the time axis AX from the midnight of a date displayed in the date display area DC is set and consumed calories and intake calories are shown on the time axis AX in time series. In the graph G41, the consumed calories are indicated by extension amounts to the upper side from the time axis AX and the intake calories are indicated by extension amounts to the lower side from the time axis AX. Color coding of the intake calories and the consumed calories in the graph G41 are the same as the color coding in the calorie meter M4. In a graph area where the graph G41 is displayed, there are two places where "00000 kcal" is rendered. Of the places, in the place on the lower side, a maximum of intake calories indicated by the graph G41 is set. In the place on the upper side, a maximum of consumed calories indicated by the graph G41 is set.

Operations performed when the cursor keys CK1 and CK2 are entered during the display of the day detail screen DS41 are the same as the operations performed during the display of the day detail screens DS11 and DS31. With such display, a consumed calorie and an intake calorie in one day can be displayed in time series. Therefore, it is possible to easily grasp a life state in one day.

Figure 28:
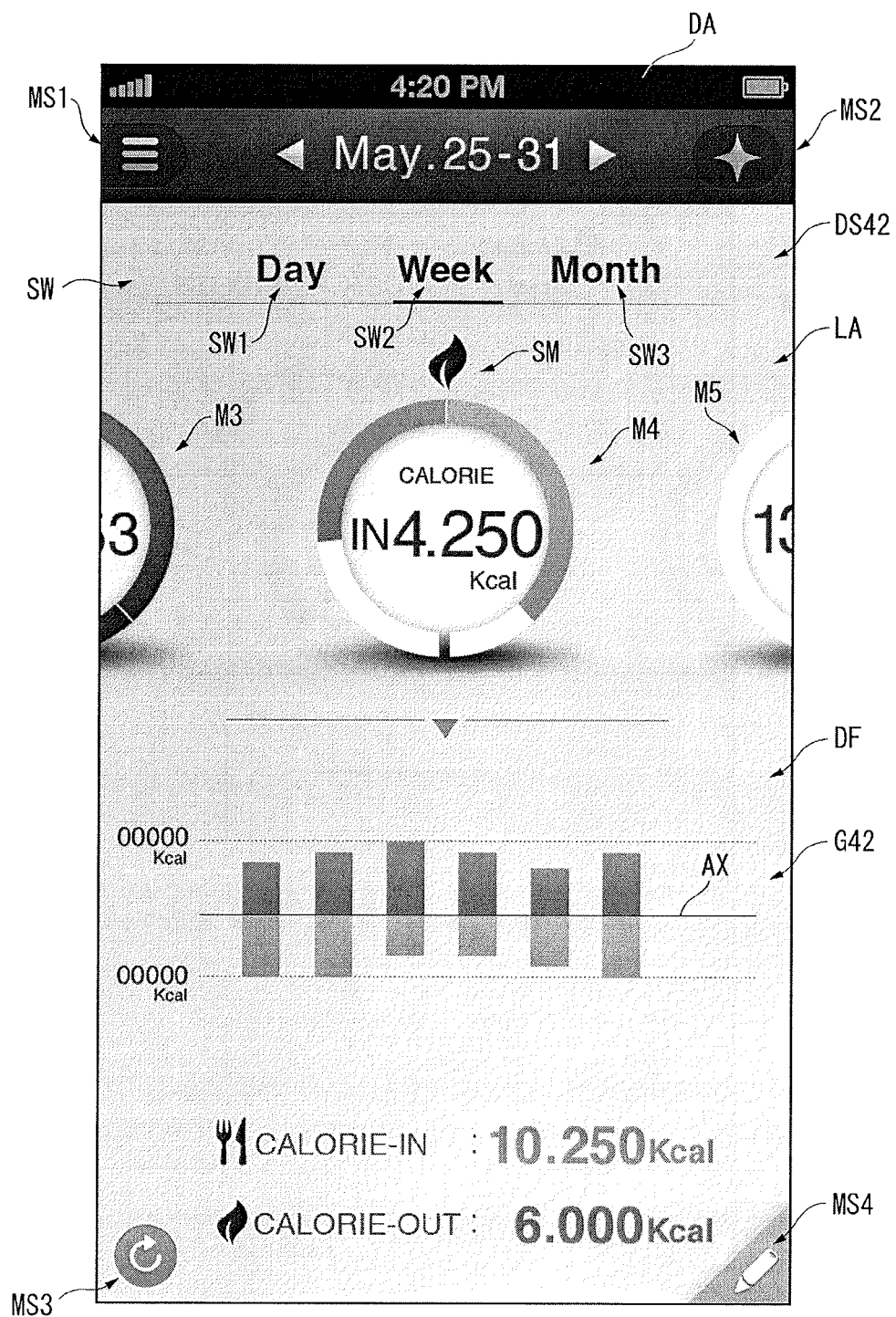
FIG. 28 is a diagram showing a week detail screen concerning the calorie in the embodiment.

When the area SW2 is entered, a week detail screen DS42 shown in FIG. 28 is displayed. The week detail screen DS42 is a detailed screen in week units concerning intake/consumed calories. On the week detail screen DS42, the display switching field SW, the meter arrangement area LA, and the detail display area DF are set.

The calorie meter M4 arranged in the meter arrangement area LA is a meter indicating respective total values of intake calories and consumed calories for the nearest one week. A value displayed in the center of the meter M4 is a difference between the intake calories and the consumed calories for the nearest one week.

In the detail display area DF, instead of the graph G41, a graph G42 is displayed in which a consumed calorie for each day in the nearest one week is indicated by an extension amount to the upper side from the time axis AX in a period displayed in the date display area DC and an intake calorie for each day in the nearest one week is indicated by an extension amount to the lower side from the time axis AX. In the graph G42, an intake calorie and a consumed calorie of the day are shown in a position on the rightmost side. In a graph area where the graph G42 is displayed, there are two places where "00000 kcal" is rendered. Of the places, in the place on the lower side, a maximum of total values of intake calories of days indicated by the graph G41 is set. In the place on the upper side, a maximum of total values of consumed calories of the days indicated by the graph G41 is set.

Operations performed when the cursor keys CK1 and CK2 are entered during the display of the week detail screen DS42 are the same as the operations performed during the display of the week detail screens DS12 and DS32. With such display, a balance between a consumed calorie and an intake calorie in the nearest one week can be easily grasped. Therefore, it is possible to provide the user with an opportunity for reviewing a dietary life. Further, it is possible to provide the user with short-term analysis information concerning the dietary life to attain a goal.

Figure 29:
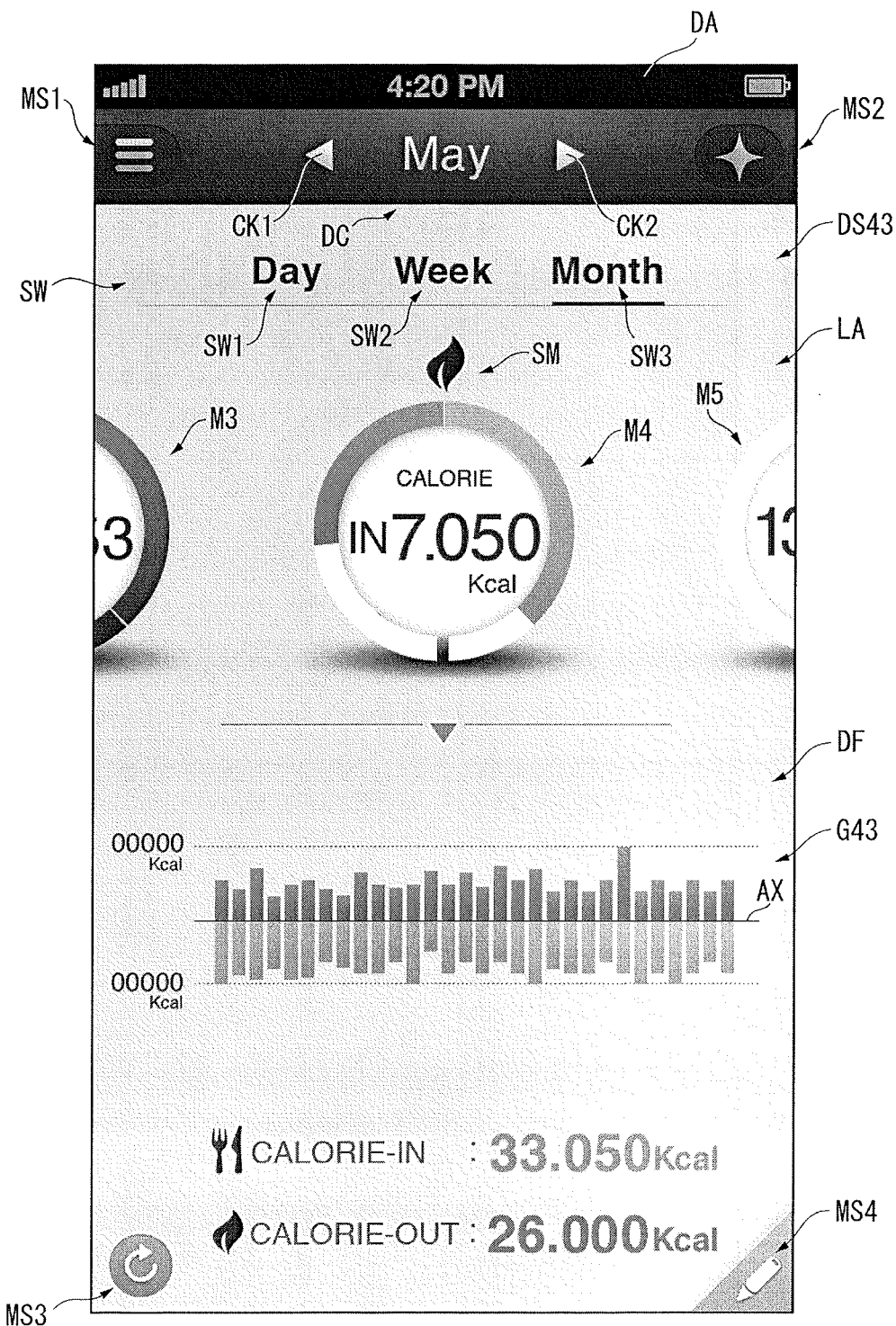
FIG. 29 is a diagram showing a month detail screen concerning the calorie in the embodiment.

During the display of any one of the day detail screen DS41 and the week detail screen DS42, when the area SW3 is entered, a month detail screen DS43 shown in FIG. 29 is displayed. The month detail screen DS43 is a detail screen in month units concerning intake/consumed calories. On the month detail screen DS43, the display switching field SW, the meter arrangement area LA, and the detail display area DF are set.

The calorie meter M4 arranged in the meter arrangement area LA is a meter indicating an intake calorie and a consumed calorie for the nearest one month. In the center of the meter M4, a difference between the intake calorie and the consumed calorie for the nearest one month is displayed.

In the detail display area DF, like the graph G42, a graph G43 is displayed in which a consumed calorie for each day in the nearest one month is indicated by an extension amount to the upper side from the time axis AX in a period displayed in the date display area DC and an intake calorie for each day in the nearest one month is indicated by an extension amount to the lower side from the time axis AX. In the graph G43, an intake calorie and a consumed calorie of the day are shown in a position on the rightmost side. Values set in two places where "00000 kcal" is rendered in a graph area where the graph G43 is displayed are the same as the values in the graph area where the graph G42 is displayed.

Values displayed in the detail display area DF are a total value of intake calories and a total value of consumed calories in the nearest one month. With such display, a balance between a consumed calorie and an intake calorie in the nearest one month can be easily grasped. Therefore, it is possible to provide the user with an opportunity for reviewing a dietary life. Further, it is possible to provide the user with short-term analysis information concerning the dietary life to attain a goal.

Operations performed when the cursor keys CK1 and CK2 are entered during the display of the month detail screen DS43 are the same as the operations performed during the display of the month detail screens DS13 and DS33.

Note that, in a state in which any one of the detail screens DS41 to DS43 is displayed, when the information terminal 3 is tilted sideways, as explained above, a graph corresponding to the screen is enlarged and displayed. Since the display is transitioned in this way, even if the screen of the information terminal 3 is small, it is possible to easily check more detailed changes in time series.

Display of the Number of Steps

Display of the number of steps is explained.

When the user operates the main screen MS and moves the number-of-steps meter M5 to the first position, the main screen MS shown in FIG. 16 is displayed.

The number-of-steps meter M5 is a doughnut graph indicating the number of steps by normal walking (normal number of steps) and the number of steps by walking in the fat burning zone (in-zone number of steps) using an extension amount in the clockwise direction starting from the reference point BP at the upper end. In the number-of-steps meter M5, the normal number of steps and the in-zone number of steps are set in order from a side close to the start point. In this case, the normal number of steps is rendered in a light green color and the in-zone number of steps is rendered in a deep green color. That is, in the number-of-steps meter M5, as in the meters M1 to M4, the numbers of steps are displayed to be identifiable by shadings and gradations of similar colors. In the center of the number-of-steps meter M5, a total value of the numbers of steps (normal numbers of steps and in-zone numbers of steps) in the day is displayed. With such display, the number of steps walked by the user in one day can be easily checked and the in-zone number of steps can be checked. Therefore, it is possible to cause the user to be naturally conscious of increasing the in-zone number of steps for fat burning.

On the main screen MS, in the detail display area DF, the in-zone number of steps (a value displayed after a word "ZONE") and the normal number of steps (time displayed after a word "STEP") are arranged and displayed in order from the bottom. Since the in-zone number of steps and the normal number of steps are displayed together, it is possible to easily grasp a specific number of steps that contributes to fat burning and promote a motivation of the user.

Figure 30:
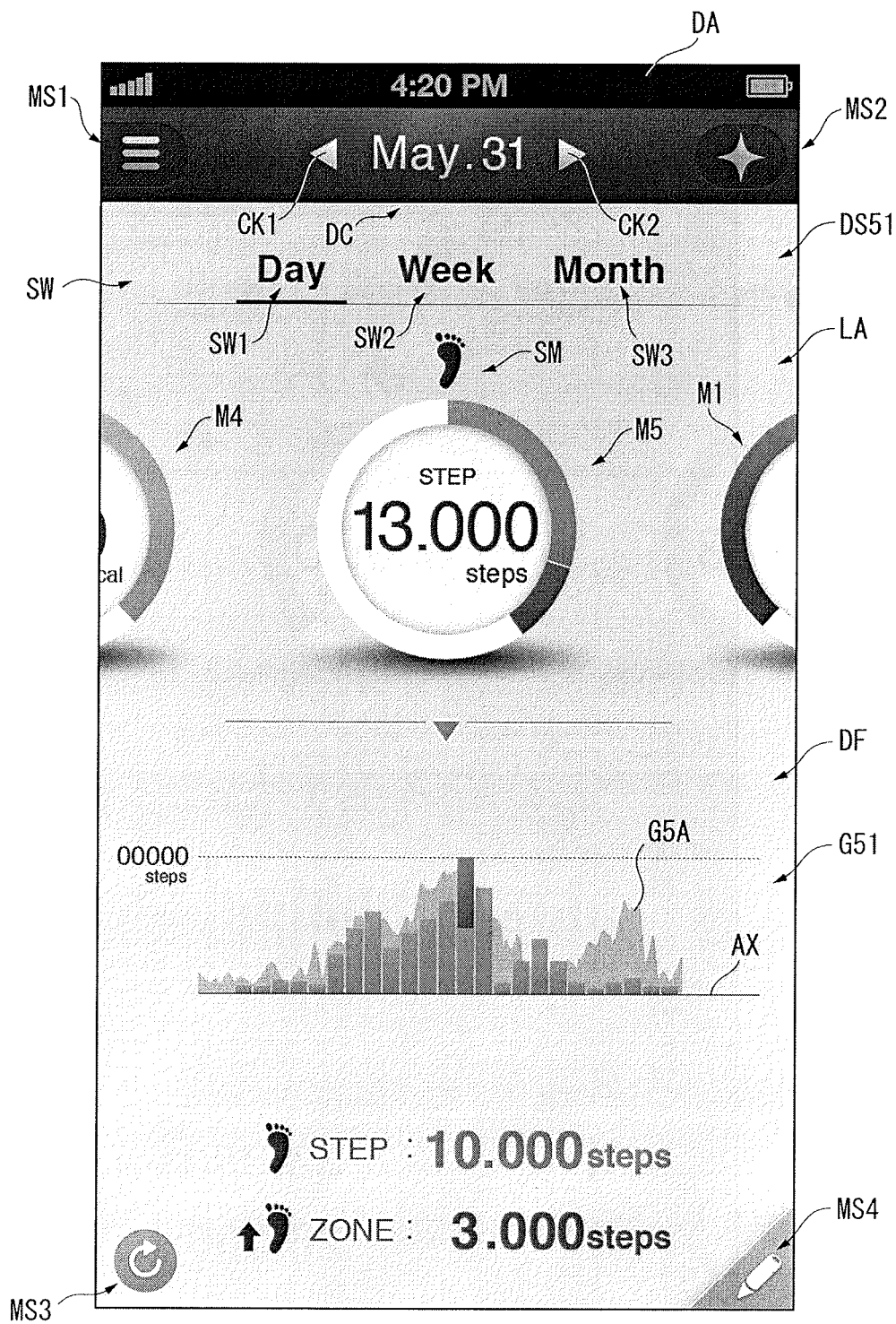
FIG. 30 is a diagram showing a day detail screen concerning the number of steps in the embodiment.

On the main screen MS shown in FIG. 16, when the detail display area DF is tapped or clicked, a day detail screen DS51 concerning the number of steps shown in FIG. 30 is displayed.

The day detail screen DS51 is a detail screen in day units concerning the number of steps. On the day detail screen DS51, as on the day detail screens DS11 to DS41, the display switching field SW, the meter arrangement area LA, and the detail display area DF are arranged.

When the day detail screen DS51 is displayed, in the meter arrangement area LA, as on the day detail screens DS11 to DS41, in a state in which the number-of-steps meter M5 is reduced to size same as the size of the meters M4 and M1 located on the left and right of the number-of-steps meter M5, the number-of-steps meter M5 is arranged between the meters M4 and M1. The symbol mark SM arranged in the meter M5 is moved to a position on the outer side and the upper side of the meter M5. With such display, even if the number-of-steps meter M5 is reduced, it is possible to display a number in the meter M5 larger. In the center of the number-of-steps meter M5, a total value of the numbers of steps in a date of display of data is displayed.

In the detail display area DF, the in-zone number of steps and the normal number of steps are displayed in order from the bottom. Besides, above the in-zone number of steps and the normal number of steps, while being superimposed on a graph G5A showing changes in a pulse rate on the time axis AX from the midnight of a date displayed in the date display area DC, a graph G51 is displayed in which normal numbers of steps and in-zone numbers of steps are stacked by extension amounts to the upper side from the time axis AX same as the time axis AX of the graph G5A. Times indicated by the time axes AX of the graph 5A and the graph G51 coincide with each other. In a graph area where the graph G51 is displayed, a maximum of numbers of steps indicated by the graph G51 is set in a place where "00000 steps" is rendered.

Operations performed when the cursor keys CK1 and CK2 facing the right side are entered during the display of the day detail screen DS51 are the same as the operations performed during the display of the day detail screens DS11 and DS41.

Figure 31:
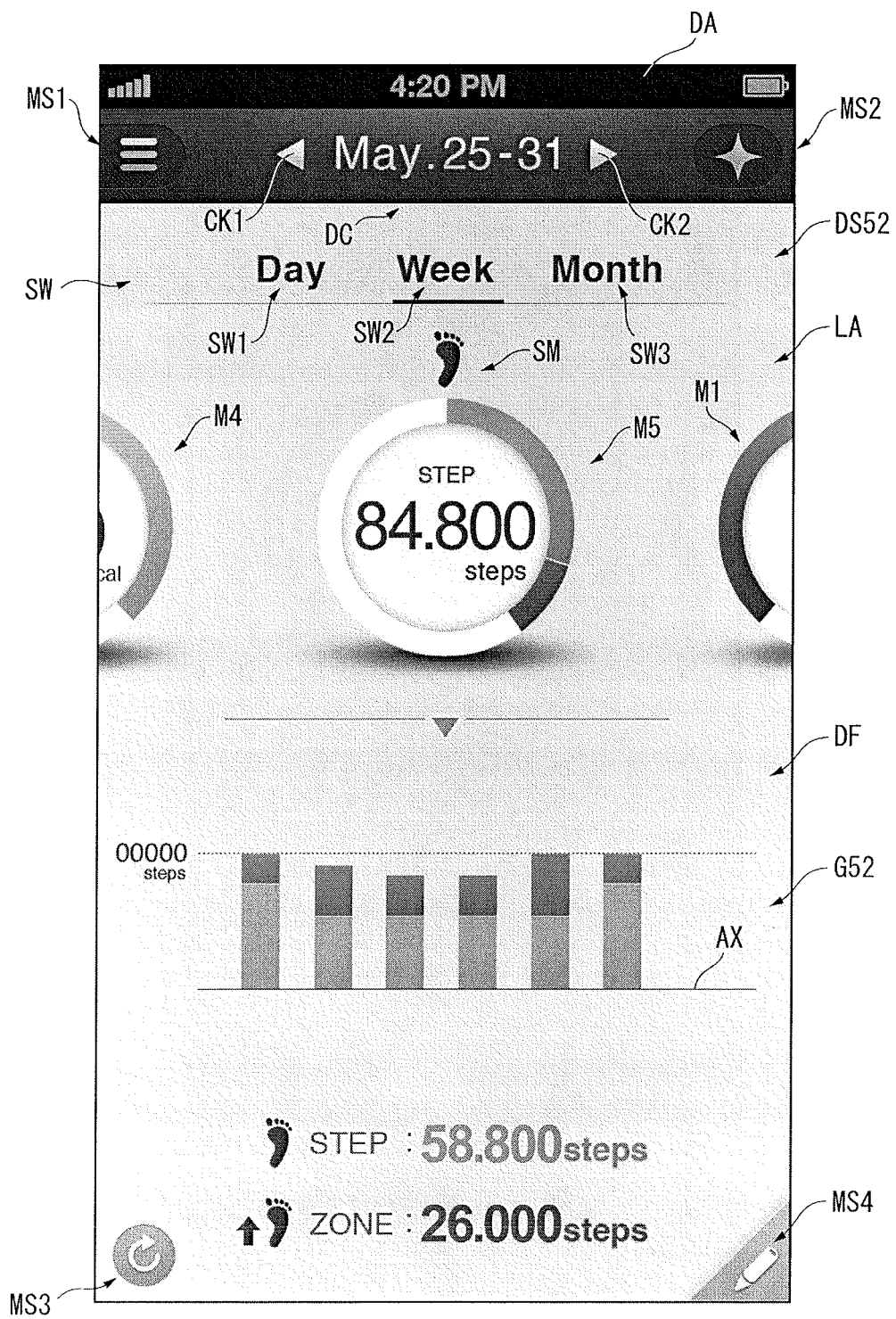
FIG. 31 is a diagram showing a week detail screen concerning the number of steps in the embodiment.

When the area SW2 is entered, a week detail screen DS52 shown in FIG. 31 is displayed. The week detail screen DS52 is a detail screen in week units concerning the number of steps. On the week detail screen DS52, the display switching field SW, the meter arrangement area LA, and the detail display area DF are set.

The number-of-steps meter M5 arranged in the meter arrangement area LA is a meter indicating a total value of normal numbers of steps and a total value of in-zone numbers of steps for the nearest one week. A value displayed in the center of the meter M5 is a total value of the numbers of steps for the nearest one week.

In the detail display area DF, instead of the graph G51, a graph G52 of a stacking type is displayed in which a normal number of steps and an in-zone number of steps for the nearest one week are stacked for each day to the upper side from the time axis AX of a period displayed in the date display area DC. In the graph G52, as explained above, the number of steps of the day is shown in a position on the rightmost side. The normal number of steps and the in-zone number of steps displayed in the detail display area DF are respectively total values of times for each day in the nearest one week. In a graph area where the graph G52 is displayed, a maximum of total values of the numbers of steps (normal numbers of steps and in-zone numbers of steps) of days indicated by the graph G52 is set in a place where "00000 steps" is rendered.

Operations performed when the cursor keys CK1 and CK2 are pressed during the display of the week detail screen DS52 are the same as the operations performed during the display of the week detail screens DS12 and DS42. With such display, it is possible to provide the user with an opportunity for, while grasping a walking status in the nearest one week, reviewing the week.

Figure 32:
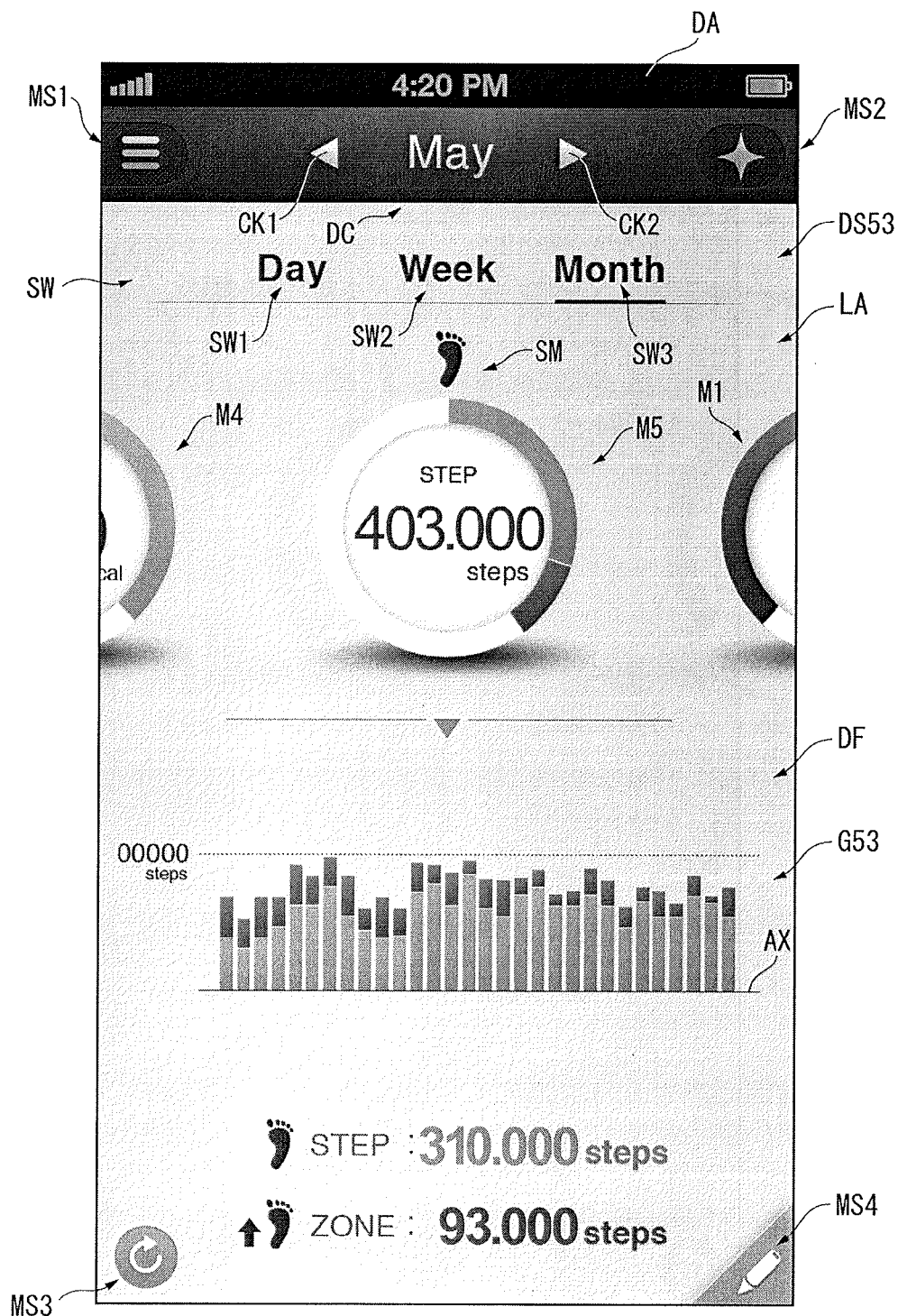
FIG. 32 is a diagram showing a month detail screen concerning the number of steps in the embodiment.

During the display of any one of the day detail screen DS51 and the week detail screen DS52, when the area SW3 is entered, a month detail screen DS53 shown in FIG. 32 is displayed. The month detail screen DS53 is a detail screen in month units concerning the number of steps. On the month detail screen DS53, the display switching field SW, the meter arrangement area LA, and the detail display area DF are set.

The number-of-steps meter M5 arranged in the meter arrangement area LA is a meter indicating a total value of normal numbers of steps and a total value of in-zone numbers of steps for the nearest one month. In the center of the meter M5, a total value of the numbers of steps for the nearest one month is displayed.

In the detail display area DF, like the graph G52, a graph G53 of a stacking type is displayed in which a normal number of steps and an in-zone number of steps for each day in the nearest one month are indicated by an extension amount to the upper side from the time axis AX of a period displayed in the date display area DC. In the graph G53, the number of times of the day is shown in a position on the rightmost side. A value set in a place where "00000 steps" is rendered in a graph area where the graph G53 is displayed is the same as the value in the graph area where the graph G52 is displayed.

The numbers of steps displayed in the detail display area DF are respective total values of normal numbers of steps and in-zone numbers of steps in the nearest one month.

Operations performed when the cursor keys CK1 and CK2 are input during the display of the month detail screen DS53 are the same as the operations performed during the display of the month detail screens DS13 to DS43.

Note that, in a state in which any one of the detail screens DS51 to DS53 is displayed, when the information terminal 3 is tilted sideways, as explained above, a graph corresponding to the screen is enlarged and displayed.

The user can check a mental state and a behavior state of the user by checking the main screen MS and the detail screens of the respective items.

Note that, during the display of the main screen MS, a meter displayed in the first position is the stress meter M1 during the initial display. However, thereafter, a meter displayed during the last display is displayed.

Operation During an Update Key Input

Figure 33:
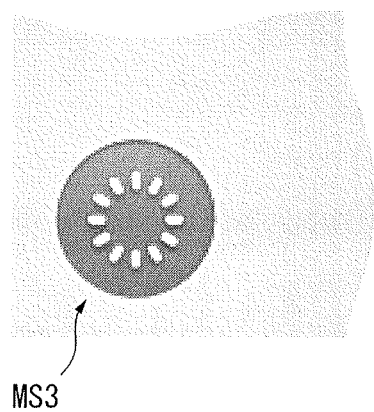
FIG. 33 is a diagram showing an update key during communication in the embodiment.

FIG. 33 is a diagram showing the update key MS3 in a state in which the update key MS3 is entered and the information terminal 3 communicates with the measuring apparatus 2 or the management server 5.

When the update key MS3 set on the main screen MS and the detail screens is entered, the main control unit 361 accesses the measuring apparatus 2 via the communication control unit 363 and the communication unit 33 and acquires new measurement information from the measuring apparatus 2. The main control unit 361 accesses the management server 5 and acquires measurement information uploaded anew. In this case, the display control unit 362 changes a pattern of the update key MS3 to a pattern of a circle, the outer circumference of which is formed by dots, as shown in FIG. 33.

When the new measurement information is acquired, the calculation by the calculating unit 365 is performed. The display control unit 362 updates display contents of the main screen MS and the detail screens on the basis of the acquired measurement information and a calculation result by the calculating unit 365.

Note that, when selection operation for the update key MS3 is performed, information of a meter in the first place can be updated. According to such a configuration, only intended information can be updated and displayed. When selection operation for the update key is performed, information of meters located in the positions other than the first position may be updated. According to such a configuration, the information of the meters arranged in the positions other than the first position is also updated and the meters are rendered again. Therefore, the user can easily grasp a changed meter. Changes in the meters other than the meter displayed in the first position are simultaneously represented in this way. Consequently, it is possible to direct the interest of the user to the other meters as well and urge the user to check diversified information.

Configuration of the Input Screen

Figure 34:
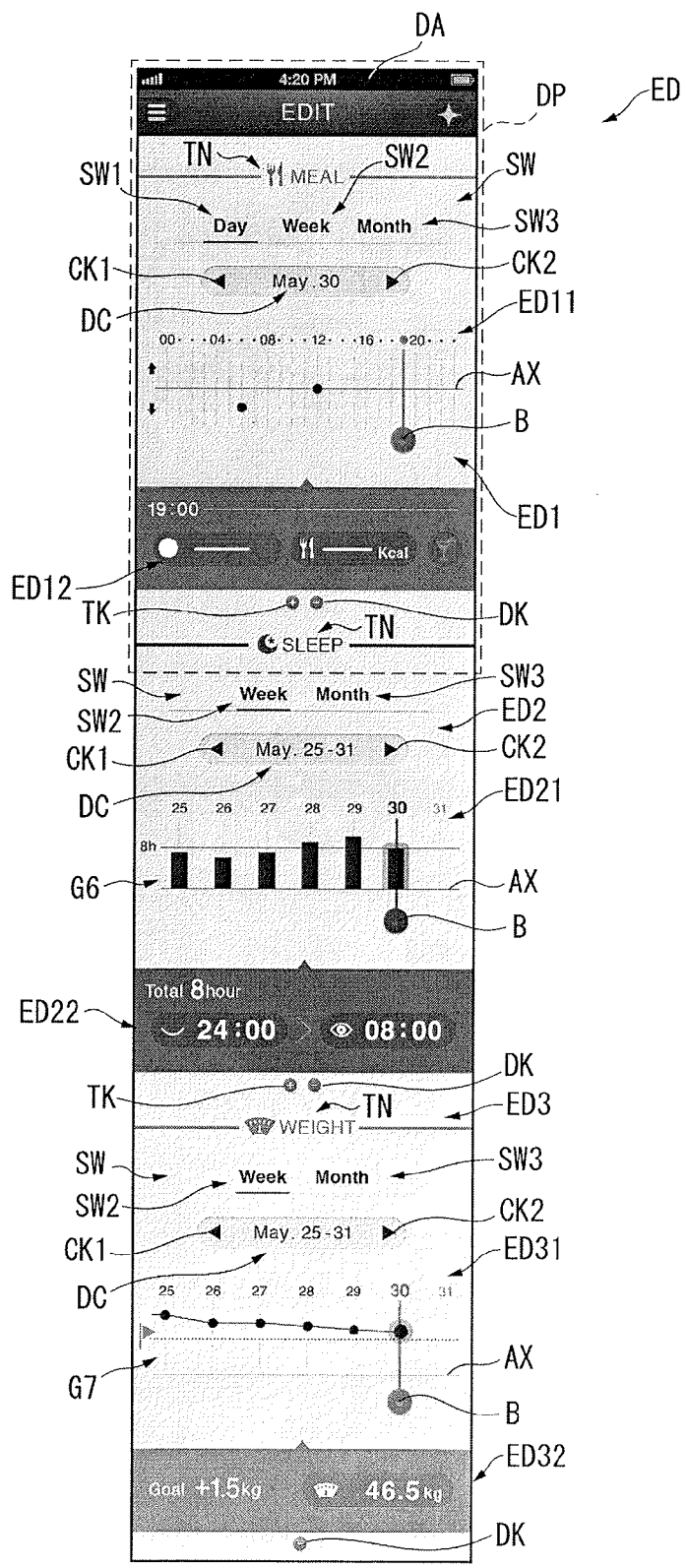
FIG. 34 is a diagram showing an input screen in the embodiment.
Figure 35:
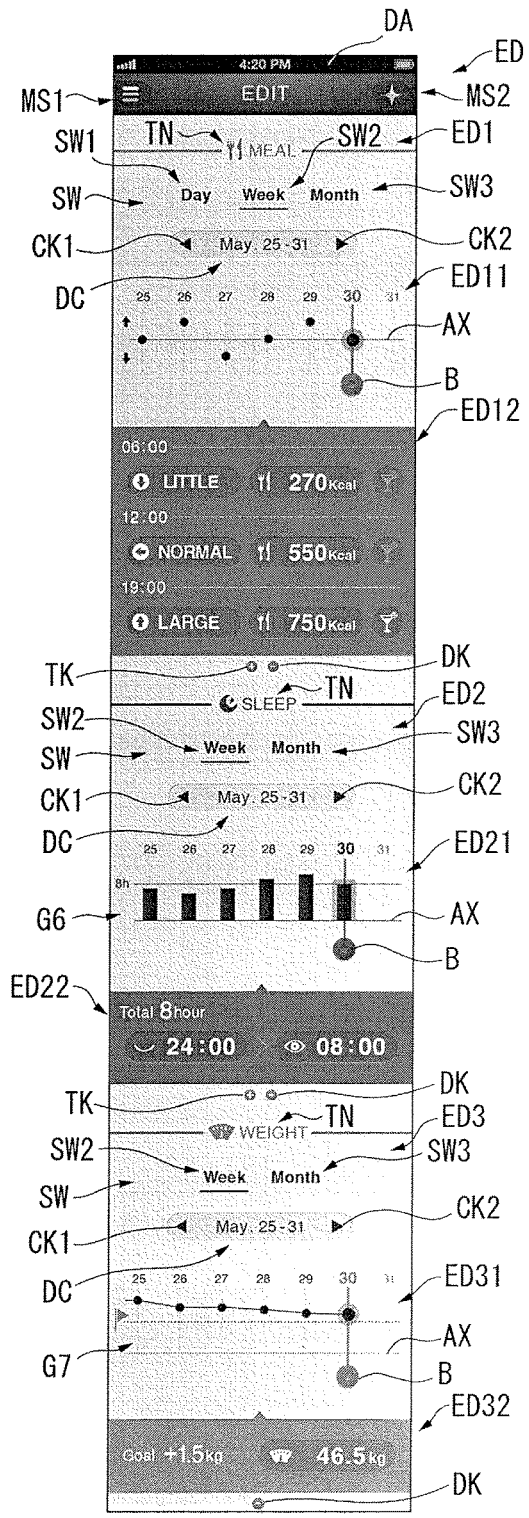
FIG. 35 is a diagram showing the input screen in the embodiment.
Figure 36:
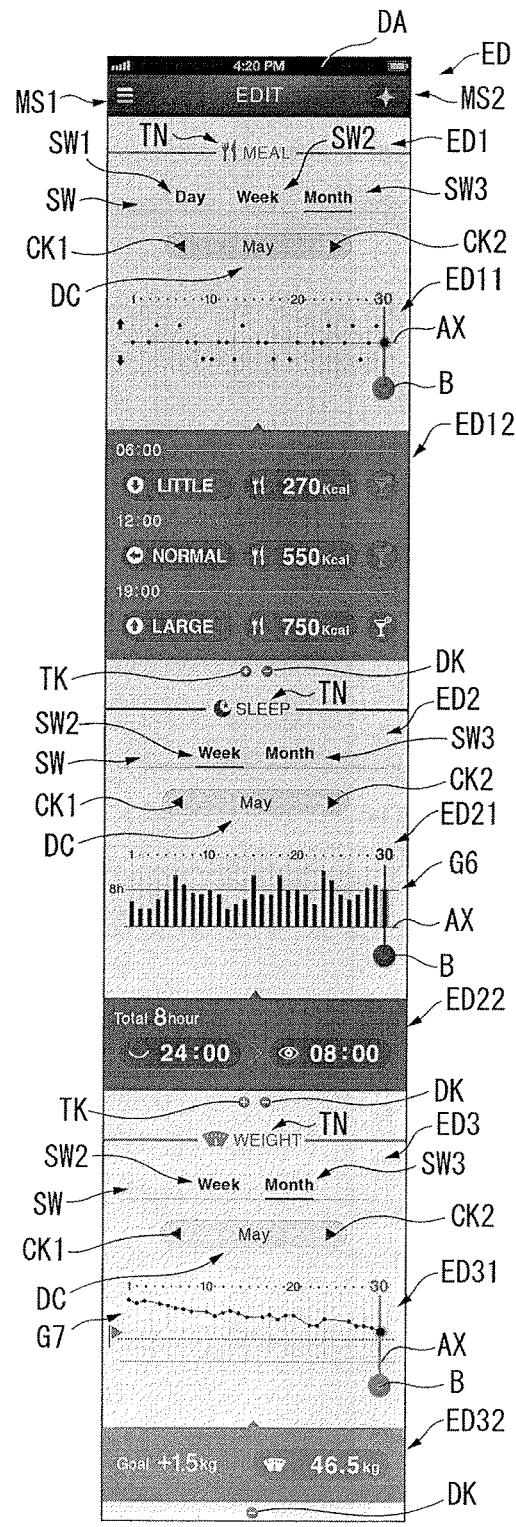
FIG. 36 is a diagram showing the input screen in the embodiment.

FIGS. 34 to 36 are diagrams showing examples of the input screen ED.

When the editing key MS4 set on the main screen MS and the detail screens is pressed, the input screen ED shown in FIG. 34 is displayed to extend from below the editing key MS4.

The input screen ED is a vertically long screen on which a meal registration area ED1, a sleep time editing area ED2, and a weight registration area ED3 are arrayed in series in order from the top. The user flicks or drags the input screen ED up and down, whereby setting screens are displayed. An arraying direction of the areas ED1 to ED3 is a direction orthogonal to the perpendicular of an image display area of the display unit 31. In this embodiment, the arraying direction coincides with the longitudinal direction of the image display area having a rectangular shape. Note that the orthogonal direction is not limited to the longitudinal direction and may be the latitudinal direction or other directions.

Registration of Meal Information

The meal registration area ED1 is an area including an item name TN inscribed as "MEAL" and is an area where daily meal information is registered. Specifically, in the meal registration area ED1, a classification of a meal (any one of breakfast, lunch, dinner, snack, and drinking), time of the meal, and a dietary intake (any one of "rather large", "normal", "rather small", and "none") are registered. Among these items, it is possible to register the dietary intake by selecting the dietary intake out of icons ("rather large", "normal", "rather small", and "none"), which are selection items for the dietary intake serving as a relative amount selecting section. By registering these kinds of information, a calorie of the meal (an intake calorie) is automatically set on the basis of the basal metabolism.

Specifically, in the meal registration area ED1, the display switching field SW, a date display area DC indicating a date when meal information can be set, and the cursor keys CK1 and CK2 facing the left and the right provided on the left and right of the date display area DC, which are objects, are set. Besides, in the meal registration area ED1, a variable display area ED11, display content of which is switched according to selection of any one of the areas SW1 to SW3 inscribed as "Day", "Week", and "Month" set in the display switching field SW, a content display area ED12 in which meal information is registered and displayed, an addition key TK, and a deletion key DK are set. The variable display area ED11 and the content display area ED12 are also formed by objects.

When the area SW1 is pressed, in the variable display area ED11, as shown in FIG. 34, the time axis AX starting from the midnight of a date displayed in the date display area DC is displayed. When meal information is already set, a mark (in FIG. 34, a black circle) is added as a figure in a position on the time axis AX corresponding to time of a meal included in the meal information. In the variable display area ED11, a bar B orthogonal to the time axis AX is set. Time when the meal information is set can be selected by moving the bar B along the time axis AX. A date when the meal information is set can be selected by pressing the cursor keys CK1 and CK2.

Note that, as explained in detail below, the position of the mark is set according to an input dietary intake.

The meal information is registered when the bar B is moved to select desired time and, after the desired time is input to the content display area ED12 located below the variable display area ED11, the addition key TK is entered.

That is, although not shown in the figure, a classification of a meal and a dietary intake can be set by selecting icons. Time of the meal is automatically set according to the position of the bar B. When the classification of the meal, the dietary intake, and the time of the meal are input, a calorie of the meal is calculated on the basis of the basal metabolism. A value of the calorie is automatically displayed. Note that, when the classification of the meal is "drinking", the value of the calories is a fixed value.

After these kinds of meal information are input, when the addition key TK is pressed, the meal information is stored in the storing unit 35 and registered.

By introducing such an input method for meal information, the user can complete a meal input with a small number of operations. Most of diet support systems currently used in general require complicated operation such as an input or selection of meal menu items. Therefore, it is difficult for a user to grasp a dietary life of the user and an actual state of activities for diet. On the other hand, in the meal input method in this embodiment, the meal input can be completed by transitioning the screen to the input screen ED, moving the bar B to desired date and time, pressing the addition key TK, and selecting an approximate dietary intake. Therefore, since a burden on the user for the meal input is greatly reduced, it is possible to promote an incentive to continuously input the meal information.

The meal information registered in this way is displayed in the content display area ED12 when a time period of the meal and time selected by moving the bar B coincide with each other. While the registered meal information is displayed, when the deletion key DK is entered, the meal information is deleted.

Operations performed when the cursor keys CK1 and CK2 are pressed during the display of the meal registration area ED1 in day units are the same as the operations performed during the display of the day detail screens DS11 to DS51.

On the other hand, when the area SW2 is pressed, as shown in FIG. 35, the time axis AX displayed in the variable display area ED11 changes to a time axis for each day starting from the nearest Sunday or Monday. Marks (in FIG. 35, black circles) corresponding to dietary intakes of days (any one of "rather large", "normal", "rather small", and "none") are set in positions corresponding to the respective days. Specifically, the position of the mark is set on the time axis AX if the corresponding dietary intake is "normal", set in a position on the upper side with respect to the time axis AX if the dietary intake is "rather large", and set in a position on the lower side with respect to the time axis AX if the dietary intake is "rather small".

For example, on twenty-fifth day in the variable display area ED11, since the dietary intake is "normal", the mark is added on the time axis AX. On the other hand, on twenty-sixth day, since the dietary intake is "rather large", the mark (the black circle) is added on the upper side of the time axis AX. On twenty-seventh day, since the dietary intake is "rather small", the mark is added on the lower side of the time axis AX. The same applies to the meal registration area ED1 in day units.

When a date is selected by the bar B, if meal information is registered on the selected date, the meal information is displayed in the content display area ED12. In this case, if a plurality of kinds of meal information are registered, the kinds of meal information are displayed in the content display area ED12 from the top in order of time periods of meals included in the kinds of meal information.

Note that operations performed when the cursor keys CK1 and CK2 are pressed during the display of the meal registration area ED1 in week units are the same as the operations performed during the display of the week detail screens DS12 to DS52.

In the meal registration area ED1 in week units, as in the meal registration area ED1 in day units, it is possible to register the meal information.

In this case, the meal information can be registered by, after moving the bar B to select a date when the meal information is registered, inputting the meal information including time of the meal in the content display area ED12, pressing the addition key TK.

When the registered meal information is deleted, the meal information to be deleted can be deleted by, after selecting the meal information to be deleted displayed in the content display area ED12, pressing the deletion key DK.

Operations performed when the cursor keys CK1 and CK2 are pressed during the display of the meal registration area ED1 in week units are the same as the operations performed during the display of the week detail screens DS12 to DS52. Since the meal information is displayed by week in this way, the user can grasp an actual state of a short-term dietary habit of the user. It is possible to provide the user with an opportunity for improving a dietary habit in the following week.

On the other hand, when the area SW3 is pressed, as shown in FIG. 36, the time axis AX displayed in the variable display area ED11 changes to a time axis for each day starting from the nearest first day (a first day of a month). Marks corresponding to the dietary intakes of days (in FIG. 36, black circles) are set in positions corresponding to the respective days. Note that a setting method for the marks is the same as the setting method for the marks in week units.

When a date is selected by the bar B, as in the selection in week units, if meal information is registered in the selected data, the meal information is displayed in the content display area ED12.

Operations performed when the cursor keys CK1 and CK2 are pressed during the display of the meal registration area ED1 in month units are the same as the operations performed during the display of the month detail screens DS13 to DS53.

In the meal registration area ED1 in month units, as in the meal registration areas ED1 in day units and week units, it is possible to register the meal information. A registration method for the meal information in this case is the same as the method of registering the meal information using the meal registration area ED1 in week units. Since the meal information is displayed in month units in this way, the user can bird's-eye-view an actual state of a mid-term dietary habit of the user. Activities such as diet and health promotion require long-term efforts. A dietary habit is one of important keys. By grasping information concerning the dietary habit while changing a period to day, week, and month, the user can grasp tendencies concerning meals and dietary habits of the user and can make use of the tendencies for the diet and the health promotion.

Note that, when the meal registration areas ED1 in week units and month units are displayed, a position on the time axis AX may be set as an average of dietary intakes or an average of intake calories in a period of the display. Further, a position where a mark is set with respect to the time axis AX may be set as a difference between an intake calorie and a consumed calorie of the day. If the intake calorie is larger than the consumed calorie, the mark may be set on the upper side with respect to the time axis AX according to the difference. If the intake calorie is smaller than the consumed calorie, the mark may be set on the lower side with respect to the time axis AX according to the difference. In this case, in the meal registration area ED1 in day units, the mark may be set according to the dietary intake. In the meal registration areas ED1 in week units and month units, the mark may be set according to the difference between the intake calorie and the consumed calorie.

Editing of a Sleep Time

As shown in FIGS. 34 to 36, the sleep time editing area ED2 is an area including the item name TN inscribed as "SLEEP" and includes a configuration same as the configuration of the meal registration area ED1. In the sleep time editing area ED2, a variable display area ED21, display content of which is switched according to selection of any one of the areas SW2 and SW3 of the display switching field SW, a content display area ED22 where information concerning a sleep time is edited and displayed, the addition key TK, and the deletion key DK are set. That is, the sleep time editing area ED2 can be displayed in any one of week units and month units.

In the sleep time editing area ED2 in week units, as shown in FIGS. 34 and 35, in the variable display area ED21, the time axis AX for each day starting from the nearest Sunday or Monday is arranged and a graph G6 indicating sleep times of days is displayed.

On the other hand, in the sleep time editing area ED2 in month units, as shown in FIG. 36, in the variable display area ED21, the time axis AX for each day starting from the nearest first day (beginning of a month) is arranged and the graph G6 indicating sleep times of days is displayed.

When the bar B provided in the time axis AX is moved and a date when a sleep time is displayed or edited is selected, if a sleep time is already registered, information concerning the sleep time is displayed in the content display area ED22.

Note that the already registered sleep time includes a sleep time edited by the user besides a sleep time calculated on the basis of measurement information received from the measuring apparatus 2.

In the sleep time editing areas ED2 in week units and month units, in editing a sleep time, first, the user moves the bar B to select a date when the sleep time is edited. When the user presses information concerning the sleep time displayed in the content display area ED22, start time and end time of sleep can be edited.

Note that, when the user desires to add a sleep time of a nap or the like, if the user presses the addition key TK, a field in which new start time and end time of sleep can be input in the content display area ED22 is added.

On the other hand, when the user presses the deletion key DK after selecting the information concerning the sleep time displayed in the content display area ED22, the selected information is deleted.

Registration of Weight

As shown in FIGS. 34 to 36, the weight registration area ED3 is an area including the item name TN inscribed as "WEIGHT" and includes a configuration same as the configuration of the meal registration area ED1. In the weight registration area ED3, a variable display area ED31, display content of which is switched according to selection of any one of the areas SW2 and SW3 of the display switching field SW, a content display area ED32 where weight is registered and displayed, and the deletion key DK are set. That is, like the sleep time editing area ED2, the weight registration area ED3 can be displayed in any one of week units and month units.

In the weight registration area ED3 in week units, as shown in FIGS. 34 and 35, in the variable display area ED31, the time axis AX for each day starting from the nearest Sunday or Monday is arranged and a graph G7, which is a line graph, indicating weights of days is displayed. Further, in the variable display area ED31, a mark (in FIGS. 34 and 35, a mark of a flag) indicating target weight is added.

On the other hand, in the weight registration area ED3 in month units, as shown in FIG. 36, in the variable display area ED31, the time axis AX for each day starting from the nearest first day (beginning of a month) is arranged and the graph G7, which is the line graph, indicating weights of days is displayed. As explained above, in the variable display area ED31, a mark indicating target weight is added.

When the bar B provided in the time axis AX is moved and a date when weight is displayed or edited is selected, if weight is already registered, the registered weight is displayed in the content display area ED32 together with the target weight.

In the weight registration areas ED3 in week units and month units, in setting weight, first, the user moves the bar B to select a date when weight is set. Then, when the user presses the content display area ED32, weight can be input.

Note that, when the user desires to delete registered weight, after selecting information displayed in the content display area ED32, the user can delete the registered weight by pressing the deletion key DK.

The display of the input screen ED is executed by the display control unit 362.

Specifically, when the editing key MS4 is pressed, the display control unit 362 generates and displays the input screen ED. In this case, the display control unit 362 causes the display unit 31 to display any one of the areas ED1 to ED3 and a part of objects forming an area adjacent to the area. Consequently, as explained above, for example, when the meal registration area ED1 in day units is displayed, the item name TN, which is an object forming the sleep time editing area ED3, is displayed.

That is, a combined dimension in the longitudinal direction of the meal registration area ED1 in day units among the areas ED1 to ED3 included in the input screen ED and the constant display area DA is smaller than a dimension in the longitudinal direction of the image display area DP of the display unit 31. Similarly, a combined dimension in the longitudinal direction of the sleep time editing area ED2 and the constant display area DA and a combined dimension in the longitudinal direction of the weight registration area ED3 and the constant display area DA are smaller than the dimension in the longitudinal direction of the image display area DP.

Therefore, when the meal registration area ED1 in day units is displayed, a part of the sleep time editing area ED2 (the item name TN inscribed as "SLEEP") is displayed on the lower side of the display screen. When the sleep time editing area ED2 is displayed, a part of the meal registration area ED1 is displayed on the upper side of the display screen or a part of the weight registration area ED3 (the item name TN inscribed as "WEIGHT") is displayed on the lower side of the display screen. Further, when the weight registration area ED3 is displayed, a part of the sleep time editing area ED2 is displayed on the upper side of the display screen.

Consequently, when any one area of the areas ED1 to ED3 is displayed, since a part of the other areas are displayed, it is possible to urge the user to perform editing and setting in the other areas. Therefore, it is possible to make it a practice to perform item editing and setting on the input screen ED.

Note that, after the input screen ED transitions to the main screen MS or the detail screens, when the input screen ED is opened again, an area displayed during the last display is displayed. Therefore, when the weight registration area ED3 in month units is displayed during the last display, the weight registration area ED3 in month units is displayed.

Event Check Screen

Figure 37:
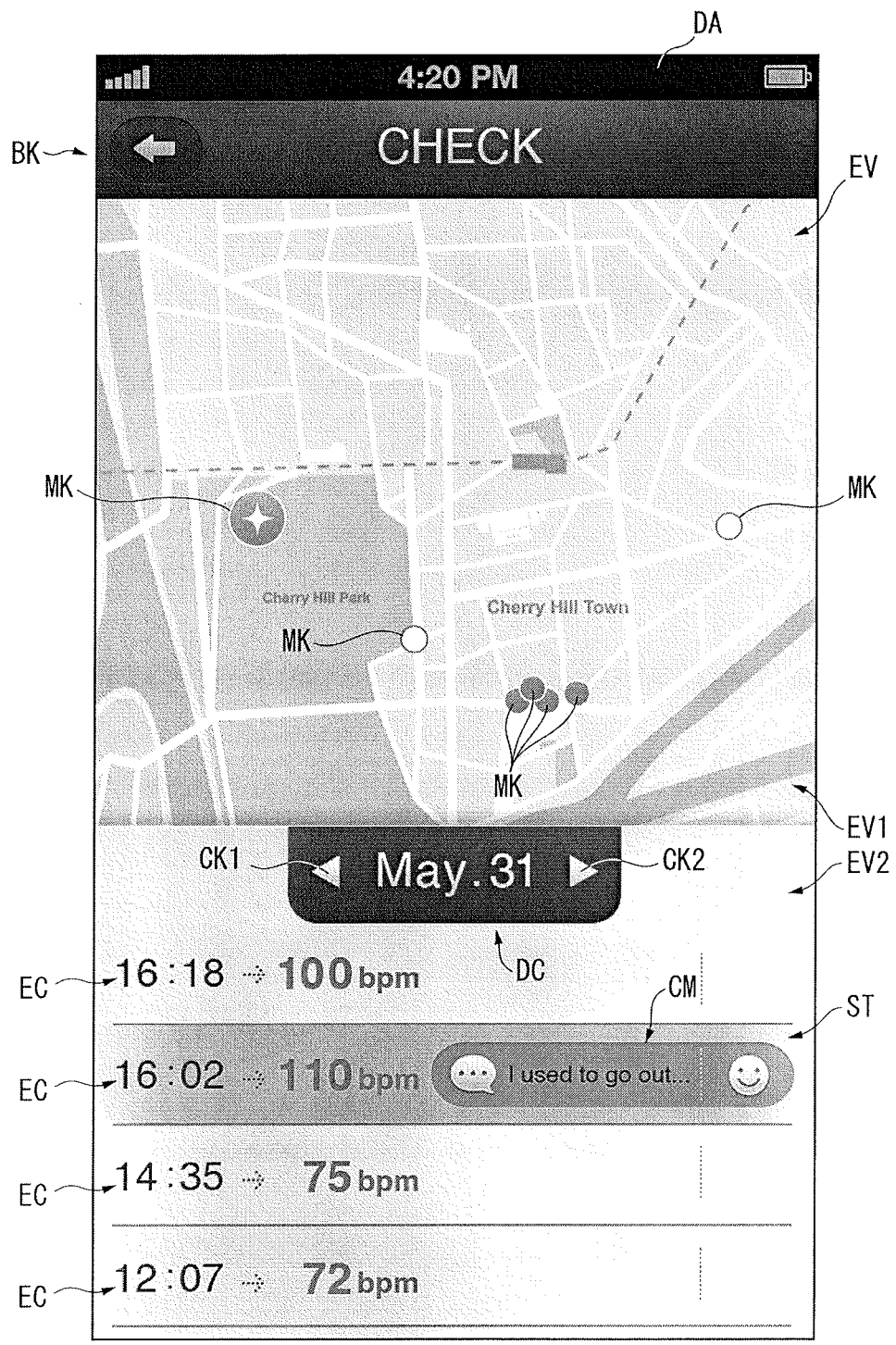
FIG. 37 is a diagram showing an event check screen in the embodiment.
Figure 38:
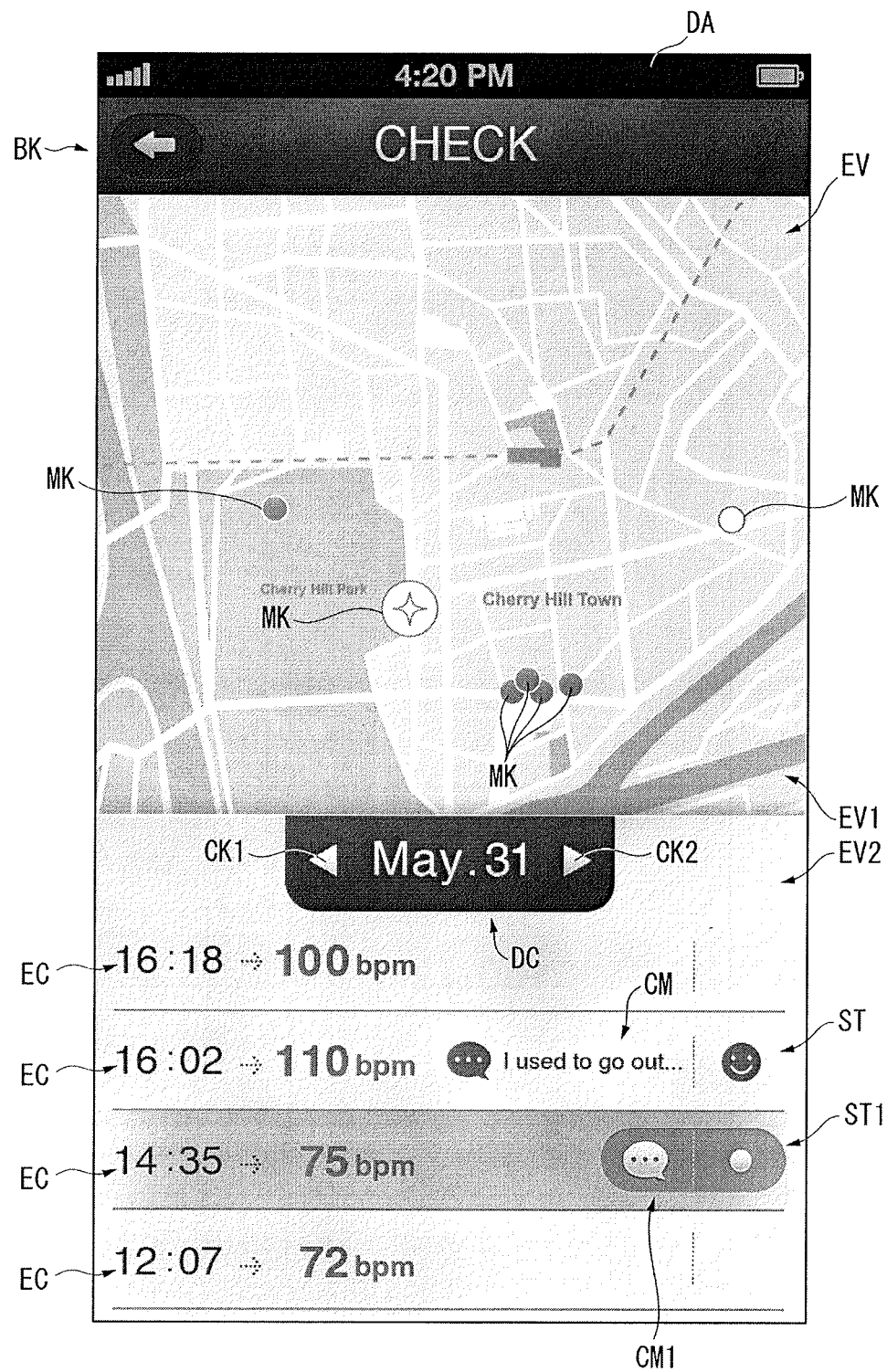
FIG. 38 is a diagram showing the event check screen in the embodiment.
Figure 39:
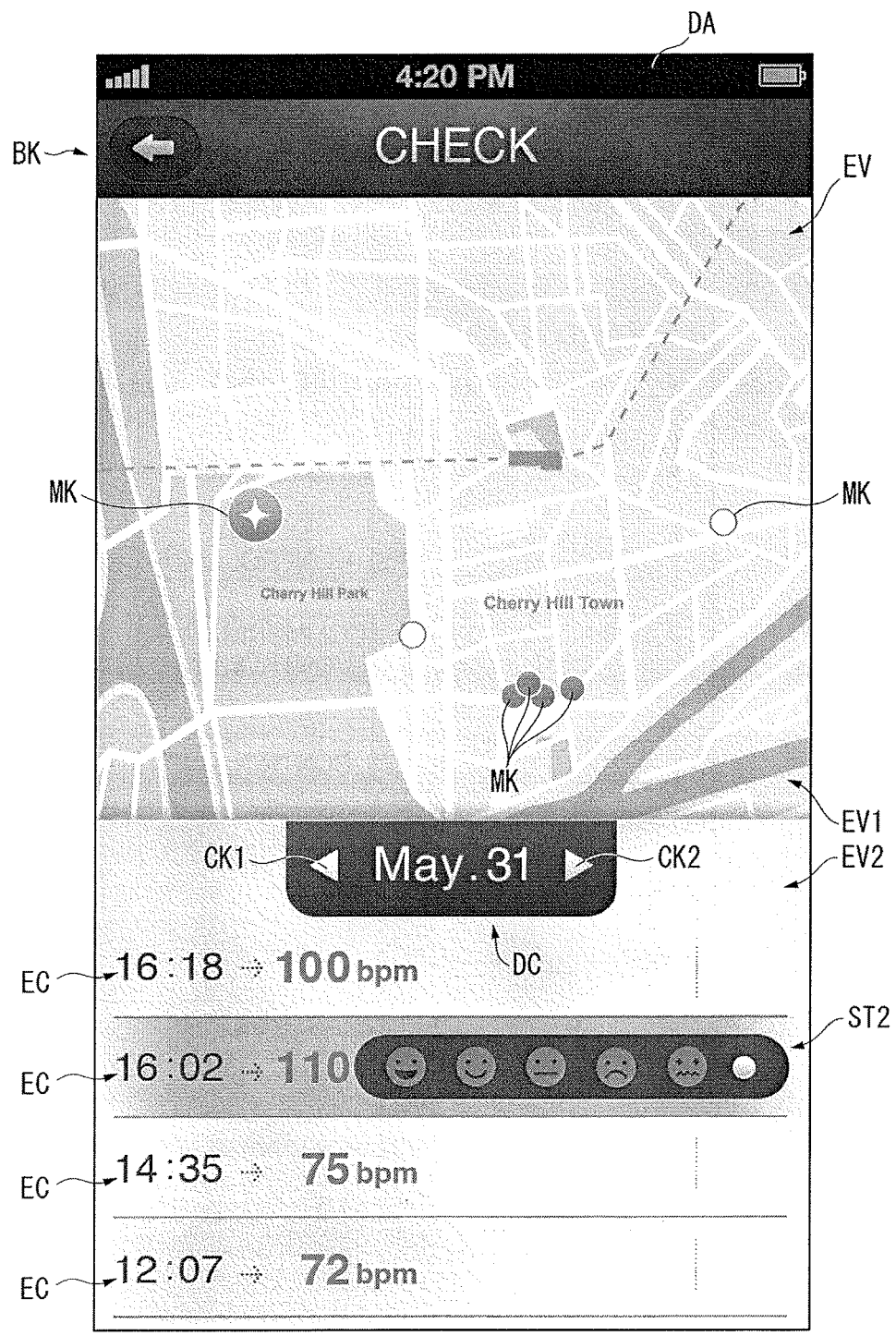
FIG. 39 is a diagram showing the event check screen in the embodiment.

FIGS. 37 to 39 are diagrams showing examples of the event check screen EV.

As explained above, when determining that the user is in the mental state of any one of the excited state due to exercise, the excited state not due to exercise, and the relaxed state, the measuring apparatus 2 communicates with the information terminal 3, transmits measurement information to the information terminal 3, and transmits time of the mental state determination to the information terminal 3.

On the other hand, in the information terminal 3, when the transition key MS2 is pressed, the display control unit 362 causes the display unit 31 to display the event check screen EV shown in FIG. 37.

The event check screen EV is a screen on which a matter that causes the mental state is displayed as an event to cause the user to check the event. On the event check screen EV, the back key BK for returning to the preceding screen, a map display area EV1 in which a map is displayed, the date display area DC where a date of the event is displayed, the cursor keys CK1 and CK2, and a content display area EV2 in which event content is displayed are set.

In the map display area EV1, a map is displayed in which the position of the information terminal 3 (i.e., the position of the user) at event occurrence time (the time of the mental state determination) in a date displayed in the date display area DC is indicated by a marker MK.

The position of the information terminal 3 indicated by the marker MK is determined by position information corresponding to the event occurrence time among kinds of position information acquired by the position acquiring unit 34 and stored in the storing unit 35. Such processing is executed by the main control unit 361. The display control unit 362 sets the marker MK on the map according to a result of the processing.

In this case, the display control unit 362 respectively colors, in different colors, markers MK indicating positions where the user is in the excited state due to exercise, the excited state not due to exercise, and the relaxed state.

In this embodiment, the marker MK added to the position where the user is in the relaxed state is colored in a cold color and is formed as a blue circle. The markers MK added to the position where the user is in the excited state due to exercise and the position where the user is in the excited state not due to exercise are colored in warm colors. The former is formed as a red circle and the latter is formed as an orange circle.

Note that, when any one of event contents displayed in the content display area EV2 is selected by the user, the marker MK in a position corresponding to the selected event content (an occurrence position of an event) is displayed large.

In the content display area EV2, event content on a date displayed in the date display area DC is displayed. For example, in the example shown in FIG. 37, in the content display area EV2, four event contents EC are shown as events that occur on "May 31". The event contents EC include a comment CM and an emotion stamp ST besides time of event occurrence and a pulse rate at the time of the event occurrence.

The user can input the comment CM and the emotion stamp ST. Specifically, when the user presses event content EC scheduled to be edited, as shown in FIG. 38, the event content changes to a selected state and the comment CM and the emotion stamp ST can be input and selected.

When the user presses an input key CM1 of the comment CM, although not shown in the figure, a screen keyboard and a display field for input characters are displayed. When a decision key included in the screen keyboard is pressed, the input characters are set as the comment CM.

When the user presses a selection key ST1 of the emotion stamp ST, as shown in FIG. 39, a selection field ST2 in which a plurality of icons are set is displayed. When any one of the icons is pressed, the pressed icon is set as the emotion stamp ST.

The set comment CM and the set emotion stamp ST are displayed as shown in the event content EC in the second stage in FIG. 38.

When the cursor key CK1 included in the event check screen EV is pressed, the event check screen EV of the preceding day is displayed. When the cursor key CK2 is pressed, the event check screen EV of the following day is displayed.

Contents of the comment CM and the emotion stamp ST are transmitted from the information terminal 3 to the management server 5 and managed by the management server 5 in association with the event content EC.

Note that, when an event occurs on the day, as shown in FIG. 12, an event marker EM for informing the occurrence of the event is displayed above the stress meter M1 in the first position on the main screen MS. During the display of the day detail screen DS11, when an event occurs on a date displayed in the date display area DC, as shown in FIG. 17, the event marker EM is displayed in a position corresponding to event occurrence time in the graph G11. Further, during the display of the week detail screen DS12 and the month detail screen DS13, when an event occurs in a period displayed in the date display area DC, as shown in FIGS. 18 and 19, the event marker EM is displayed in positions corresponding to an event occurrence day in the graphs G12 and G13.

Configuration of Other Information Terminals

In this embodiment, the information terminal 4 is configured by a PC and communicably connected to the measuring apparatus 2 via a cradle (not shown in the figure). The information terminal 4 includes a configuration same as the configuration of the information terminal 3. However, the information terminal 4 is different from the information terminal 3 in a layout of a display screen and in that the information terminal 4 includes a function called friend management function.

Figure 40:
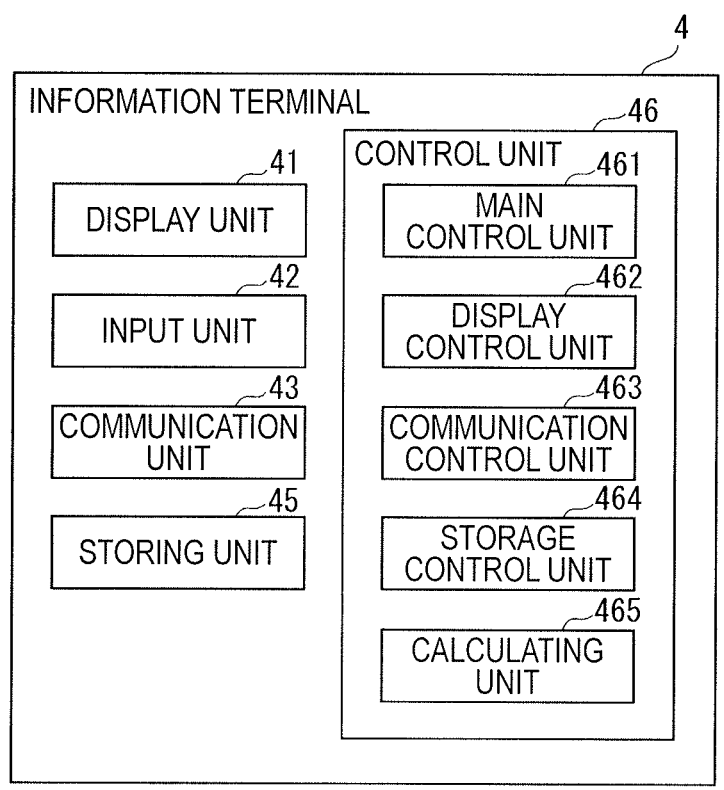
FIG. 40 is a block diagram showing the configuration of an information terminal in the embodiment.

FIG. 40 is a block diagram showing the configuration of the information terminal 4.

The information terminal 4 includes, as shown in FIG. 40, a display unit 41, an input unit 42, a communication unit 43, a storing unit 45, and a control unit 46 including functions same as the functions of the units 31 to 33, 35, and 36 of the information terminal 3. Like the control unit 36, the control unit 46 includes a main control unit 461, a display control unit 462, a communication control unit 463, a storage control unit 464, and a calculating unit 465. That is, in this embodiment, the information terminal 4 is assumed to be a PC arranged in a predetermined place (e.g., an own room of the user) and not always carried. Therefore, the information terminal 4 does not include a component equivalent to the position acquiring unit 34. Therefore, the position acquiring unit 34 may be included in the measuring apparatus 2. Note that the display control unit 462 is equivalent to the display control unit according to the invention in the information terminal 4.

Execution Time Screen

Figure 41:
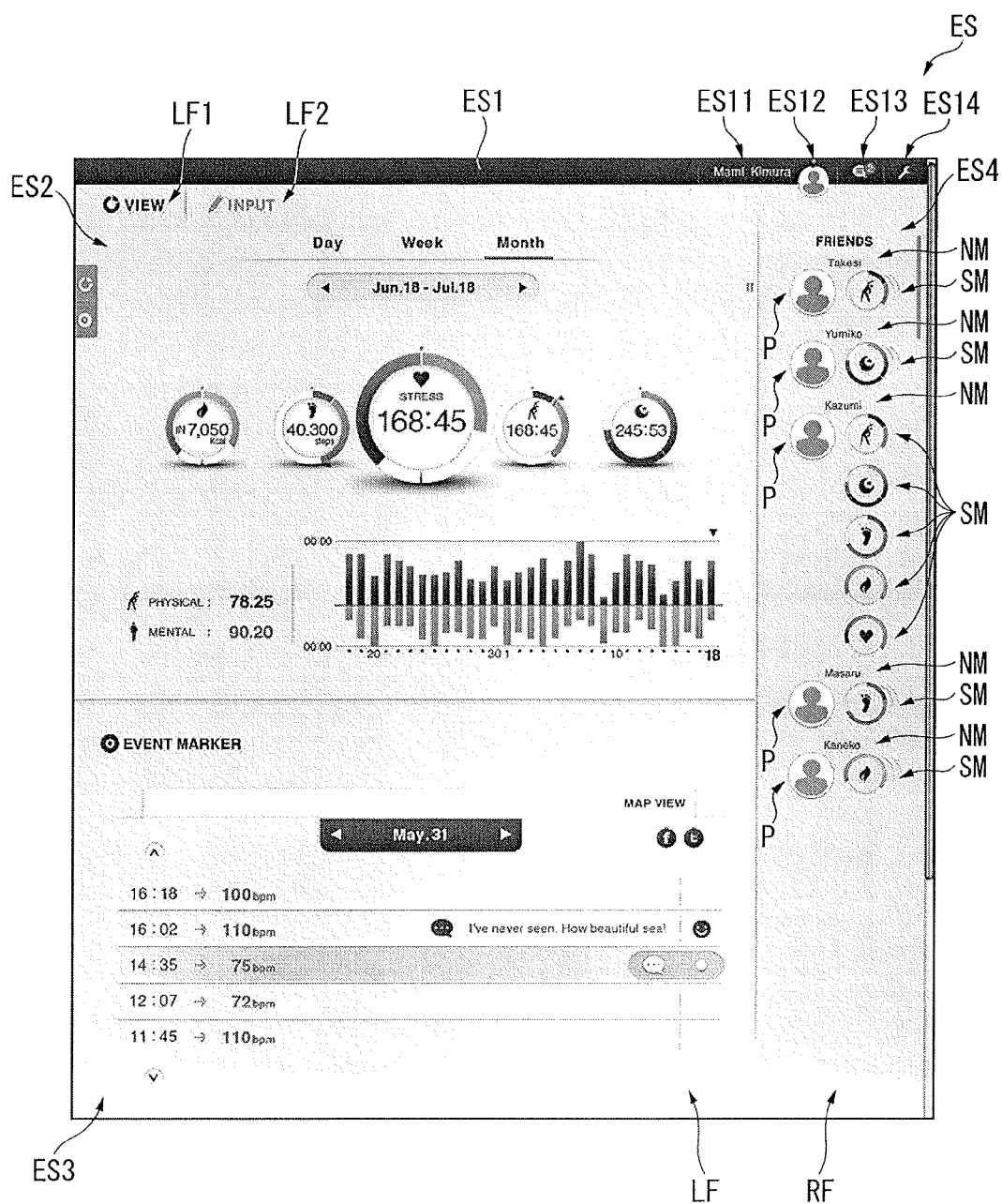
FIG. 41 is a diagram showing an execution time screen in the embodiment.

FIG. 41 is a diagram showing an example of an execution time screen ES of a measurement information management application in the information terminal 4.

In the information terminal 4, when the main control unit 461 executes the measurement information management application stored in the storing unit 45, the display control unit 462 causes the display unit 41 to display the execution time screen ES shown in FIG. 41. The execution time screen ES includes a constant display area ES1 located at the top and a left side area LF and a right side area RF, which are areas below the constant display area ES1.

In the constant display area ES1, a display area ES11 where a user name is displayed, an image display area ES12 where an image of the user is displayed, a message reception icon ES13, and a transition key ES14 are arranged on the right side. In the image display area ES12, an image set in the image setting field RS36 of the setting screen RS3 is displayed. When the transition key ES14 is pressed, although not shown in the figure, a profile setting screen on which a detailed profile can be set is displayed in the left side area LF of the execution time screen ES.

The left side area LF is set wider than the right side area RF. A measurement information display screen ES2 is arranged on the upper side of the left side area LF. An event check screen ES3 is arranged on the lower side of the left side area LF. On the other hand, an other people information display screen ES4 is arranged in the right side area RF.

Measurement Information Display Screen

Figure 42:
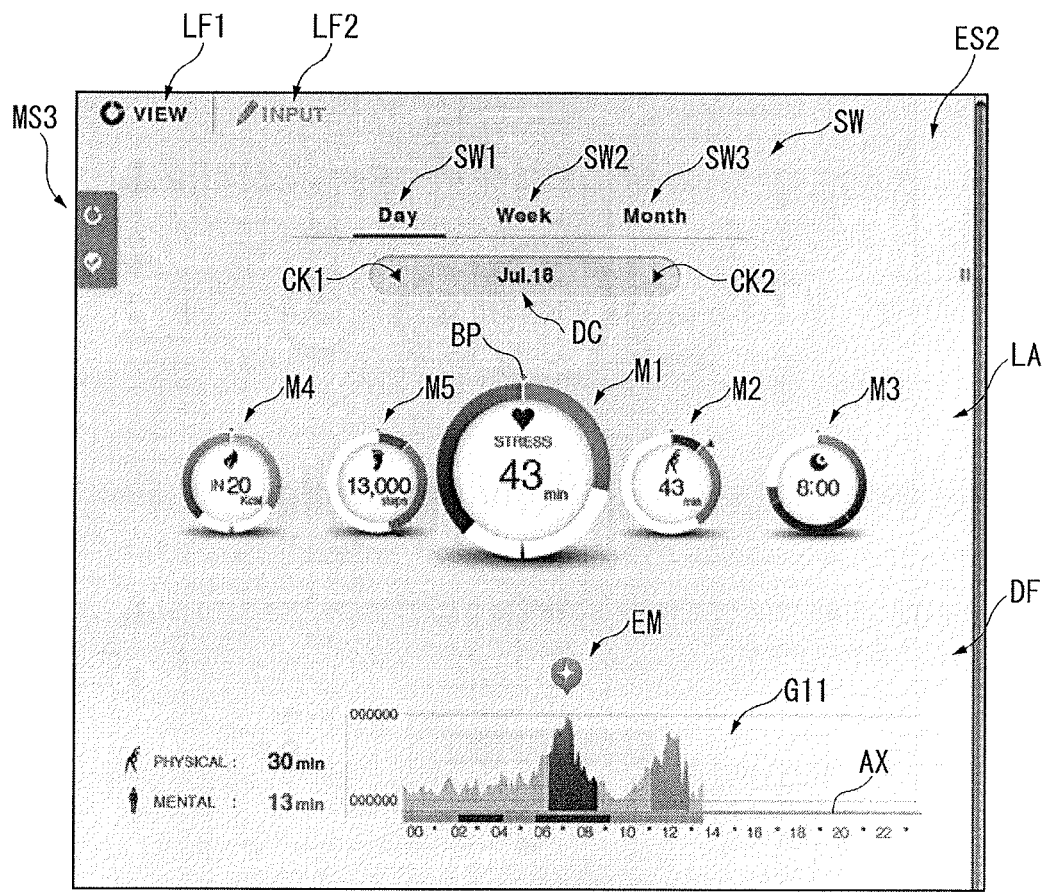
FIG. 42 is a diagram showing a measurement information display screen in the embodiment.
Figure 43:
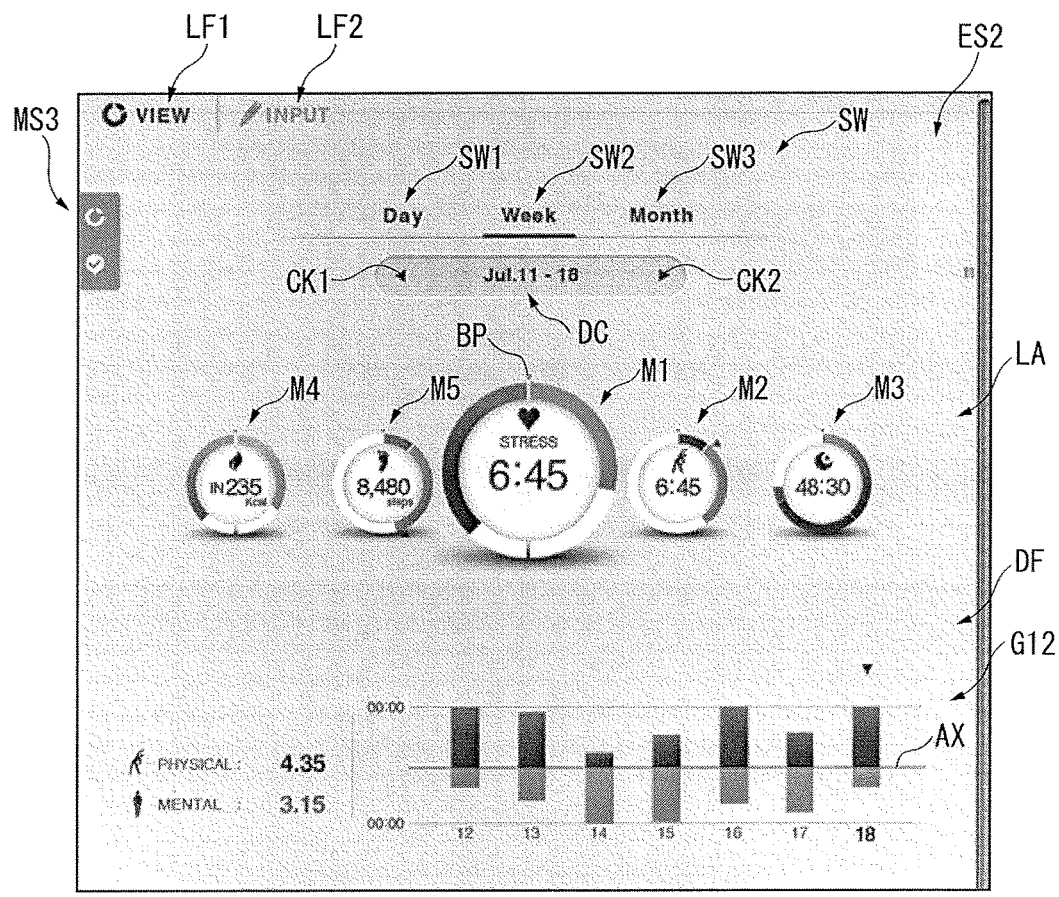
FIG. 43 is a diagram showing the measurement information display screen in the embodiment.
Figure 44:
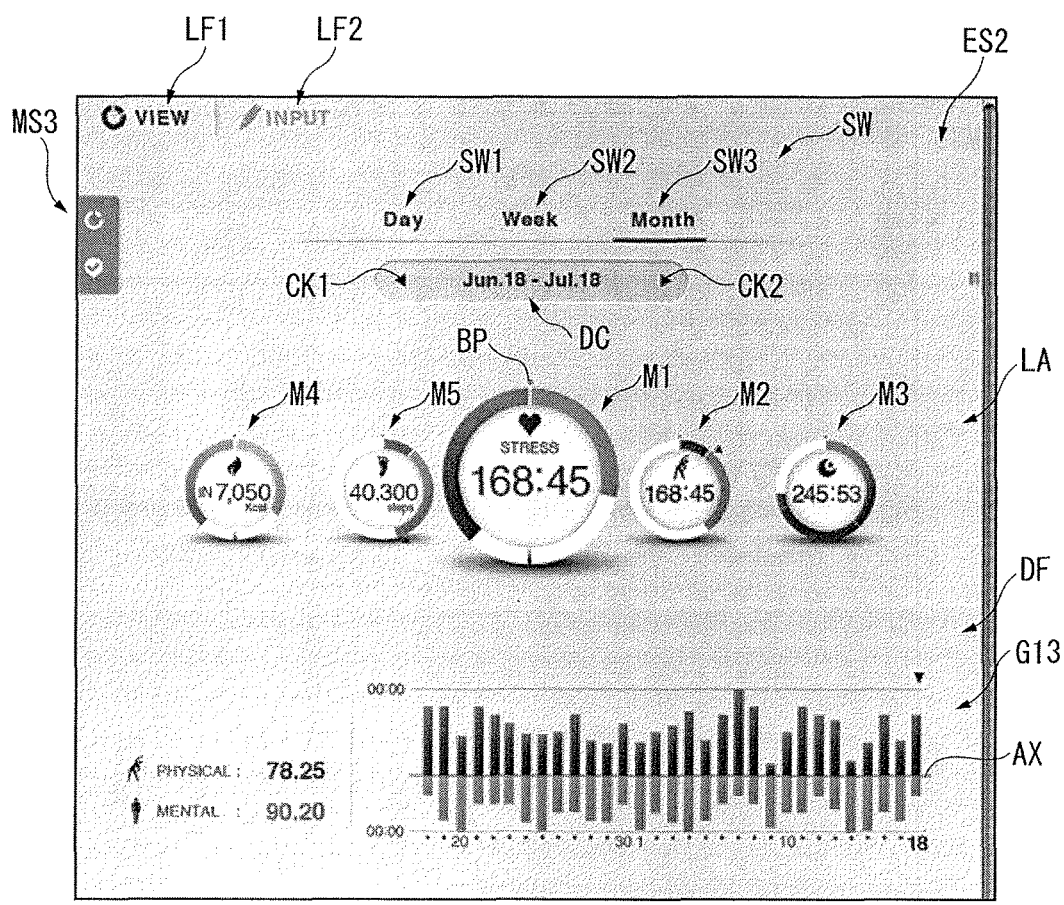
FIG. 44 is a diagram showing the measurement information display screen in the embodiment.

FIGS. 42 to 44 are diagrams showing an example of the measurement information display screen ES2.

On the measurement information display screen ES2, as shown in FIG. 42, contents substantially the same as contents displayed on the main screen MS, the day detail screens, the week detail screens, and the month detail screens in the information terminal 3 are displayed.

Specifically, the display switching field SW, the date display area DC, and the cursor keys CK1 and CK2 are arranged in the upper stage of the measurement information display screen ES2. The meter arrangement area LA is set in the middle stage of the screen ES2. The detail display area DF is set in the lower stage of the screen ES2.

The display switching field SW, the date display area DC, and the cursor keys CK1 and CK2 cause the information terminal 4 to carry out operations same as the operations in the information terminal 3.

In the meter arrangement area LA, the meters M1 to M5 are arranged along the left-right direction.

Specifically, the calorie meter M4, the number-of-steps meter M5, the stress meter M1, the exercise meter M2, and the sleep meter M3 are arranged from the left in order. Among the meters M1 to M5, the meter selected by selection operation by the user is displayed larger than the other meters. Consequently, the user can grasp which meter is selected, that is, data of which item is displayed.

When the area SW1 of the display switching field SW is pressed, information in day units concerning an item of the selected meter is displayed.

For example, in a state in which the stress meter M1 is selected and the area SW1 is pressed, as shown in FIG. 42, an excitement time (an excitement time during exercise and an excitement time during non-exercise) of a date displayed in the date display area DC is indicated by the meter M1. In the detail display area DF, the graph G11 of the date displayed on the day detail screen DS11 is displayed and the excitement time during exercise and the excitement time during non-exercise of the date are displayed.

Operations performed when the cursor keys CK1 and CK2 are pressed in this state are the same as the operations performed during the display of the day detail screen DS11. Information of the preceding day or the following day of the date displayed in the date display area DC is displayed in the stress meter M1 and the detail display area DF.

When the area SW2 of the display switching field SW is pressed, information of the nearest one week, that is, in week units concerning the item of the selected meter is displayed.

For example, in a state in which the stress meter M1 is selected and the area SW2 is pressed, as shown in FIG. 43, a date indicating a period of the nearest one week is displaced in the date display area DC. A total value of excitement times during exercise and a total value of excitement times during non-exercise in the period are indicated by the meter M1. In the detail display area DF, the graph G12, which is a graph of the period and same as the graph G12 on the week detail screen DS12, is displayed. Besides, the total value of the excitement times during exercise and the total value of the excitement times during non-exercise are displayed.

Operations performed when the cursor keys CK1 and CK2 are pressed in this state are the same as the operations performed during the display of the week detail screen DS12. Information of the preceding week or the following week of the period displayed in the date display area DC is displayed in the stress meter M1 and the detail display area DF.

When the area SW3 of the display switching field SW is pressed, information of the nearest one month (thirty days or thirty-one days) concerning the item of the selected meter, that is, information in month units is displayed.

For example, in a state in which the stress meter M1 is selected and the area SW3 is pressed, as shown in FIG. 44, a period of the nearest one month is displayed in the date display area DC. A total value of excitement times during exercise and a total value of excitement times during non-exercise in the period are indicated by the meter M1. In the detail display area DF, the graph G13, which is a graph of the period and same as the graph G13 on the month detail screen DS13, is displayed. Besides, the total value of the excitement times during exercise and the total value of the excitement times during non-exercise in the period are displayed.

Operations performed when the cursor keys CK1 and CK2 are pressed in this state are the same as the operations during the display of the month detail screen DS13. Information of the preceding month or the following month of the period displayed in the date display area DC is displayed in the stress meter M1 and the detail display area DF.

Note that display contents displayed when the other meters are selected are the same.

In this way, contents of the measurement information display screen ES2 displayed in the information terminal 4 are substantially the same as the contents displayed in the information terminal 3. However, a layout of the measurement information display screen ES2 is different. Since the various meters laid out in this way are displayed, information concerning a plurality of items can be grasped at a time. Therefore, the user can analyze a state of the user in a diversified manner. Consequently, the user can review a life style of the user and can examine and determine what kind of a life style is effectively changed for diet, health promotion, and the like.

Note that, when the update key MS3 set in the measurement information display screen ES2 is pressed, as in the operation in the information terminal 3, the main control unit 461 accesses the measuring apparatus 2 via the communication control unit 463 and the communication unit 43 and acquires new measurement information from the measuring apparatus 2. Further, the main control unit 461 accesses the management server 5 and acquires measurement information uploaded anew. When the new measurement information is acquired, calculation by the calculating unit 465 is performed. The display control unit 462 updates display contents of the measurement information display screen ES2 on the basis of the acquired measurement information and a calculation result by the calculating unit 465.

Input Screen

Figure 45:
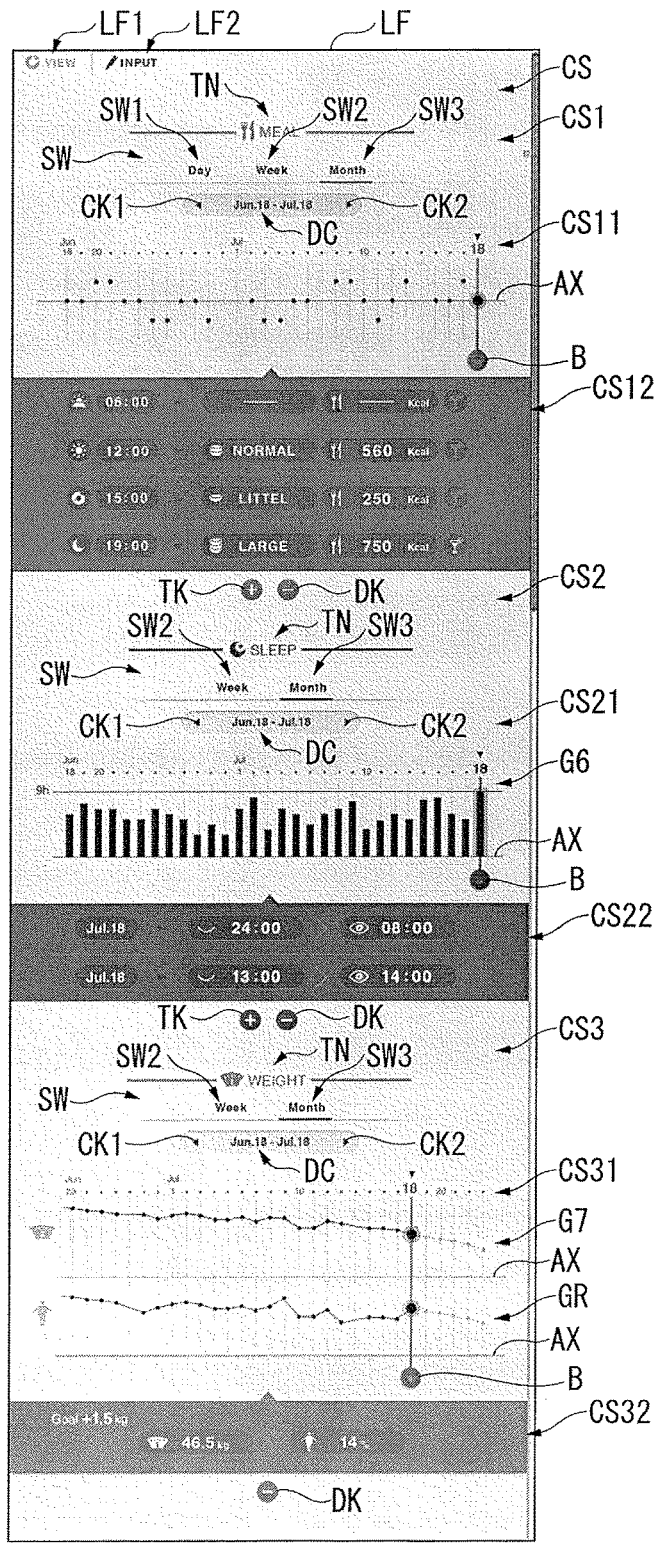
FIG. 45 is a diagram showing an input screen in the embodiment.
Figure 46:
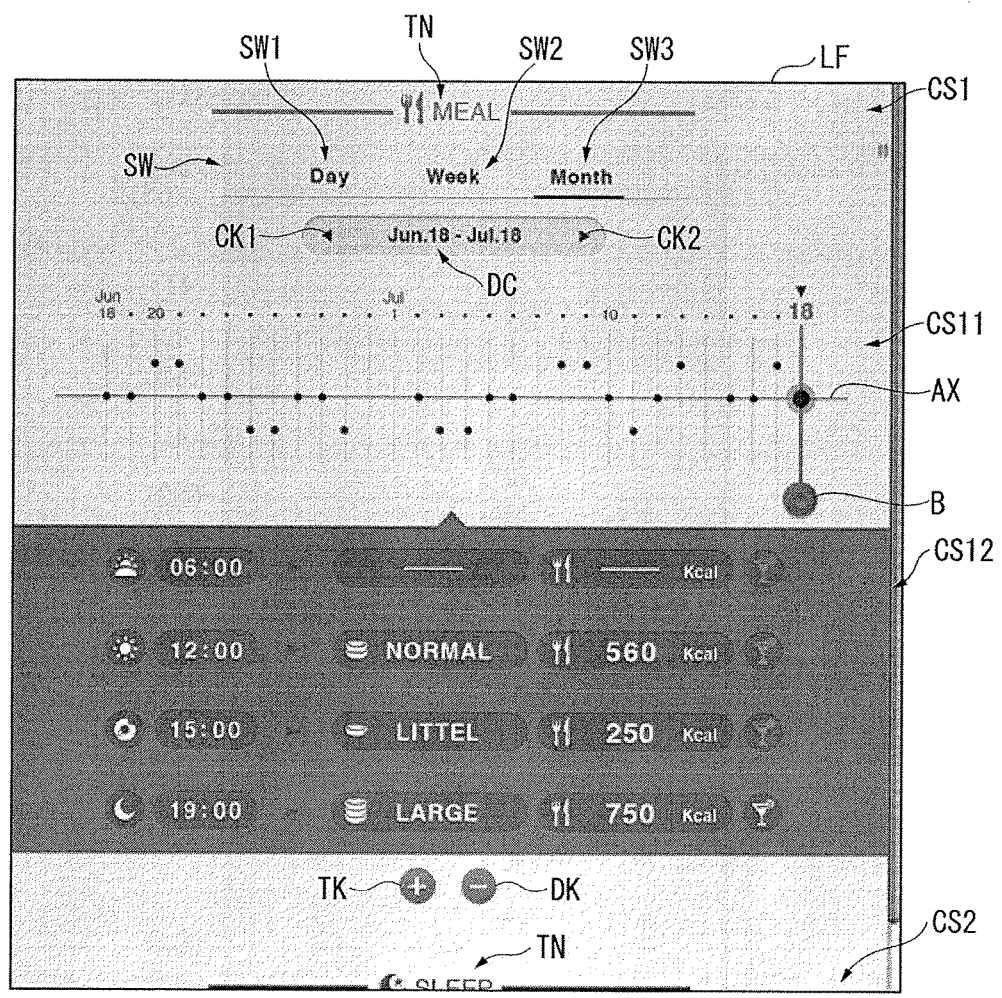
FIG. 46 is a diagram showing the input screen in the embodiment.
Figure 47:
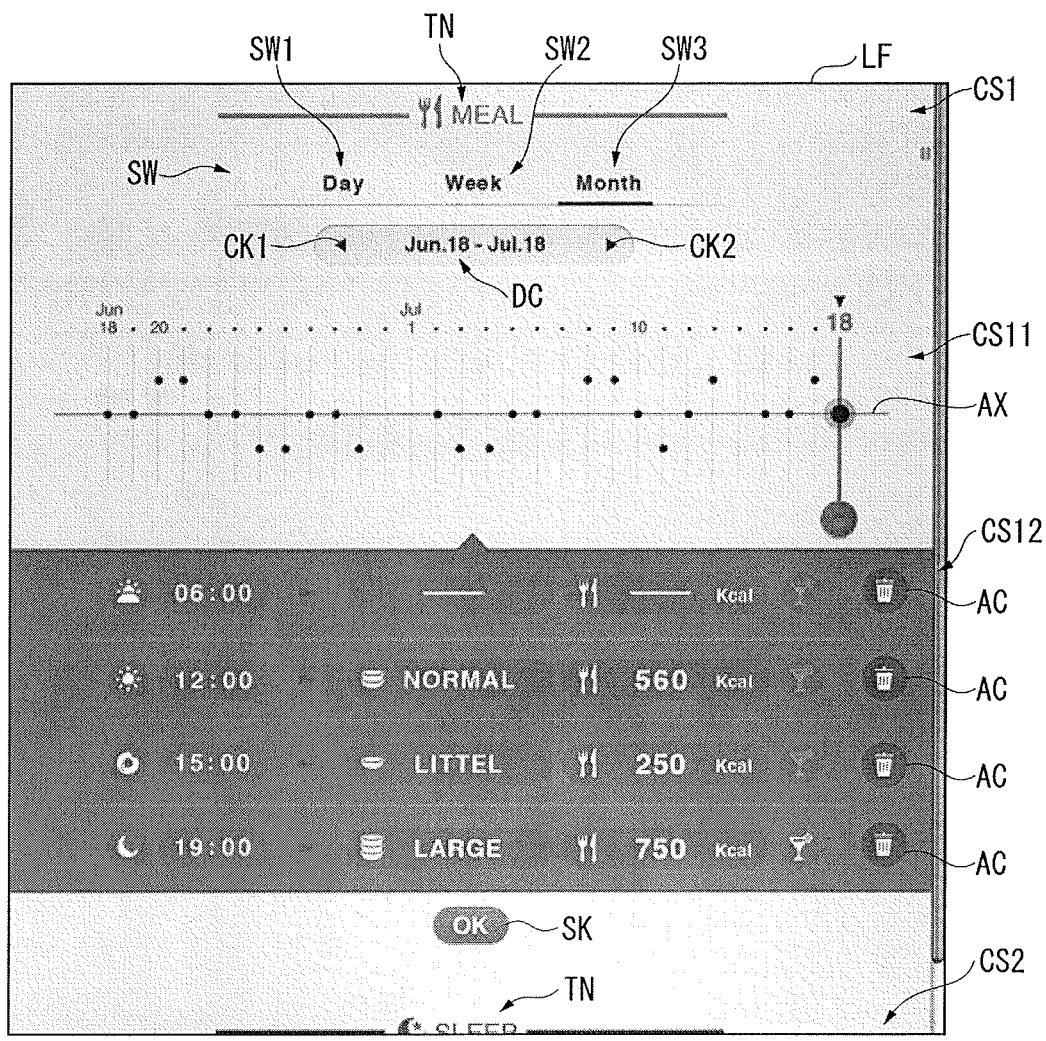
FIG. 47 is a diagram showing the input screen in the embodiment.

FIGS. 45 to 47 are diagrams showing an example of an input screen CS displayed in the information terminal 4.

Of areas LF1 and LF2 arranged at the upper left corner of the left side area LF, when the area LF2 inscribed as "INPUT" is pressed, the input screen CS shown in FIG. 45 is displayed in the entire left side area LF.

The input screen CS is a vertically long screen including a configuration same as the configuration of the input screen ED displayed in the information terminal 3. On the input screen CS, a meal registration area CS1, a sleep time editing area CS2, and a weight registration area CS3 are set in order from the top. On the input screen CS, operation is performed by dragging operation or scrolling operation from one side to the other side in the up-down direction to display any one of the areas CS1 to CS3.

The meal registration area CS1 is a setting area including the item name TN inscribed as "MEAL" and is an area where daily meal information is registered. In the meal registration area CS1, as in the meal registration area ED1, the display switching field SW, the date display area DC, and the cursor keys CK1 and CK2 are set. Besides, in the meal registration area CS1, a variable display area CS11, display content of which is switched according to pressing of any one of the areas SW1 to SW3 of the display switching field SW, a content display area CS12, the addition key TK, and the deletion key DK are set.

Note that display contents of variable display areas CS11 and content display areas CS12 in day units, week units, and month units are the same as the display contents of the meal registration area ED1. Therefore, explanation of the display contents is omitted.

As shown in FIG. 46, during the display of the meal registration area CS1 in month units, in deleting registered meal information, first, the user presses the deletion key DK. Then, as shown in FIG. 47, icons AC imitating a trash can are displayed on the right side of meal information (registered meal information) displayed in the content display area CS12. In a state in which the icon AC is pressed, when a decision key SK displayed below the content display area CS12 and inscribed as "OK" is pressed, meal information corresponding to the pressed icon AC is deleted. Information indicating the deletion of the meal information is transmitted to the management server 5. Corresponding meal information is deleted also deleted in the management server 5. Thereafter, the display content returns to the meal registration area CS1 in month units.

Note that the same applies when registered meal information is deleted during the display of the meal registration area CS1 in week units.

The sleep time editing area CS2 is a setting area including the item name TN inscribed as "SLEEP". The sleep time editing area CS2 is the same as the sleep time editing area ED2. The display switching field SW including the areas SW2 and SW3, the date display area DC, and the cursor keys CK1 and CK2 are set in the sleep time editing area CS2.

Besides, in the sleep time editing area CS2, a variable display area CS21 in which display in week units and display in month units are switched according to pressing of any one of the areas SW2 and SW3, a content display area CS22, the addition key TK, and the deletion key DK are set.

The graph G6 is displayed in the variable display area CS21. In the content display area CS22, start time and end time of sleep on a date selected by the bar B are displayed. The operation of the sleep time editing area CS2 is the same as the operation of the sleep time editing area ED2.

The weight registration area CS3 is a setting area including the item name TN inscribed as "WEIGHT". In the weight registration area CS3, as in the weight registration area ED3, the display switching field SW including the areas SW2 and SW3, the date display area DC, the cursor keys CK1 and CK2, a variable display area CS31 in which display in week units and display in month units are switched according to pressing of any one of the areas SW2 and SW3, a content display area CS32, and the deletion key DK are set.

In the variable display area CS31, besides the graph G7, a graph GR, which is a line graph, indicating a change in body fat is displayed. The time axes AX of the graphs G7 and GR coincide with each other.

In the content display area CS32, a difference between weight and a target is displayed and weight and a fat rate of a date selected by the bar B are displayed. When a date when weight and a fat rate are not set is selected by the bar B, the weight and the fat rate of the date can be input. Already registered weight and body fat of a date can be deleted by pressing the deletion key DK.

Note that, on the input screen CS, a dimension in the longitudinal direction of each of the areas CS1 to CS3 is smaller than a dimension in the longitudinal direction of the left side area LF.

The information registered and edited on the input screen CS is acquired by the main control unit 461 and stored in the storing unit 45. Further, the information is transmitted to the management server 5 via the communication unit 43 and stored in the management server 5.

Note that, during the display of the input screen CS, when the area LF1 inscribed as "VIEW" is pressed, the input screen CS is hidden and the display content of the left side area LF is switched to the measurement information display screen ES2 and the event check screen ES3. In this case, display content of the measurement information display screen ES2 reflects the information registered and edited on the input screen CS. When the input screen CS is displayed again, as on the input screen ED, the area (any one of the areas CS1 to CS3) displayed during the last display is displayed on the input screen CS.

Event Check Screen

FIGS. 48 to 52 are diagrams showing examples of the event check screen ES3.

The event check screen ES3 includes a configuration same as the configuration of the event check screen EV and displays contents (event contents) same as the contents displayed on the event check screen EV.

Figure 48:
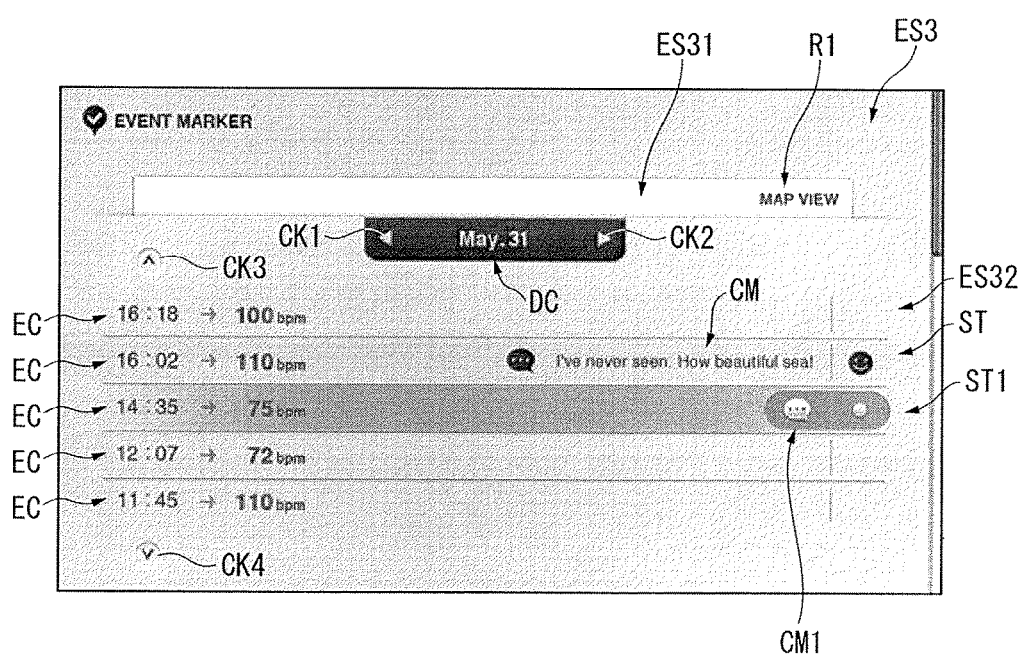
FIG. 48 is a diagram showing an event check screen in the embodiment.

Specifically, on the event check screen ES3, as shown in FIG. 48, a map display area ES31 is set in the upper stage, the date display area DC and the cursor keys CK1 and CK2 are set in the middle stage, and a content display area ES32 is set in the lower stage.

Event contents EC generated on a date displayed in the date display area DC are displayed in the content display area ES32 in order of occurrence times of events. Note that, in this embodiment, five event contents EC can be displayed in the content display area ES32. When five or more event contents EC are registered, up-down cursor keys CK3 and CK4 are displayed in the content display area ES32. When the cursor keys CK3 and CK4 are pressed, the event contents EC not displayed in the content display area ES32 are displayed.

In the event contents EC, as on the event check screen EV, the comment CM and the emotion stamp ST can be set.

Specifically, on the event check screen ES3 shown in FIG. 48, the comment CM and the emotion stamp ST are set in the event content EC displayed in the second stage in the content display area ES32.

Figure 49:
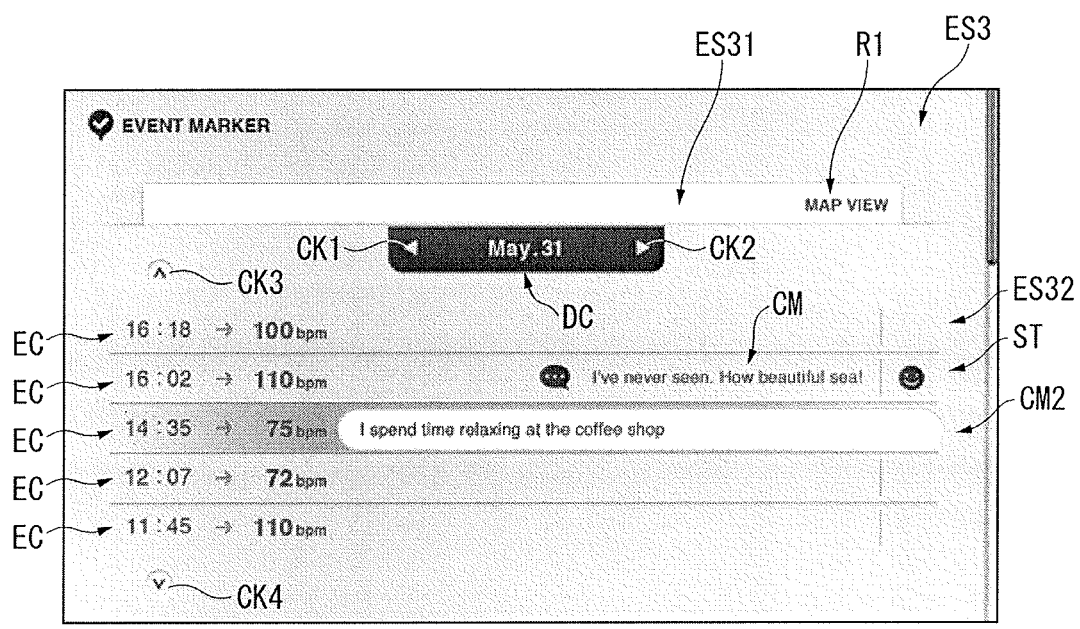
FIG. 49 is a diagram showing the event check screen in the embodiment.

In setting the comment CM, after selecting the target event content EC, the user presses the input key CM1 of the comment CM. An input field CM2 of the comment CM is displayed as shown in FIG. 49 according to the pressing of the input key CM1. When the user inputs comment content to the input field CM2 and closes the input field CM2, the input content is set as the comment CM.

Figure 50:
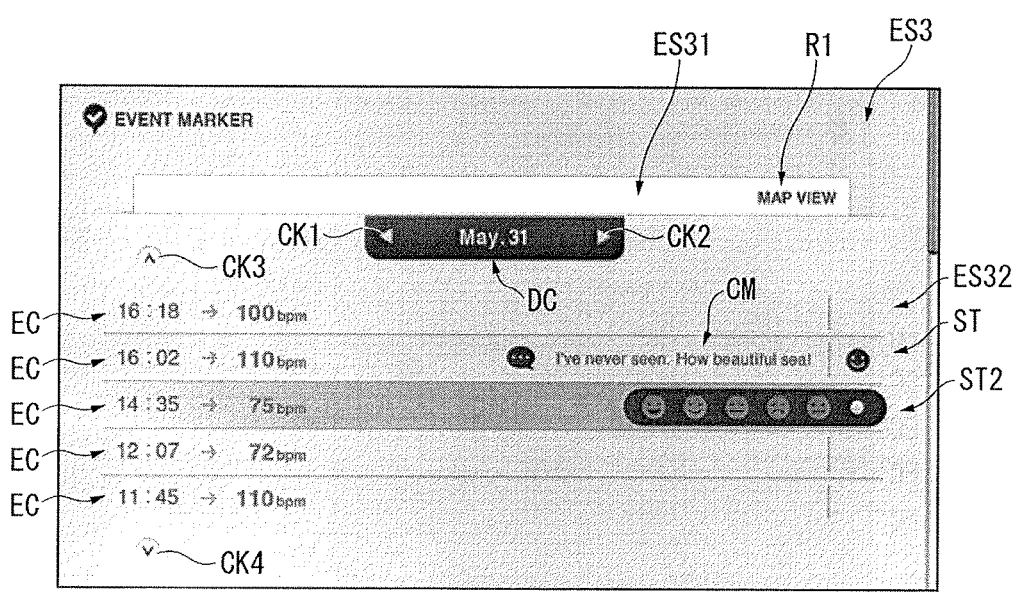
FIG. 50 is a diagram showing the event check screen in the embodiment.

In setting the emotion stamp ST, after selecting the target event content EC, the user presses the selection key ST1 of the emotion stamp ST. The selection field ST2 in which a plurality of icons are set is displayed as shown in FIG. 50 according to the pressing of the selection key ST1. When any one of the icons is pressed, the pressed icon is set as the emotion stamp ST.

Figure 51:
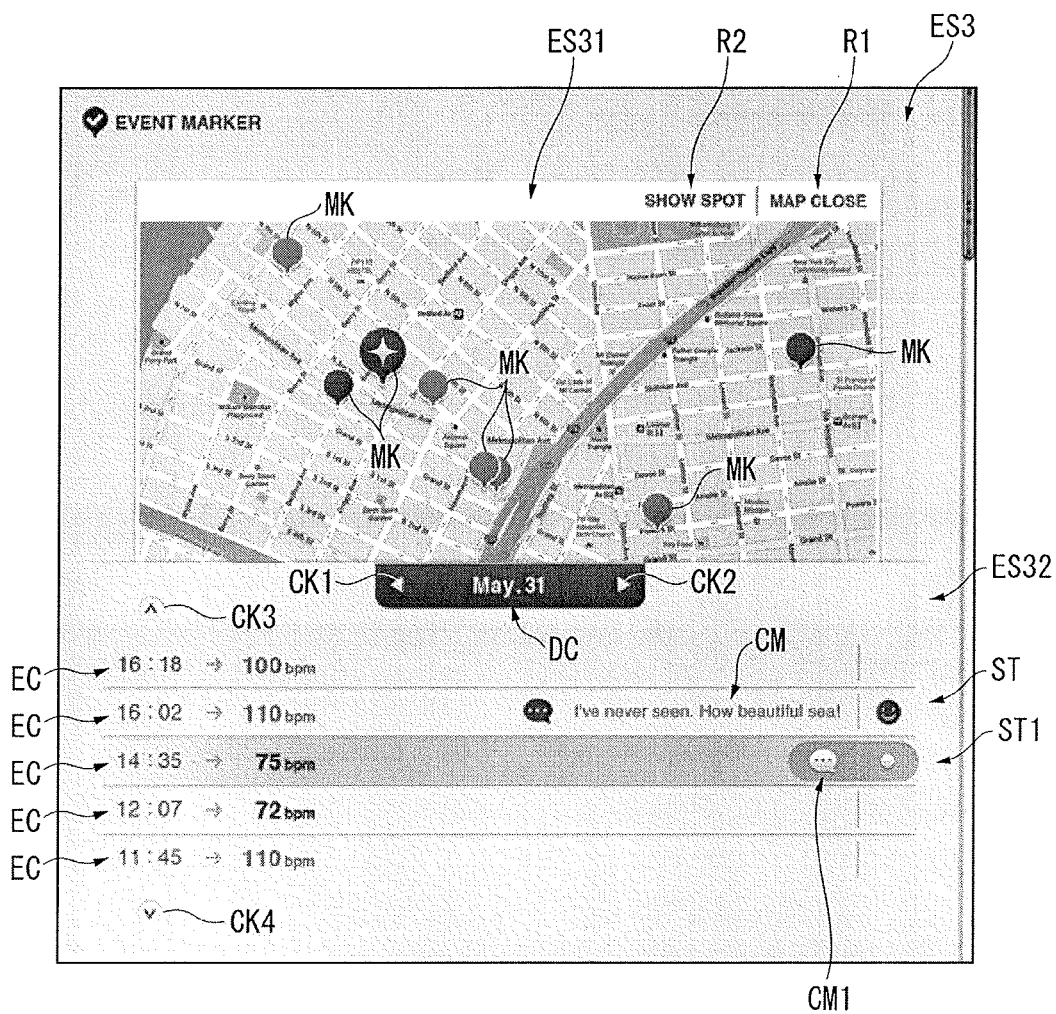
FIG. 51 is a diagram showing the event check screen in the embodiment.

In the map display area ES31, when an area R1 inscribed as "MAP VIEW" is pressed, the map display area ES31 is expanded downward. As shown in FIG. 51, a map same as the map displayed in the map display area EV1 is displayed. The inscription of the area R1 is changed to "MAP CLOSE". An area R2" inscribed as "SHOW SPOT" is displayed on the left side of the area R1.

Note that, in the map displayed in the map display area ES31, the markers MK same as the markers MK in the map displayed in the map display area EV1 are set. As explained above, the markers MK are color-coded according to event contents corresponding thereto. The marker MK corresponding to the event content EC selected in the content display area ES32 is displayed large compared with the other markers MK.

Note that the position of the marker MK set on the map, that is, the position of the user during event occurrence is based on information transmitted to the management server 5 by the information terminal 3. Position information indicating the position is simultaneously acquired when the measurement information is acquired from the management server 5.

Figure 52:
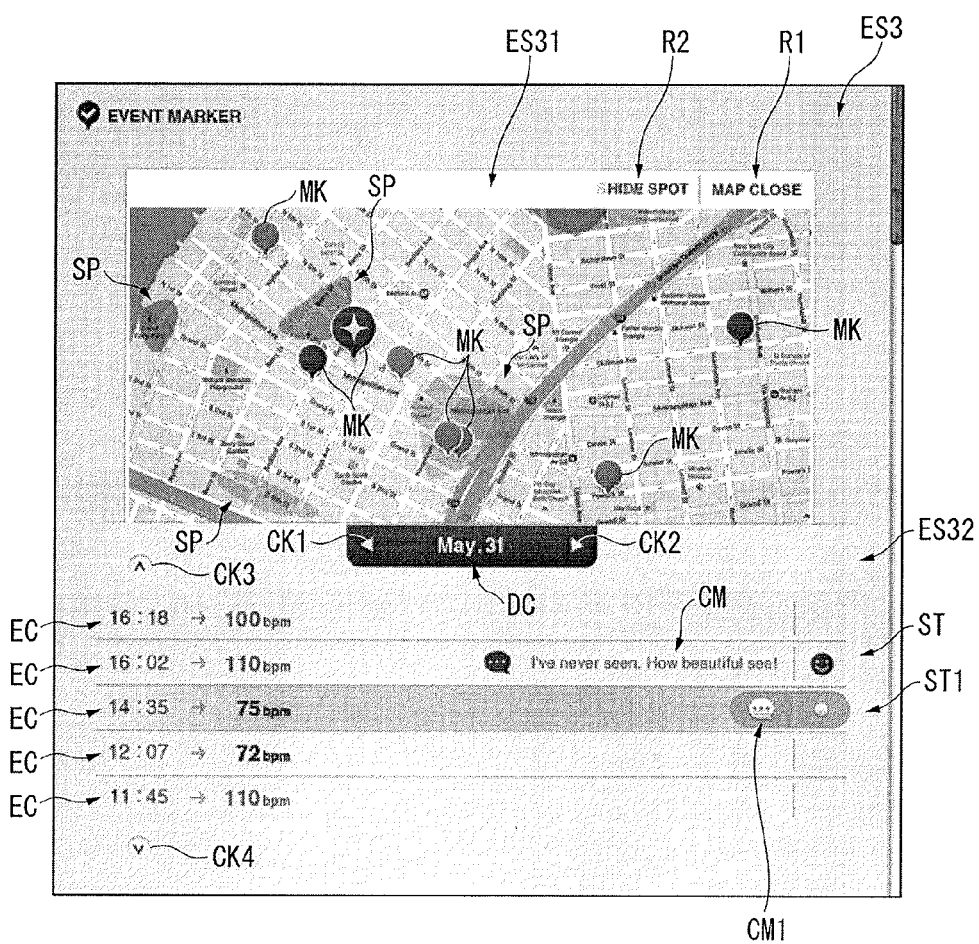
FIG. 52 is a diagram showing the event check screen in the embodiment.

When an area R2 is pressed in a state in which the map is displayed in the map display area ES31, as shown in FIG. 52, the inscription of the area R2 is changed to "HIDE SPOT" and spots SP are displayed on the displayed map. The spots SP are areas indicating positions where events occur at a relatively high frequency among positions during event occurrence of other people managed by the management server 5.

The positions of the spots SP are transmitted from the management server 5 to the information terminal 4 together with measurement information and set on the map and displayed by the display control unit 462.

Note that the spots SP are also color-coded to a cold color, a warm color, and the like according to the event contents EC corresponding thereto and displayed.

When the area R2 is pressed, the displayed spots SP are hidden. When the area R1 inscribed as "MAP CLOSE" is pressed, as shown in FIG. 48, the map display area ES31 is reduced to the upper side and the map is hidden.

Note that the contents of the comments CM input on the event check screen ES3 and the event check screen EV can be automatically reflected on a simplified posting Web site, a Web page, and the like. In this case, for example, position information included in the event contents EC attached with the comments CM and contents of the comments CM may be reflected on the site and the Web page.

Other People Information Display Screen

As shown in FIG. 41, the other people information display screen ES4 is arranged in the right side area RF on the execution time screen ES. On the other people information display screen ES4, information concerning other users registered as friends by a friend management function explained below is displayed.

Specifically, on the other people information display screen ES4, user names NM of the other people registered as friends, images P of the other people, and the symbol marks SM of the meters disclosed by the other people are displayed. Note that, when another person discloses a plurality meters, the symbol marks SM are superimposed and displayed like "Takeshi" in FIG. 41. However, when the user presses the image P of the other person, the symbol marks SM are expanded like the symbol marks SM of "Kazumi" in FIG. 41. When the user further presses the image P, the symbol marks SM are superimposed again. When the user presses the expanded symbol mark SM, the meter corresponding to the symbol mark SM disclosed by the other person corresponding to the symbol mark SM is displayed.

Note that, when another person discloses a plurality of meters and the symbol marks SM corresponding to the plurality of meters are superimposed and displayed, the symbol mark SM displayed closest to the user's side can be configured to capable of being set for each of the other people.

Friend Management Function

FIGS. 53 to 63 are diagrams for explaining the friend management function.

The friend management function is explained below.

The friend management function is a function of setting, as "friends", desired users among users other than the user registered in the management server 5, disclosing contents indicated by the meters and contents of the events to the users, and enabling information disclosed by the user to be viewed. With the function, it is possible to cause the respective users to be conscious of, for example, concentrating on diet.

Procedure of Friend Application/Registration

To enable the friend management function and setting the other users as "friends", the user presses the transition key ES14 arranged in the constant display area ES1 (see FIG. 41) to display a profile setting screen. The user displays a friend management screen FS shown in FIG. 53 included in the profile setting screen and inscribed as "SHARED METER".

On the friend management screen FS, in a field FS1 inscribed as "My Share", a symbol mark SM6 concerning the events is set besides symbol marks SM1 to SM5 corresponding to the meters M1 to M5.

The symbol marks SM1 to SM6 are symbol marks for setting whether the meters M1 to M5 and event contents EC are disclosed to other people. Every time the respective symbol marks SM1 to SM6 is pressed, colors of the symbol marks SM1 to SM6 are reversed. If the symbol marks SM1 to SM6 are displayed in bright colors, this indicates that contents corresponding to the symbol marks SM1 to SM6 are set to be disclosed to other people (other users) registered as friends. If the symbol marks SM1 to SM6 are displayed in dark colors, this indicates that the contents are set to be not disclosed.

Figure 53:
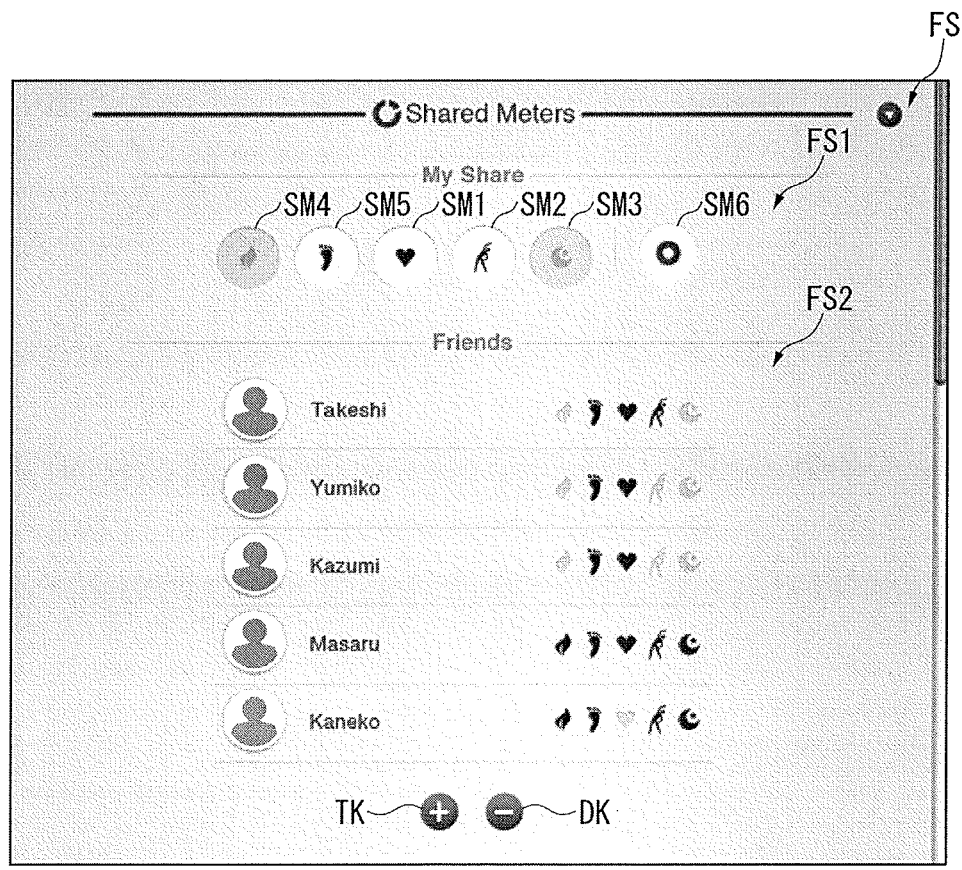
FIG. 53 is a diagram showing a friend management screen in the embodiment.

Therefore, for example, on the friend management screen FS shown in FIG. 53, the symbol marks SM1, SM2, SM5, and SM6 are displayed in bright colors and the symbol marks SM3 and SM4 are displayed in dark colors. Therefore, contents of the meters M1, M2, and M5 and the event contents EC are set to be disclosed to the other people registered as friends and contents of the meters M3 and M4 are set to be not disclosed.

On the friend management screen FS, information concerning other people already registered as friends is displayed in a field FS2 inscribed as "Friends".

In an example shown in FIG. 53, information concerning five people registered as friends is displayed in the field FS2. As the information, the images P, the user names NM, and the symbol marks SM indicating disclosed contents of the people are set. For example, the symbol marks SM1 and SM5 of "Kazumi", who is one of the five people, are displayed in bright colors. This indicates that "Kazumi" discloses contents of the stress meter M1 and the number-of-steps meter M5.

The disclosed contents of the people are linked to displayed contents on the other people information display screen ES4. The information concerning the other people registered as friends is acquired from the management server 5.

Figure 54:
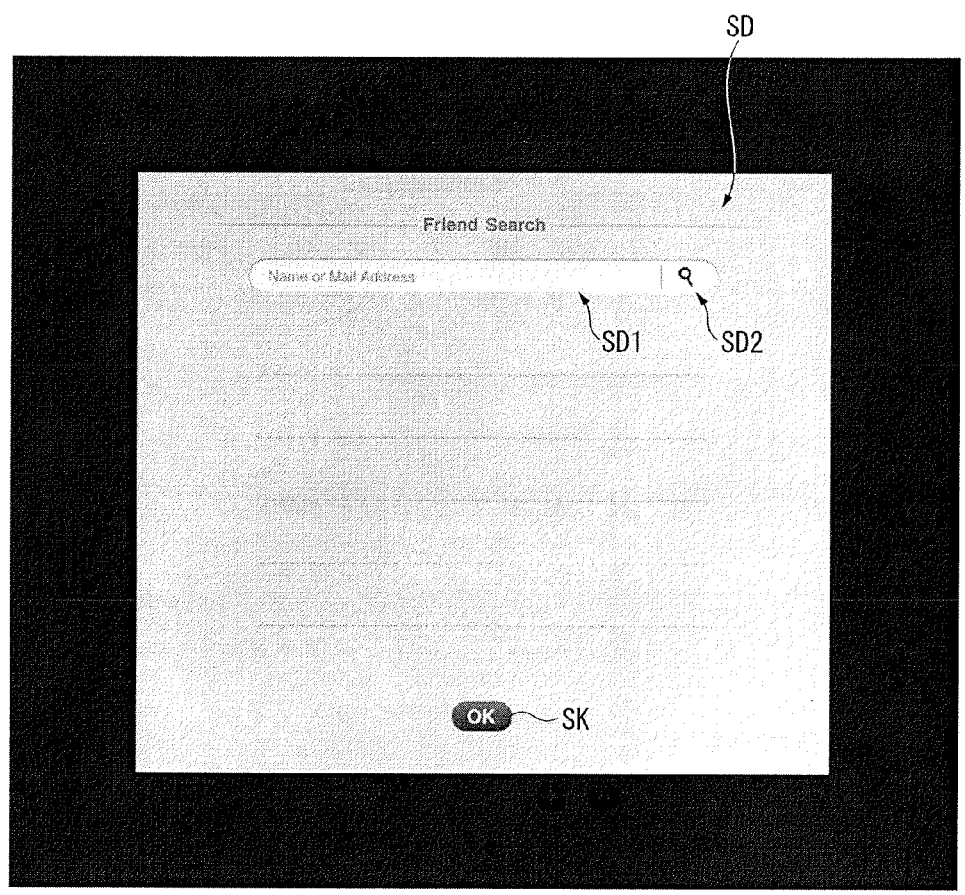
FIG. 54 is a diagram showing a search dialog in the embodiment.

When the user desires to add another person to be registered as a friend, the user enters the addition key TK arranged in a lower part of the friend management screen FS. When the addition key TK is entered, a search dialog SD shown in FIG. 54 is displayed.

In the search dialog SD, an input field SD1 to which a user name or an E-mail address of search target another person is input, a search execution key SD2, and a decision key SK are arranged. Note that, when the decision key SK is pressed, the search dialog SD is hidden.

Figure 55:
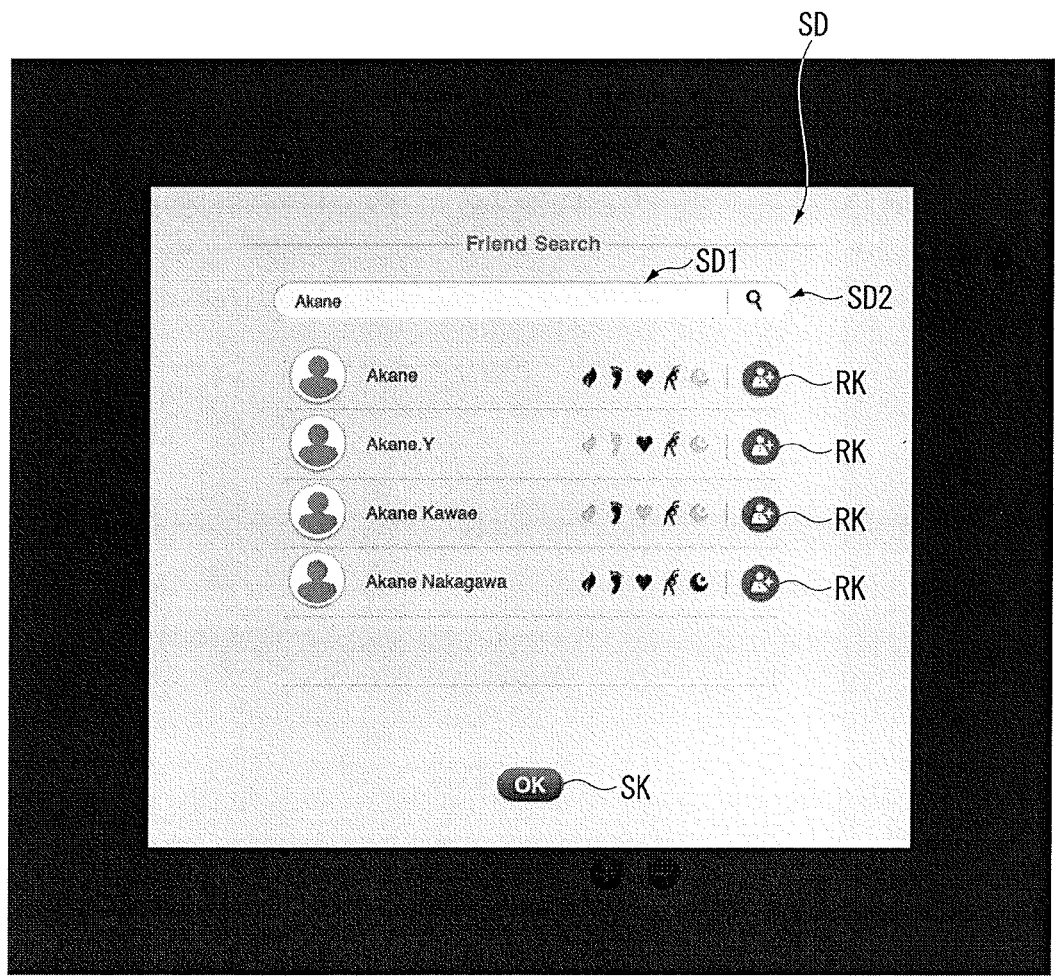
FIG. 55 is a diagram showing the search dialog in the embodiment.

For example, when "Akane" is input to the input field SD1 as a user name, when the search execution key SD2 is pressed, the information terminal 4 communicates with the management server 5 and acquires information concerning users including the user name. As shown in FIG. 55, the information terminal 4 displays the information concerning the pertinent users in the search dialog SD and displays request keys RK on the right side of the respective kinds of user information.

Note that, an example shown in FIG. 55, as the information concerning the users, the images and the user names of the users are displayed. Further, the symbol marks SM1 to SM5 of the meters disclosed by the users are displayed in bright colors.

Figure 56:
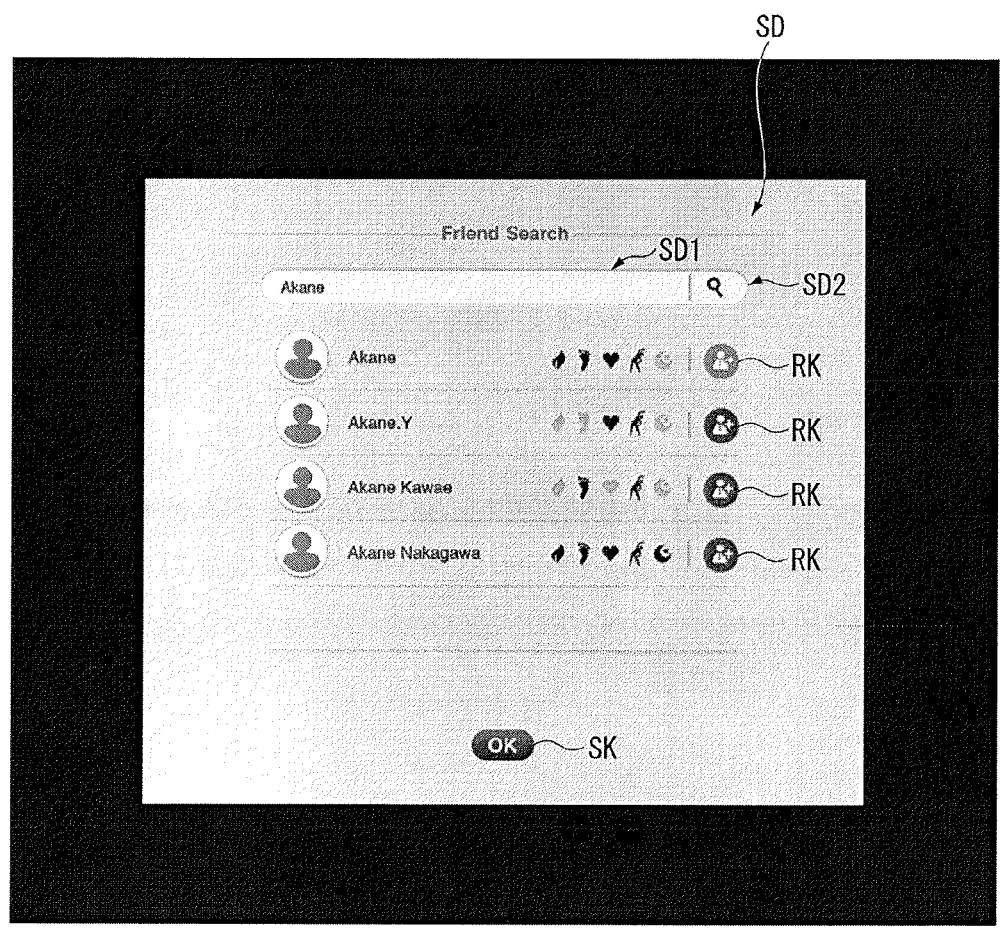
FIG. 56 is a diagram showing the search dialog in the embodiment.

When the displayed request key RK is pressed, as shown in FIG. 56, the pressed request key RK is changed. Note that, in an example shown in FIG. 56, the request key RK of "Akane" is pressed and changed.

Figure 57:
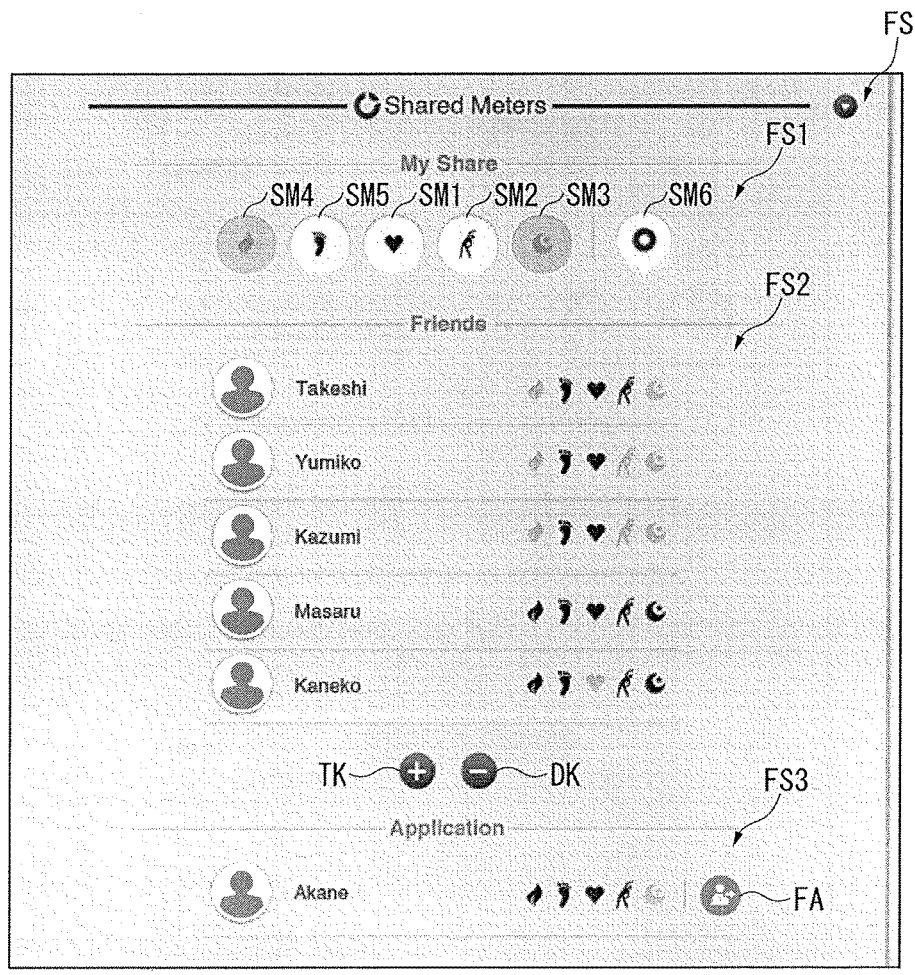
FIG. 57 is a diagram showing the friend management screen in the embodiment.

Subsequently, when the decision key SK is pressed, the search dialog SD is hidden and the screen display returns to the friend management screen FS. On the friend management screen FS in this state, as shown in FIG. 57, a field FS3 inscribed as "Application" is added. In the field FS3, information concerning the user whose request key RK is pressed in the search dialog SD and the icon FA indicating that the user is currently under friend application are displayed. In this state, the information terminal 4 transmits, to the management server 5, a transmission request for a friend application message to the other person corresponding to the request key RK pressed in the search dialog SD. The management server 5 transmits the friend application message to the corresponding user. Consequently, for example, in the example explained above, the friend application message is transmitted to "Akane".

Thereafter, when the other person, to whom the friend application message is transmitted, permits friend registration, although not shown in the figure, in the field FS2 of the friend management screen FS, information concerning the user whose friend application is permitted is added.

Procedure of Friend Registration by Reception of a Request

When the information terminal 4 receives a message such as a friend application message of another person from the management server 5, as shown in FIG. 41, the information terminal 4 displays the number of an unread messages in the message reception icon ES13. For example, in an example shown in FIG. 41, since there are two unread messages, "2" is displayed in the icon ES13.

Figure 58:
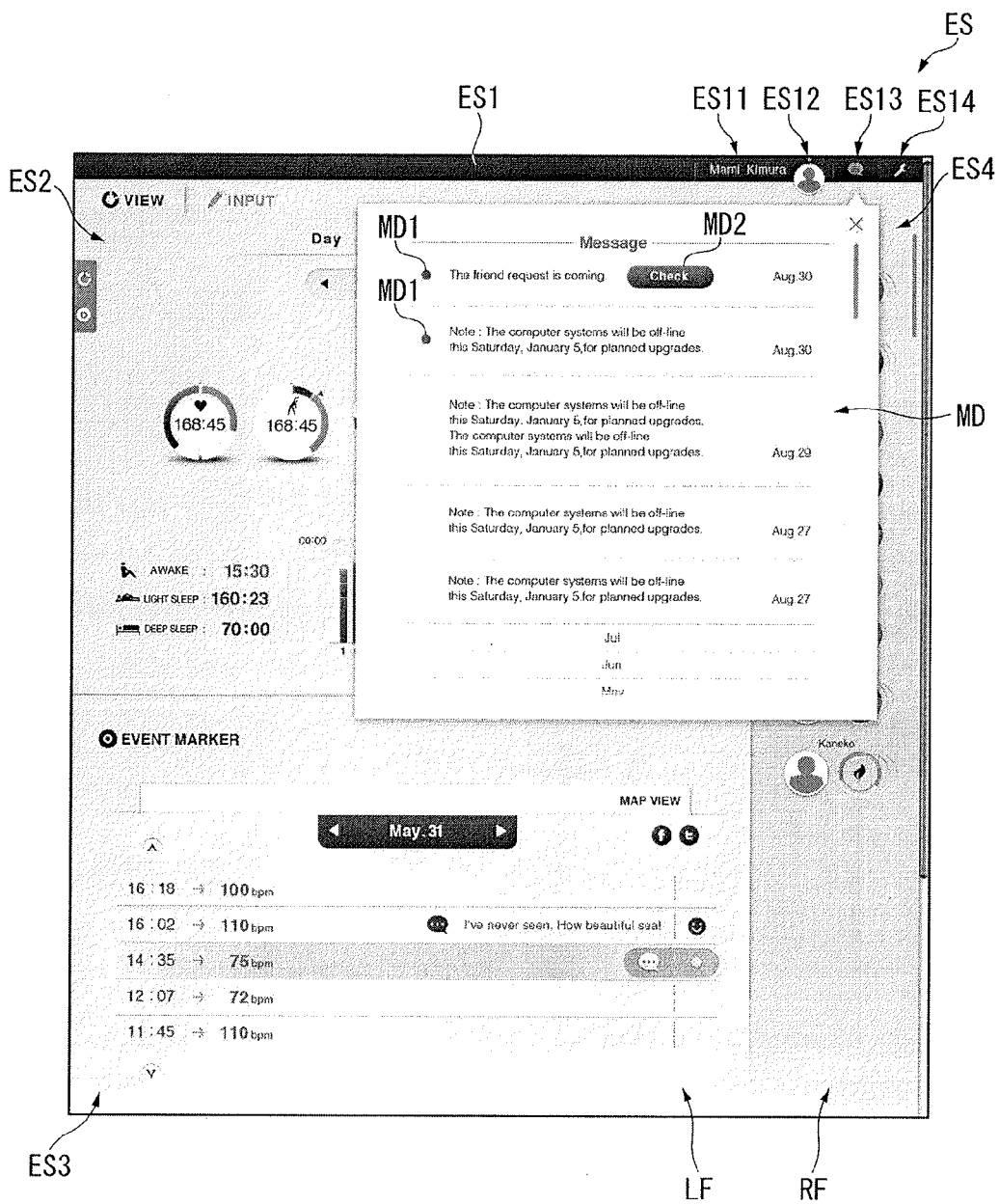
FIG. 58 is a diagram showing a message dialog in the embodiment.

When the icon ES13 is pressed, a message dialog MD shown in FIG. 58 is displayed. In the message dialog MD, latest messages are displayed in order from the top. Further, marks MD1 indicating messages acquired anew are set.

In an example shown in FIG. 58, a message at the top stage is the friend application message. In the message display field, a check key MD2 is set. When the check message MD2 is pressed, a friend management screen FS shown in FIG. 59 is displayed.

In the friend management screen FS, a field FS4 inscribed as "Request" is provided between the field FS1 and the field FS2. In the field FS4, information concerning the other person who transmits the friend application message and an icon FR indicating that the friend application message is received are displayed. Besides, the addition key TK is arranged in a lower part of the friend management screen FS.

Figure 60:
FIG. 60 is a diagram showing a check dialog in the embodiment.

When the addition key TK is pressed on the friend management screen FS, a check dialog CD shown in FIG. 60 is displayed. In the check dialog CD, besides a user name and an E-mail address of the other person who transmits the friend application message, an approval key CD1 indicating that a friend application is approved, a disapproval key CD2 indicating that the friend application is disapproved, and a close key CD3 for closing the check dialog CD are set.

Figure 59:
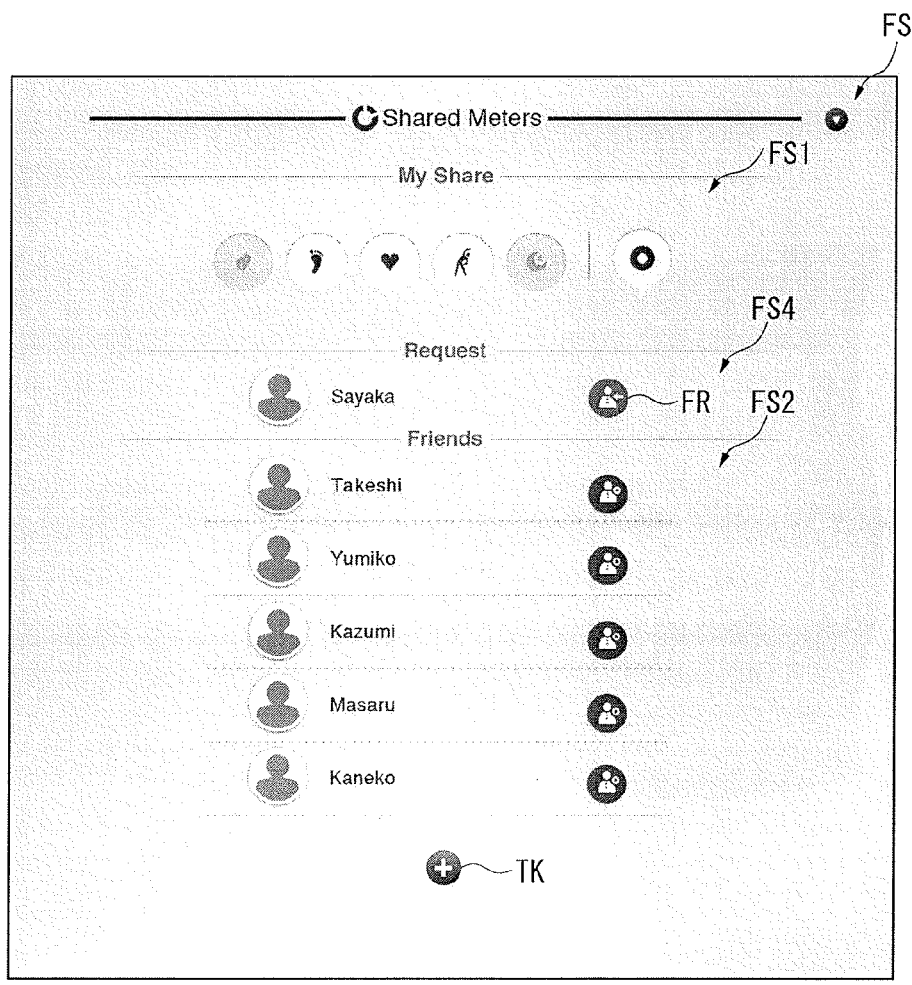
FIG. 59 is a diagram showing the friend management screen in the embodiment.

Note that, if the disapproval key CD2 is pressed when there is one kind of information concerning the other person displayed in the check dialog CD or if the close key CD3 is pressed, the check dialog CD is closed and returns to the friend management screen FS shown in FIG. 59.

Figure 61:
FIG. 61 is a diagram showing the check dialog in the embodiment.
Figure 62:
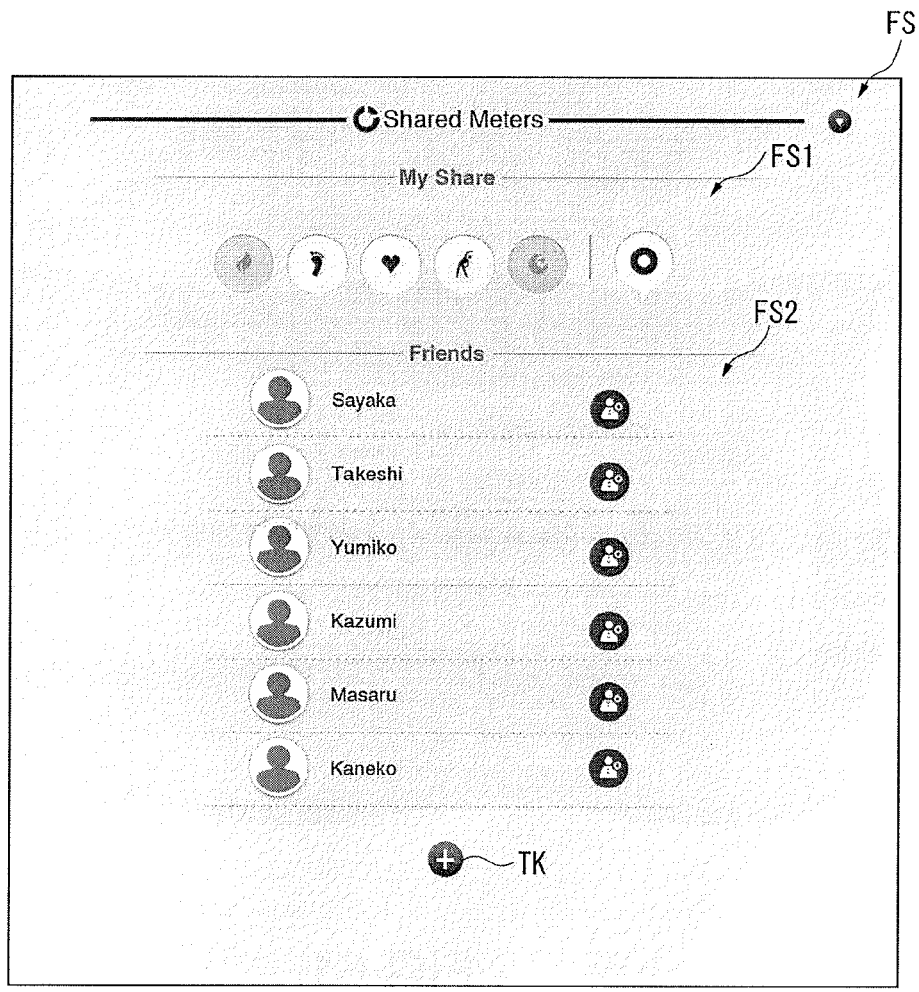
FIG. 62 is a diagram showing the friend management screen in the embodiment.

On the other hand, when the approval key CD1 is pressed, as shown in FIG. 61, a message "You are now friend!" is displayed in an area where the keys CD1 and CD2 are arranged in the check dialog CD. When the close key CD3 is pressed in this state, as shown in FIG. 62, the friend management screen FS is displayed in which information concerning the other person whose friend application is approved is added to the field FS2. In this case, information indicating that the user approves the friend application from the other person is transmitted from the information terminal 4 to the management server 5. The information is managed by the management server 5.

Figure 63:
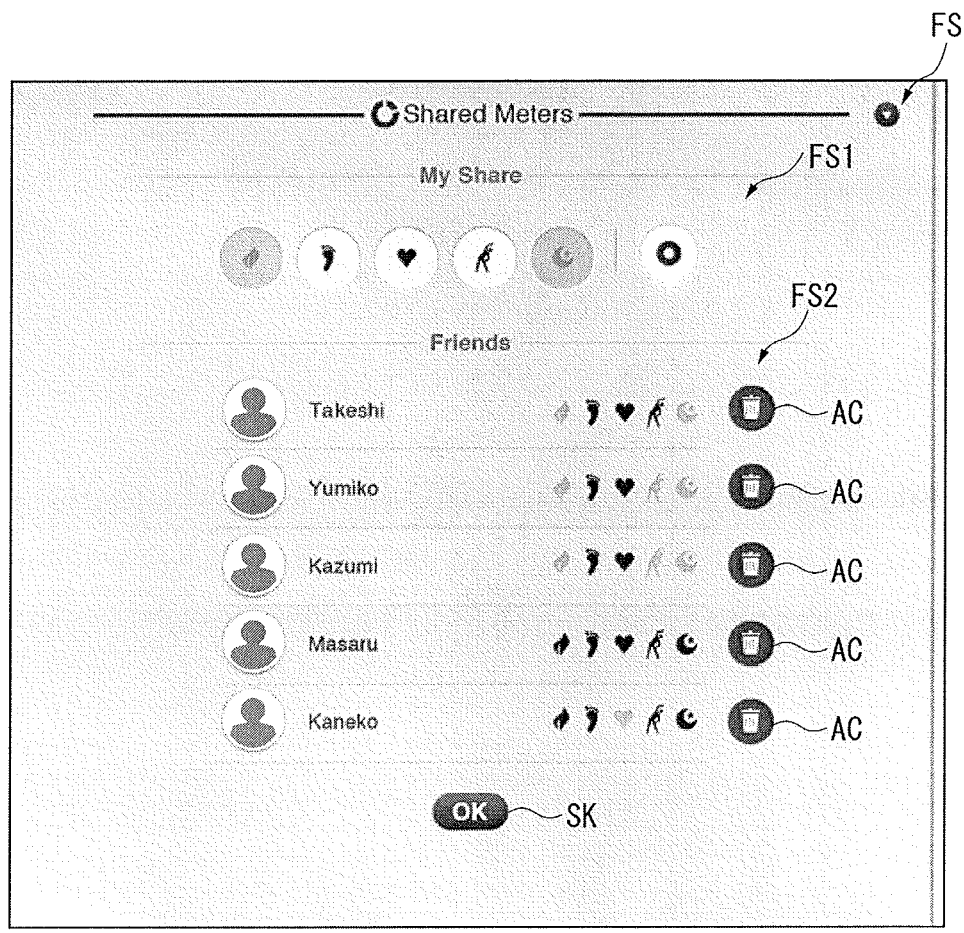
FIG. 63 is a diagram showing the friend management screen in the embodiment.

When the deletion key DK is pressed on the friend management screen FS shown in FIG. 53, as shown in FIG. 63, the icons AC imitating a trash can are respectively arranged on the right side of the information concerning the other people in the field FS2 (the information concerning the other people registered as friends). Further, a decision key SK is arranged in a lower part of the screen FS.

After the icon AC is pressed, when the decision key SK is pressed, the information concerning the other person in which the pressed icon AC is located is excluded from the friend registration. The information is transmitted from the information terminal 4 to the management server 5.

Effects of the Embodiment

With the measurement information management system 1 according to this embodiment explained above, there are effects explained below.

On the main screen MS displayed on the display unit 31 of the information terminal 3, the five meters M1 to M5 are arranged. Among the meters M1 to M5, one meter is located on the user's side in the depth direction on the main screen MS and the remaining four meters are located further on the depth side than the one meter. Consequently, by observing the main screen MS, the user can simultaneously grasp contents of a plurality of meters among the meters M1 to M5. Therefore, it is possible to improve bird's eye visibility of the main screen MS and make it easy to grasp information concerning items different from one another. Further, since the plurality of meters can be simultaneously observed, it is possible to cause the user to uniquely easily interpret information indicated by observable meters and cause the user to ponder a change in the information.

The meter located further on the inner side than the first position is displayed at low transparency. Consequently, the user can distinguish the meter located in the first position from the meter located on the inner side and gaze the meter located in the first position.

Similarly, the meter located further on the inner side than the first position is displayed smaller than the meter located in the first position. Consequently, as explained above, the user can distinguish the meter located in the first position from the meter located on the inner side and gaze the meter located in the first position.

Therefore, it is possible to make it easy to check the meters in the first position that the user should gaze.

The meters M1 to M5 are the doughnut graphs. Therefore, compared with when the information displayed by the meters M1 to M5 is indicated by a bar graph or a radar graph, it is possible to easily standardize display forms of the information and make it easy to grasp contents of the meters M1 to M5.

In the center of the meters M1 to M5, total values or differences of numerical values indicated by the meters are set. Besides, on the main screen MS, the detail display area DF in which a numerical value indicated by the meter located in the first position is displayed is arranged. Consequently, by observing the values set in the centers of the meters M1 to M5, the user can easily grasp contents of the meters. Besides, by checking the contents set in the detail display area DF, the user can grasp more in detail the contents of the information indicated by the meter located in the first position.

In the meter arrangement area LA on the main screen MS, the meters M1 to M5 are respectively arranged at equal intervals on the imaginary circle centering on the predetermined position in the depth direction of the main screen MS. The meter located in the first position is arranged in substantially the center of the meter arrangement area LA. Consequently, even when the meter located in the first position and the meter located in the second position are replaced, the arrangement of the five meters M1 to M5 does not change. Therefore, it is possible to give a sense of unity to the arrangement of the meters M1 to M5 and make it easy to view the meters M1 to M5.

For example, during the display of the main screen MS shown in FIG. 12, when the operation (flicking operation or dragging operation) for moving the meter M2 located in the second position in the direction from the meter M2 to the meter M1 located in the first position is performed, the display control unit 362 moves the meter M2 to the first position and moves the meter M1 located in the first position to the second position on the left side. Consequently, by performing the operation, it is possible to easily replace the meter located in the first position. Therefore, it is possible to change the positions of the meters with intuitive operation.

Since the information terminal 3 functioning as the measurement information display apparatus can directly communicate with the measuring apparatus 2 and acquire measurement information, it is possible to relatively quickly update contents of the meters M1 to M5 that display information based on the measurement information. Therefore, it is possible to relatively quickly check the information based on the measurement information.

During the display of the main screen MS, when measurement information is acquired from the measuring apparatus 2 anew, the display control unit 362 updates the displayed meters M1 to M5 on the basis of the measurement information. Consequently, it is possible to swiftly update the contents of the meters M1 to M5 compared with when the management server 5 generates display contents by the meters M1 and M5 and transmits the display contents to the information terminal 3, whereby the meters M1 to M5 are updated.

Modifications of the Embodiment

The invention is not limited to the embodiment. Modifications, improvements, and the like within a range in which the object of the invention can be attained are included in the invention.

In the embodiment, the measuring apparatus 2 is configured as the watch type apparatus. However, the invention is not limited to this. The measuring apparatus 2 may be an eyeglass type, a headset type, a helmet type, a glove type, and the like and may take any form as long as the measuring apparatus 2 can measure time, a pulse rate, and acceleration.

The information terminal 3 is configured as the cellular phone or the smart phone. However, the invention is not limited to this. The information terminal 3 may be, for example, a tablet. That is, the measuring apparatus 2 does not have to be a portable apparatus as long as the measuring apparatus 2 can acquire measurement information obtained by the measuring apparatus 2 and display the main screen MS and the like. Therefore, the information terminal 4 configured by the PC may be configured to display the screens displayed in the information terminal 3 such as the main screen MS.

In the embodiment, on the main screen MS, the meters M1 to M5, which are the doughnut graphs, indicating the excitement time, the exercise time, the sleep time, the intake/consumed calories, and the number of steps of the user are set. However, the invention is not limited to this. That is, the meters M1 to M5 may be graphs of other types such as a pie graph and a radar chart as long as the meters M1 to M5 can indicate these kinds of information. The same applies to the measurement information display screen ES2. Further, the number of meters set in the meter arrangement area LA is not limited to five and only has to be at least three. Further, the information indicated by the meters is not limited to the excitement time, the exercise time, the sleep time, the intake/consumed calories, and the number of steps and may be other information.

In the embodiment, on the main screen MS, the meters other than the meter in the first position are displayed with the transmittance reduced and is displayed smaller than the meter in the first position. However, the invention is not limited to this. That is, the meters other than the meter in the first position may be displayed at transmittance same as the transmittance of the meter in the first position and does not have to be displayed small as long as the meter in the first position can be recognized. The same applies to the measurement information display screen ES2 concerning the sizes of the meters.

In the embodiment, the meter located in the second position is moved to the first position by the flicking operation or the dragging operation from one side to the other side in the left-right direction. However, the invention is not limited to this. For example, a switch key for switching the meter located in the first position may be provided. In this case, the meter located in the first position only has to be switched every time the switch key is pressed.

In the embodiment, the information terminal 3 directly communicates with the measuring apparatus 2 and acquires measurement information from the measuring apparatus 2. However, the invention is not limited to this. That is, the information terminal 3 may be configured to always acquire measurement information from the management server 5.

In the embodiment, in order to simplify setting operation in the information terminal 3, the information terminal 3 acquires information such as a country, a time zone, and a language from the information set in advance in the information terminal 3 without causing the user to set the information. However, the invention is not limited to this. That is, the information terminal 3 may cause the user to input these kinds of information. The information terminal 3 may be configured to cause the user to input detailed setting information such as target weight, a target body fat rate, and an attainment period and create a diet program on the basis of the setting information input by the user.

As will be understood by those skilled in the art, the present invention may be embodied in other specific forms without departing from the essential characteristics thereof. Many other embodiments are possible without departing from the essential characteristics thereof. Many other embodiments are possible without deviating from the spirit and scope of the invention. These other embodiments are intended to be included within the scope of the present invention, which is set forth in the following claims.

What is claimed is:

1. An information terminal comprising:
   a communication unit configured to communicate measurement data with a physiological measurement apparatus;
   a control unit configured to:
   calculate sleep time information and calorie information including a total value of intake calories and a total value of consumed calories based on the measurement data, generate a first graph related to one of the sleep time information and the calorie information based on the calculated sleep time information or the calculated calorie information, and generate a second graph related to other one of the sleep time information and the calorie information based on the calculated sleep time information or the calculated calorie information;

a display unit configured to display the first graph and the second graph; wherein:

the first graph and the second graph are arranged in a first portion and a second portion along a virtual plane in a screen of the display unit such that the first graph and the second graph are reviewable at a same time, the control unit causes the display unit to display the first graph in the first portion and display the second graph in the second portion with a transmittance higher than the first graph, and display the second graph smaller than the first graph, the control unit updates the first graph and the second graph at the same time when the communication unit receives new measurement data from the physiological measurement apparatus, updating including:

calculating updated sleep time information and updated calorie information based on the new measurement data, generating an updated first graph related to one of the updated sleep time information and the updated calorie information based on the calculated updated sleep time information or the calculated updated calorie information, and generating an dated second graph related to other one of the updated sleep time information and the updated calorie information based on the calculated updated sleep time information or the calculated updated calorie information.

2. The information terminal according to claim 1, comprising:

an operation unit configured to output an operation signal corresponding to an operation by a user to the control unit; wherein the control unit updates the display unit to move the second graph from the second portion to the first portion, and move the first graph from the first portion to the second portion in response to the operation signal, wherein the control unit causes the display unit to display the second graph with the transmittance lower than the first graph, and display the second graph larger than the first graph.

3. The information terminal according to claim 1, wherein the control unit causes the display unit to move the second graph from the second portion to the first portion and move the first graph from the first portion to the second portion in response to a single operation signal provided by an operation unit.

4. The information terminal according to claim 1, wherein the second graph is related to the calorie information and includes a first bar representing the total value of the intake calories extending along a first direction, and a second bar representing the total value of the consumed calories extending along a second direction opposite to the first direction.

5. The information terminal according to claim 1, wherein the control unit is configured to calculate excitement time during exercise and excitement time during non-exercise based on the measurement data, the display unit is configured to display a third graph related to the excitement time during exercise and the excitement time during non-exercise in a third portion of the screen along the virtual plane, wherein the third graph is different from the first graph and the second graph in the transmittance and size, and the control unit updates the first graph, the second graph and the third graph at the same time when the communication unit receives new measurement data from the physiological measurement apparatus.

6. The measurement information display apparatus according to claim 5, wherein the first graph is larger than both the second graph and the third graph.

7. The measurement information display apparatus according to claim 1, wherein the first portion of the screen comprises the first graph and a numerical value corresponds to the first graph.

8. The measurement information display apparatus according to claim 1, wherein the display unit is configured to display a visual cue indicating that the control unit is updating the first graph and the second graph.

9. The measurement information display apparatus according to claim 1, wherein the first graph and the second graph have a same format.

* * * * *